US011420967B2

(12) United States Patent
Stella et al.

(10) Patent No.: US 11,420,967 B2
(45) Date of Patent: Aug. 23, 2022

(54) MODIFIED CARBAZOLES AS THERAPEUTIC AGENTS

(71) Applicants: UNIVERSITY OF WASHINGTON, Seattle, WA (US); THE UNIVERSITY OF MONTANA, Missoula, MT (US)

(72) Inventors: Nephi Stella, Seattle, WA (US); Philippe Diaz, Missoula, MT (US)

(73) Assignees: UNIVERSITY OF WASHINGTON, Seattle, WA (US); THE UNIVERSITY OF MONTANA, Missoula, MT (US)

( * ) Notice: Subject to any disclaimer, the term of this patent is extended or adjusted under 35 U.S.C. 154(b) by 20 days.

(21) Appl. No.: 16/960,541

(22) PCT Filed: Jun. 12, 2019

(86) PCT No.: PCT/US2019/036860
§ 371 (c)(1),
(2) Date: Jul. 7, 2020

(87) PCT Pub. No.: WO2019/241451
PCT Pub. Date: Dec. 19, 2019

(65) Prior Publication Data
US 2021/0094949 A1 Apr. 1, 2021

Related U.S. Application Data

(60) Provisional application No. 62/683,953, filed on Jun. 12, 2018, provisional application No. 62/714,436, filed on Aug. 3, 2018.

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01)

(58) Field of Classification Search
CPC combination set(s) only.
See application file for complete search history.

(56) References Cited

U.S. PATENT DOCUMENTS

| 9,084,771 B2 | 7/2015 | McAllister et al. |
| 2004/0039048 A1 | 2/2004 | Guzman Pastor et al. |
| 2015/0018369 A1 | 1/2015 | Stella et al. |

FOREIGN PATENT DOCUMENTS

| WO | 2008/092352 | 8/2008 |
| WO | 2013/106460 | 7/2013 |

OTHER PUBLICATIONS

Chakravarti, Bandana et al. "Cannabinoids as therapeutic agents in cancer: current status and future implications" Oncotarget (2014) vol. 5(15), pp. 5852-5872.

Galve-Roperh Ismael et al. "Anti-tumoral action of cannabinoids: involvement of sustained ceramide accumulation and extracellular signal-regulated kinase activation" Nat Med. (2000) vol. 6(3), pp. 313-319.
Kogan, Natalya M. "Synthesis and antitumor activity of quinonoid derivatives of cannabinoids" J Med Chem. (2004) vol. 47(15), pp. 3800-3806.
Guzmán, M. et al. "A pilot clinical study of Δ9-tetrahydrocannabinol in patients with recurrent glioblastoma multiforme" British Journal of Cancer (2006) vol. 95, pp. 197-203.
Sánchez, Cristina et al. "Inhibition of Glioma Growth in Vivo by Selective Activation of the CB2 Cannabinoid Receptor" Cancer Research (2001) vol. 61(15), pp. 5784-5789.
Cudaback, Eiron et al. "The Expression Level of CB1 and CB2 Receptors Determines Their Efficacy at Inducing Apoptosis in Astrocytomas" PLoS ONE (2010) vol. 5, Issue 1, pp. 1-10.
Stella, Nephi "Cannabinoid and cannabinoid-like receptors in microglia, astrocytes, and astrocytomas" GLIA (2010) vol. 58, Issue 9, pp. 1017-1030.
Amos, Linda A. "What tubulin drugs tell us about microtubule structure and dynamics" Semin Cell Dev Biol (2011) vol. 22, pp. 916-926.
Hyman, Anthony et al. "Preparation of modified tubulins" Methods in Enzymology (1991) vol. 196, pp. 478-485.
Hothi, Parvinder et al. "High-throughput chemical screens identify disulfiram as an inhibitor of human glioblastoma stem cells" Oncotarget (2012) vol. 3, pp. 1124-1136.
Kellogg, Glen E. et al. "HINT: a new method of empirical hydrophobic field calculation for CoMFA" J. Comput. Aided Mol. Des. (1991), vol. 5, pp. 545-552.
Burnett, J.C. et al. "A threonine turnstile defines a dynamic amphiphilic binding motif in the AAA ATPase p97 allosteric binding site" Org. Biomol. Chem. (2017) vol. 15, pp. 4096-4114.
Ewig, Carl S. et al. "Derivation of class II force fields. VIII. Derivation of a general quantum mechanical force field for organic compounds" J. Comput. Chem. (2001) vol. 22(15), pp. 1782-1800.
Zhao, Wei et al. "Structural insights into the inhibition of tubulin by the antitumor agent 4b-(1,2, 4-triazol-3-ylthio)-4-deoxypodophyllotoxin" ACS Chem. Biol. (2017) vol. 12, pp. 746-752.
Ravelli, Raimond B.G. et al. "Insight into tubulin regulation from a complex with colchicine and a stathmin-like domain" Nature (2004) vol. 428, pp. 198-202.
Nguyen, Tam Luong et al. "Evading Pgp activity in drug-resistant cancer cells: a structural and functional study of antitubulin furan metotica compounds" Mol. Canc. Therapeut. (2012) vol. 11, pp. 1103-1111.

(Continued)

*Primary Examiner* — Alexander R Pagano
(74) *Attorney, Agent, or Firm* — McDonnell Boehnen Hulbert & Berghoff LLP

(57) ABSTRACT

This disclosure relates to compounds that target microtubules, pharmaceutical compositions comprising them, and methods of using the compounds and compositions for treating diseases. More particularly, this disclosure relates to modified carbazole compounds and pharmaceutical compositions thereof, methods of targeting microtubules with these compounds, and methods of treating diseases affected by microtubule disruption.

24 Claims, 22 Drawing Sheets

(56) References Cited

OTHER PUBLICATIONS

Nguyen, Tam Luong et al. "A common pharmacophore for a diverse set of colchicine site inhibitors using a structure-based approach" J. Med. Chem. (2005) vol. 48, pp. 6107-6116.
Wagenbach, Michael et al. "A kinesin-13 mutant catalytically depolymerizes microtubules in ADP" J. Cell Biol. (2008) vol. 183, pp. 617-623.
Fung, Susan et al. "Novel indole-based compounds that differentiate alkylindole-sensitive receptors from cannabinoid receptors and microtubules: characterization of their activity on glioma cell migration" Pharmacol. Res. (2016) vol. 15, pp. 233-241.
Paull, Kenneth D. et al. "Identification of novel antimitotic agents acting at the tubulin level by computer-assisted evaluation of differential cytotoxicity data" Canc. Res. (1992) vol. 52, pp. 3892-3900.
D'Alessandris, Quintino Giorgio et al. "The clinical value of patient-derived glioblastoma tumorspheres in predicting treatment response" Neuro Oncol. (2017) vol. 19 (8), pp. 1097-1108.
Reinhold, William C. et al. "CellMiner: a web-based suite of genomic and pharmacologic tools to explore transcript and drug patterns in the NCI-60 cell line set" Canc. Res. (2012) vol. 72, pp. 3499-3511.
Patel, Anoop P. et al. "Single-cell RNA-seq highlights intratumoral heterogeneity in primary glioblastoma" Science (2014) vol. 344, pp. 1396-1401.
Vartanian, Alenoush et al. "GBM's multifaceted landscape: highlighting regional and microenvironmental heterogeneity" Neuro Oncol. (2014) vol. 16, pp. 1167-1175.
Sadhukhan, Pritam et al. "Selective proapoptotic activity of novel 3, 30-(aryl/alkyl-methylene) bis (2-hydroxynaphthalene-1, 4-dione) derivatives on human cancer cells via the induction reactive oxygen species" PLoS One (2016) vol. 11, pp. 1-22.
Filipuzzi, Ireos et al. "High-resolution genetics identifies the lipid transfer protein Sec14p as target for antifungal ergolines" PLoS Genet. (2016) vol. 12, pp. 1-19.
Almela, Maria Jesus et al. "A new set of chemical starting points with Plasmodium falciparum transmission-blocking potential for antimalarial drug discovery" PLoS One (2015) vol. 10, pp. 1-18 . . . .
Nguyen, Deborah G. et al. "Bioprinted 3D primary liver tissues allow assessment of organ-level response to clinical drug induced toxicity in vitro" PLoS One (2016) vol. 11, pp. 1-17.
Pollard, Steven M. et al. Glioma stem cell lines expanded in adherent culture have tumor-specific phenotypes and are suitable for chemical and genetic screens Cell Stem Cell (2009) vol. 4m pp. 568-580.
Lee, Jeongwu et al. "Tumor stem cells derived from glioblastomas cultured in bFGF and EGF more closely mirror the phenotype and genotype of primary tumors than do serum-cultured cell lines" Canc. Cell (2006) vol. 9, pp. 391-403.
Petrov, Ravil R. et al. "Mastering tricyclic ring systems for desirable functional cannabinoid activity" Eur. J. Med. Chem. (2013) vol. 69, pp. 881-907.
Verhaak, Roel G.W. et al. "Integrated genomic analysis identifies clinically relevant subtypes of glioblastoma characterized by abnormalities in PDGFRA, IDH1, EGFR, and NF1" Canc. Cell (2010) vol. 17, pp. 98-110.

Cherry, Allison E. et al. "ST-11: a new brain-penetrant microtubule-destabilizing agent with therapeutic potential for glioblastoma multiforme" Mol. Canc. Therapeut. (2016) vol. 15, pp. 2018-2029.
Hu, Laixing et al. Synthesis and structure-activity relationships of carbazole sulfonamides as a novel class of antimitotic agents against solid tumors J. Med. Chem. (2006) vol. 49, pp. 6273-6282.
Jordan, Mary Ann et al. "Microtubules as a target for anticancer drugs" Nat. Rev. Canc. (2004) vol. 4, pp. 253-265.
Giladi, Moshe et al. "Mitotic spindle disruption by alternating electric fields leads to improper chromosome segregation and mitotic catastrophe in cancer cells" Sci. Rep. (2015) vol. 5, pp. 1-16.
Stupp, Roger et al. "Maintenance therapy with tumortreating fields plus temozolomide vs temozolomide alone for glioblastoma: a randomized clinical trial" J. Am. Med. Assoc. (2015) vol. 314, pp. 2535-2543.
Oehler, Christoph et al. "Patupilone (epothilone B) for recurrent glioblastoma: clinical outcome and translational analysis of a single-institution phase I/II trial" Oncology (2012) vol. 83, pp. 1-9.
Herman, Jacob A. et al. "Molecular pathways: regulation and targeting of kinetochore-microtubule attachment in cancer" Clin. Canc. Res. (2015) vol. 21, pp. 233-239.
Calinescu, Anda-Alexandra et al. "Microtubule targeting agents in glioma" Transl. Cancer Res. (2016) vol. 5, pp. S54-S60.
Zhou, Rong et al. "Differential pharmacodynamic effects of paclitaxel formulations in an intracranial rat brain tumor model" J. Pharmacol. Exp. Therapeut. (2010) vol. 332, pp. 479-488.
Boumendjel, Ahcene et al. "A novel chalcone derivative which acts as a microtubule depolymerising agent and an inhibitor of P-gp and BCRP in in-vitro and in-vivo glioblastoma models" BMC Canc. 9 (2009) vol. 242, pp. 1-11.
Landen, Jaren W. et al. "Noscapine crosses the blood-brain barrier and inhibits glioblastoma growth" Clin. Canc. Res. (2004) vol. 10, pp. 5187-5201.
Yoshida, Daizo et al. "Drug-induced apoptosis by anti-microtubule agent, estramustine phosphate on human malignant glioma cell line, U87MG; in vitro study" J. Neuro Oncol. (2000) vol. 47, pp. 133-140.
Matson, Daniel R. "Spindle poisons and cell fate: a tale of two pathways" Mol. Interv. (2011) vol. 11, pp. 141-150.
Liu, Yi-Min et al. "Tubulin inhibitors: a patent review" Expert Opin. Ther. Pat. (2014) vol. 24, pp. 69-88.
Garcia, Celina et al. "The orthotopic xenotransplant of human glioblastoma successfully recapitulates glioblastoma-microenvironment interactions in a non-immunosuppressed mouse model" BMC Cancer (2014) vol. 14(923), pp. 1-11.
The International Search Report (ISR) with Written Opinion for PCT/US2019/036860 dated Aug. 2, 2019, pp. 1-21.
Diaz, Philippe et al. "Modified carbazoles destabilize microtubules and kill glioblastoma multiform cells" European Journal of Medicinal Chemistry (2018) vol. 159, pp. 74-89.
Jimenez, Carmen et al. "Exploring the size adaptability of the B ring binding zone of the colchicine site of tubulin with para-nitrogen substituted isocombretastatins" European Journal of Medicinal Chemistry (2015) vol. 100, pp. 210-222.
Niu, Miaomiao et al. "The discovery of potential tubulin inhibitors: A combination of pharmacophore modeling, virtual screening, and molecular docking studies" Journal of the Taiwan Institute of Chemical Engineers (2014) vol. 45(5), pp. 2111-2121.
Niu, Miao-miao et al. "Tubulin inhibitors:pharmacophore modeling, virtual screening and molecular docking" CTA Pharmacologica Sinica (2014) vol. 35(7), pp. 967-979.

A.

B.

C.

D.

A.

B.

A.

B.

A.

B.

A  ST-401 competes for [³H]colchicine binding to tubulin

B  ST-401 triggers MT disassembly

IC$_{50}$=719 nM

MODIFIED CARBAZOLES AS THERAPEUTIC AGENTS

CROSS-REFERENCE TO RELATED APPLICATIONS

This application is a national stage application under 35 U.S.C. § 371 of International Application No. PCT/US2019/036860, filed Jun. 12, 2019, which claims the benefit of priority of U.S. Provisional Patent Application No. 62/683,953, filed Jun. 12, 2018, and U.S. Provisional Patent Application No. 62/714,436, filed Aug. 3, 2018, both of which are incorporated by reference in their entirety.

STATEMENT REGARDING FEDERALLY SPONSORED RESEARCH OR DEVELOPMENT

This invention was made with government support under Grant Nos. P30 NS055022 and R01 DA014486 and R41 AR069416 and R43 CA165452, awarded by the National Institutes of Health. The government has certain rights in the invention.

BACKGROUND OF DISCLOSURE

Field of Disclosure

This disclosure relates to compounds that target microtubules (MTs), pharmaceutical compositions comprising them, and methods of using the compounds and compositions for treating diseases. More particularly, this disclosure relates to modified carbazole compounds and pharmaceutical compositions thereof, methods of targeting MTs with these compounds, and methods of treating diseases affected by MT disruption.

Technical Background

Brain tumors such as astrocytomas IV (also known as glioblastoma multiforme or GBM) and cancers having mutation in the B-Raf proto-oncogene serine/threonine kinase (BRAF) gene resulting in a valine-to-glutamate change at the residue 600 (V600E) are particularly devastating. GBMs and BRAF-mutant cancers develop in peripheral tissues and metastasize to the brain. These tumors progress rapidly through healthy brain parenchyma and resist all current therapeutic approaches, making them one of the most devastating of all cancers. Patients diagnosed with astrocyomas grade IV and BRAF-mutant brain metastasis typically die within two years. Even aggressive therapeutic interventions (i.e., combining surgery, radiotherapy and available chemotherapeutics) extend the life expectancy of these patients by only a few months. All drugs and adjuvants developed to kill such cancers (e.g., novel alkylating agents, small molecules targeting driver mutations and monoclonal antibodies) have produced minimal therapeutic benefits. Thus, a radically different therapeutic approach needs to be taken in order to treat such cancers.

In recent years, a number of studies have suggested the existence of proteins that critically control cancer growth and metastasis, and are activated by carbazole small molecules: the MT and drivers mutation, such as BRAF-mutant, that confer vulnerability to compounds which target MT (MT targeting agents, MTAs). The tubulin proteins represent the basic functional component of MT and as such may also be implicated in disease, and to use such protein, alone or as part of a panel of other protein targets, to identify and profile the effects of potential therapeutic compounds capable of treating one or other of the many diseases and disorders mediated by MT.

To date, many subtypes of cancers are successfully treated with MTAs, including breast, lung and head and neck tumors, lymphoma and melanoma. MTAs act by binding to tubulin or MTs and disrupting MT assembly, disassembly and dynamics, all of which impair the precise orchestration of mitosis and triggers cell death by engaging the MT spindle check-point. Starting in the 2000s, evidence suggested that GBM, the most common, devastating and incurable type of brain cancer, is particularly sensitive to MTAs. The sensitivity of GBM cells likely results from the expression of mutated proteins that erroneously control MT dynamics and their interactions with kinetochores. Accordingly, several studies have shown that GBM cells treated with MTAs undergo death through MT spindle check-point arrest and ensuing apoptosis. Human clinical trials showed that MTA treatment reduces tumor burden in patients diagnosed with GBM, and the recent advent of tumor-treating fields for the treatment of patients diagnosed with GBM provide additional evidence that GBMs are sensitive to the disruption of MT function. Specifically, the polarizing field established by tumor-treating fields affects tubulin assembly into MTs, disrupts mitosis and triggers the spindle check-point and ensuing cell death. Together, these genetic, pharmacological, and tumor-treating field findings show that GBM cells are particularly sensitive to alterations in MT function.

There are several classes of MTAs that disrupt MT function through distinct mechanisms of action (MOA). Three of the most extensively studied classes of MTAs are vinca alkaloids, taxanes and colchicinoids, which bind to distinct sites on tubulin and differentially affect MT dynamics. Prototypical MTAs that bind to the colchicine sites include combretastatin A-4 (CAS RN No. 117048-59-6; (1)), the carbazole-based analogues of combretastatin (such as 9-ethyl-N-(3,4,5-trimethoxyphenyl)-9H-carbazole-3-sulfonamide (2)) that weakly inhibit tubulin polymerization and yet triggers pronounced apoptosis, and nocodazole (CAS RN No. 31430-18-9; (3)), which rapidly and fully inhibits tubulin polymerization and triggers apoptosis in cancer cells.

Because of the shortcomings of existing brain cancer treatments, there is a need in the art for improved therapies (including novel MTAs) that provide meaningful therapeutic intervention against brain tumors.

SUMMARY OF THE DISCLOSURE

The disclosure provides novel modified carbazole compounds useful for treating cancer. Thus, one aspect of the disclosure provides an isolated or purified compound of that binds to the colchicine site of tubulin, wherein the compound comprises a hydroxymethyl moiety that links the carbazole to aromatic moiety, an ethyl moiety linked to the nitrogen atom of the carbazole and select chemical modifications in the second aromatic moiety.

Another aspect provides an isolated or purified compound that binds to the colchicine site of tubulin, wherein the compound comprises a carbazole having an ethyl group attached to the carbazole.

Another aspect of the disclosure provides compounds of formula (I):

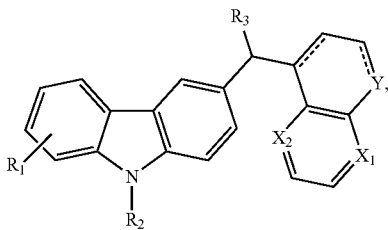

or a pharmaceutically acceptable salt or prodrug thereof, or a stereoisomer thereof, wherein
each ---- independently represents a single or double bond, provided that the bond satisfies the valence requirement of the C and/or N atoms;
$X_1$ and $X_2$ are independently selected from CH and N;
Y is $C(R_4)_2$ or $NR_4$ when ---- represents a single bond, or Y is $CR_4$ or N when ---- represents a double bond; wherein each $R_4$ is independently hydrogen or $C_1$-$C_6$ alkyl optionally substituted with one or more $R_5$;
$R_1$ is selected from the group consisting of hydrogen, halogen, $C_1$-$C_6$ alkyl optionally substituted with one or more $R_6$, $C_2$-$C_6$ alkenyl optionally substituted with one or more $R_6$, $C_2$-$C_6$ alkynyl optionally substituted with one or more $R_6$, —O($C_1$-$C_6$ alkyl), and —CO($C_1$-$C_6$ alkyl) optionally substituted with one or more $R_6$;
$R_2$ is selected from the group consisting of $C_1$-$C_6$ alkyl optionally substituted with one or more $R_7$, $C_2$-$C_6$ alkenyl optionally substituted with one or more $R_7$, $C_2$-$C_6$ alkynyl optionally substituted with one or more $R_7$, —CO($C_1$-$C_6$ alkyl) optionally substituted with one or more $R_7$, aryl ($C_0$-$C_6$ alkyl) optionally substituted with one or more $R_8$, heteroaryl($C_0$-$C_6$ alkyl) optionally substituted with one or more $R_8$, heterocyclyl($C_0$-$C_6$ alkyl) optionally substituted with one or more $R_7$, and cycloalkyl($C_0$-$C_6$ alkyl) optionally substituted with one or more $R_7$; and
$R_3$ is —OH, —O($C_1$-$C_6$ alkyl), —$NH_2$, —NH($C_1$-$C_6$ alkyl), —N($C_1$-$C_6$ alkyl)$_2$, —SH, or —S($C_1$-$C_6$ alkyl),
wherein:
each $R_5$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2H$, and —$CO_2$($C_1$-$C_6$ alkyl);
each $R_6$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2H$, and —$CO_2$($C_1$-$C_6$ alkyl);
each $R_7$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2H$, and —$CO_2$($C_1$-$C_6$ alkyl), or two $R_7$ groups when attached to the same carbon atom form =O; and each $R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —$CO_2H$, and —$CO_2$($C_1$-$C_6$ alkyl).

Another aspect provides an isolated or purified microtubule-targeting agent (or enantiomer thereof) wherein the microtubule-targeting agent retains the functions of: a) steric occupation of a moiety of similar size to a naphthyl, quinolinyl or trimethoxy-aryl system with preferably a hydrogen bond interacting with the β-Cys-241 sulfhydral; b) lack of cationic ionizability for moieties that occupy the trimethoxy-aryl subsite; c) reduction of conformational isomerism by either intramolecular steric hindrance or inherent rigidity; and d) a strong hydrogen bond acceptor with an overlapping orientation with of the methanone oxygen atom of compound 20 (herein) and the lactone carbonyl oxygen atom of podophyllotoxins.

In certain embodiments, the microtubule-targeting agent exhibits one of the characteristics of: destabilizing MT, anti-neoplastic activity, preferential sensitivity of BRAF mutant melanoma cells, cell killing activity of melanocytes expressing BRAF mutants, synergy with vemurafenib (PLX4032, Zelboraf®), fluorouracil (5-FU), and/or paclitaxel, increased cell killing by one enantiomer when compared to the other enantiomer; or a combination of two or more of the above.

Another aspect of the disclosure provides a pharmaceutical composition including one or more compounds of the disclosure as described herein and a pharmaceutically acceptable carrier, solvent, adjuvant or diluent.

Another aspect of the disclosure provides a method of treating cancer. Such method includes administering to a subject in need of such treatment one or more compounds of the disclosure as described herein or a pharmaceutical composition of the disclosure as described herein.

In certain embodiments of this disclosure, the method further includes administering one or more secondary therapeutic agents as described herein.

Another aspect of the disclosure provides use of one or more compounds of the disclosure as described herein or a pharmaceutical composition of the disclosure as described herein for the treatment of cancer.

Another aspect of the disclosure provides use of one or more compounds of the disclosure as described herein or a pharmaceutical composition of the disclosure as described herein in the manufacture of a medicament for treating cancer.

In certain embodiments of these aspects, the cancer is a BRAF-mutant cancer. In certain embodiments of this aspect, the cancer is melanoma, brain cancer, colorectal cancers, lung cancer, breast cancer, head and neck tumors, and lymphoma. In certain embodiments, the cancer is glioblastoma multiforme. In certain embodiments, the cancer develops in peripheral tissues and metastasizes to the brain.

Another aspect of the disclosure provides methods of treating cancer, comprising administering one or more secondary therapeutic agents and one or more compounds selected from:
9-ethyl-3-[(4-methylnaphthalen-1-yl)carbonyl]-9H-carbazole (8),
9-ethyl-3-(4-methylpiperazine-1-carbonyl)-9H-carbazole (9),
3-(4-chlorobenzoyl)-9-ethyl-9H-carbazole (10),
9-ethyl-3-(4-fluorobenzoyl)-9H-carbazole (11), 9-ethyl-3-(4-methylbenzoyl)-9H-carbazole (12),
1-(9-ethyl-9H-carbazol-3-yl)-2-phenylethan-1-one (13),
9-ethyl-3-(naphthalene-1-carbonyl)-9H-carbazole (14),
9-propyl-3-[(4-methylnaphthalen-1-yl)carbonyl]-9H-carbazole (16),
3-(4-methylnaphthalene-1-carbonyl)-9-(2,2,2-trifluoroethyl)-9H-carbazole (18),
9-ethyl-3-(quinoline-5-carbonyl)-9H-carbazole (20),
9-ethyl-3-(quinoline-8-carbonyl)-9H-carbazole (22),
(9-ethyl-9H-carbazol-3-yl)(1,2,3,4-tetrahydroquinolin-5-yl)methanone (23),
9-ethyl-3-(1,2,3,4-tetrahydroquinoline-8-carbonyl)-9H-carbazole (24),
9-ethyl-3-[(1,2,3,4-tetrahydroquinolin-1-yl)carbonyl]-9H-carbazole (25),
9-ethyl-3-(4-methylnaphthalene-1-carbothioyl)-9H-carbazole (26),
9-(4-methylnaphthalene-1-carbonyl)-9H-carbazole (28),
9-ethyl-2-methoxy-6-(4-methylnaphthalene-1-carbonyl)-9H-carbazole (31),
5-ethyl-2-[(4-methylnaphthalen-1-yl)carbonyl]-1H,2H,3H,4H,5H-pyrido[4,3-b]indole (35),
and a pharmaceutically acceptable salt thereof,
to a subject in need thereof.

Another aspect of the disclosure provides a method of treating diseases associated with cannabinoid 1 ($CB_1$) receptor and/or cannabinoid 2 ($CB_2$) receptor, in a subject in need thereof. Such method includes administering one or more compounds of the disclosure as described herein or a pharmaceutical composition of the disclosure as described herein.

Additional aspects of the disclosure will be evident from the disclosure herein.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

DETAILED DESCRIPTION

Figure 1:
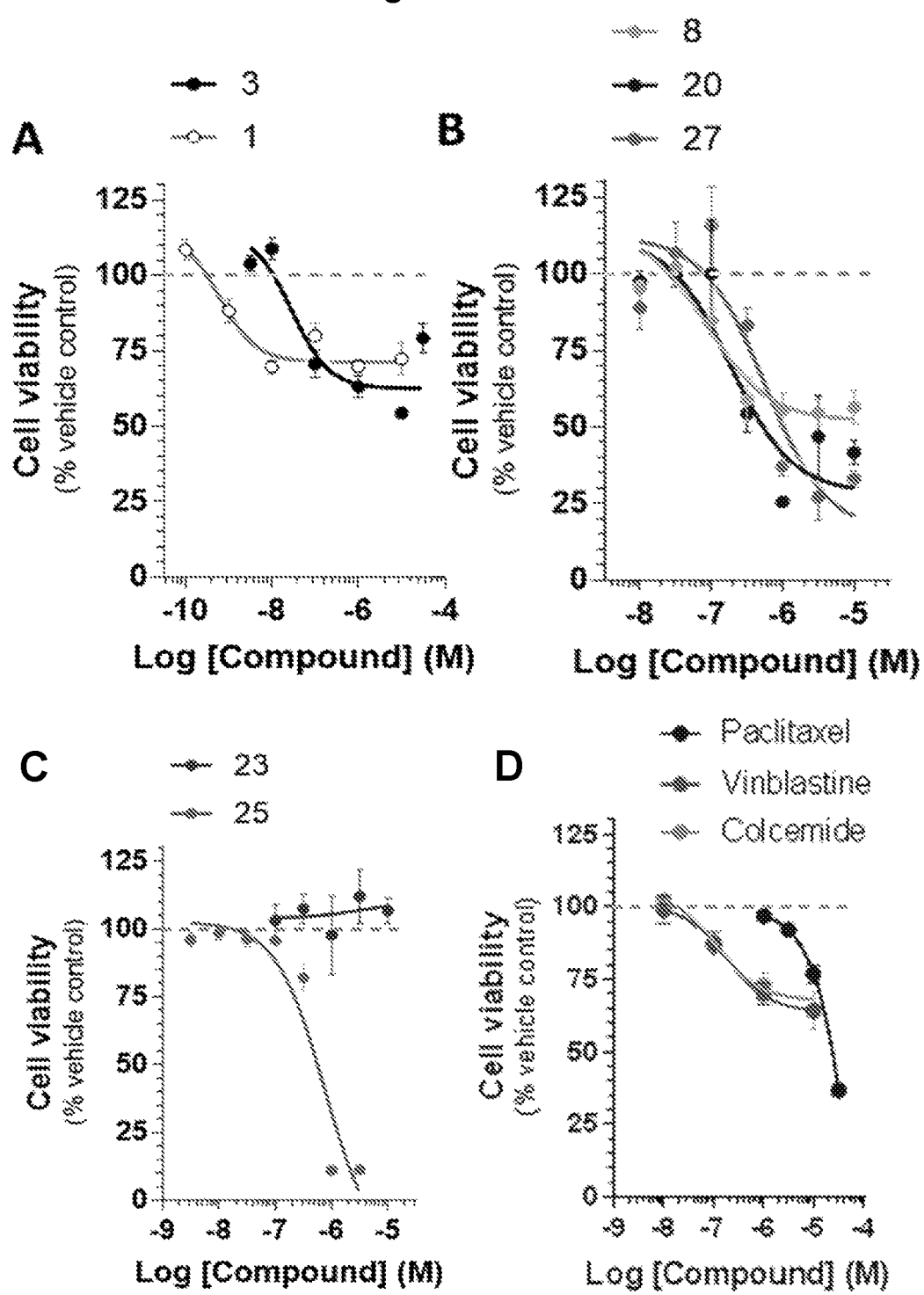
FIG. 1 illustrates antitumor activity of reference MTAs that target the colchicine site, as well as select modified-carbazoles, in T98G GBM cells in culture. T98G cells in culture were treated with increasing concentrations of A: two MTAs acting through the colchicine site of tubulin, combretastatin A-4 (1) and nocodazole (3), B: compounds 8, 20 and 27, and C: compounds 23 and 25. Cell viability was measured 72 hours following treatment using WST-1. Dotted line shows 100% vehicle control. Data are the mean±SEM of at least three independent experiments performed in triplicate.

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials and methods provide improvements in treatment of cancer. Specifically, the inventors found that the compounds of the disclosure destabilize MTs by binding to the colchicine site of tubulin in a similar mode to a podophyllotoxin analogue and appears to interact with a unique low interaction binding space. Several compounds of the disclosure trigger marked cell death in multiple GBM model systems while exhibiting a much less lower activity in the HepG2 liver cells, suggesting a promising therapeutic index. The use of the heterocyclic carbazole scaffold provides several advantages when considering the future optimization of small-molecule for therapeutic use. For example, this scaffold can be modified in a variety of ways using readily available and simple starting materials, and their chemical modification typically requires only as few steps of well-established chemistry, thereby providing a versatile scaffold for medicinal chemistry optimization. In summary, this work increases our understanding of how targeting the colchicine site by small molecules affects tubulin assembly and disrupts MT function, and provides a reference design approach to develop the next generation of MTAs for treating devastating cancers, such as GBM.

As provided above, the disclosure provides compounds of formula (I). Particularly useful compounds of formula (I) are those wherein only one of $X_1$ and $X_2$ can be N.

Particularly useful compounds for use in the methods of the disclosure are the compounds of formula (I) wherein $X_2$ is CH (i.e., $X_1$ is N or $X_1$ is CH). In certain embodiments, such compounds are of formula (I-A):

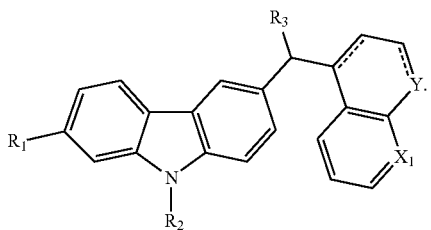
(I-1)

One embodiment of the disclosure provides compounds where each ---- is independently a single bond. In certain embodiments, such compounds are of formula (I-2):

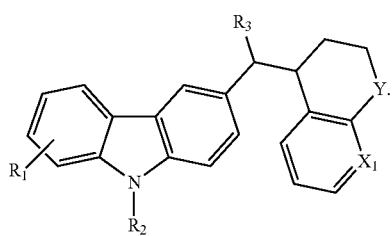
(I-2)

In certain embodiments, such compounds are of formula (I-3):

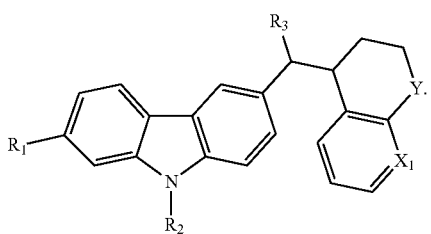
(I-3)

Another embodiment of the disclosure provides compounds of formula (I), (I-2) or (I-3) as otherwise described herein wherein Y is $C(R_4)_2$. In some embodiments, each $R_4$ is independently hydrogen. In some embodiments, each $R_4$ is independently $C_1$-$C_6$ alkyl optionally substituted with one or more $R_5$. In some embodiments, each $R_4$ is independently $C_1$-$C_6$ alkyl. In some embodiments, each $R_4$ is independently methyl. In some embodiments, each $R_4$ is independently hydrogen or $C_1$-$C_5$ alkyl optionally substituted with one or more $R_5$. In some embodiments, each $R_4$ is independently hydrogen or $C_1$-$C_6$ alkyl. In some embodiments, each $R_4$ is independently hydrogen or methyl.

Another embodiment of the disclosure provides compounds of formula (I), (I-2) or (I-3) as otherwise described herein wherein Y is $NR_4$. In some embodiments, $R_4$ is hydrogen. In some embodiments, $R_4$ is $C_1$-$C_6$ alkyl optionally substituted with one or more $R_5$. In some embodiments, $R_4$ is $C_1$-$C_6$ alkyl. In some embodiments, $R_4$ is methyl.

One embodiment of the disclosure provides compounds where each ---- is independently a double bond. In certain embodiments, such compounds are of formula (I-4):

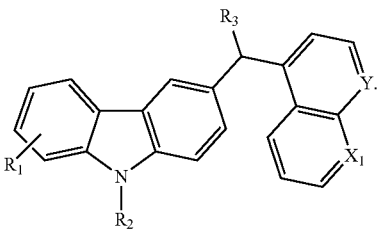
(I-4)

In certain embodiments, such compounds are of formula (I-5):

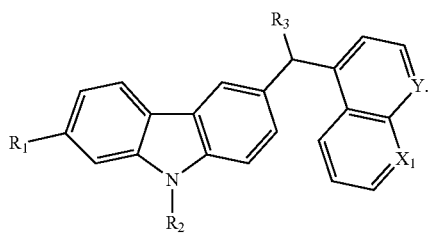
(I-5)

Another embodiment of the disclosure provides compounds of formula (I), (I-2), (I-4) or (I-5) as otherwise described herein wherein Y is $CR_4$. In some embodiments, $R_4$ is hydrogen. In some embodiments, $R_4$ is $C_1$-$C_6$ alkyl optionally substituted with one or more $R_5$. In some embodiments, $R_4$ is $C_1$-$C_6$ alkyl. In some embodiments, $R_4$ is methyl.

Another embodiment of the disclosure provides compounds of formula (I), (I-2), (I-4) or (I-5) as otherwise described herein wherein Y is N.

Other compounds useful in the methods of the disclosure are the compounds of formula (I) wherein $X_1$ is CH and $X_2$ is N. Such compounds are of formula (I-6):

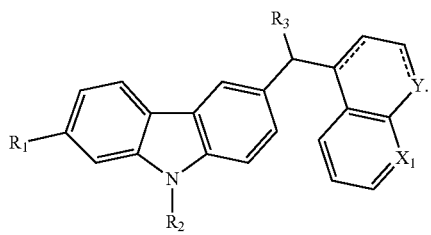
(I-6)

In some embodiments, the compounds of formula (I-6) as otherwise described herein are those where Y is CR₄ (i.e., when each ---- is independently a double bond). In certain embodiments, R₄ is as defined below with respect to formula (I), (I-2), (I-4) or (I-5).

In certain embodiments of the disclosure, the compounds of formula (I)-(I-6) as otherwise described herein are those wherein $R_1$ is hydrogen, halogen, or $C_1$-$C_6$ alkyl. For example, in certain embodiments, $R_1$ is hydrogen, fluorine, methyl or ethyl. In certain other embodiments, $R_1$ is hydrogen or $C_1$-$C_6$ alkyl. In certain other embodiments, $R_1$ is hydrogen, methyl or ethyl. In certain embodiments, $R_1$ is hydrogen.

Another embodiment of the disclosure provides compounds of formula (I)-(I-6) as otherwise described herein wherein $R_2$ is $C_1$-$C_6$ alkyl optionally substituted with one or more $R_7$, aryl($C_0$-$C_6$ alkyl) optionally substituted with one or more $R_8$, heteroaryl($C_0$-$C_6$ alkyl) optionally substituted with one or more $R_8$, heterocyclyl($C_0$-$C_6$ alkyl) optionally substituted with one or more $R_7$, or cycloalkyl($C_0$-$C_6$ alkyl) optionally substituted with one or more $R_7$. In certain embodiments, $R_2$ is $C_1$-$C_6$ alkyl optionally substituted with one or more $R_7$, aryl($C_1$-$C_6$ alkyl) optionally substituted with one or more $R_8$, heteroaryl($C_1$-$C_6$ alkyl) optionally substituted with one or more $R_8$, heterocyclyl($C_1$-$C_6$ alkyl) optionally substituted with one or more $R_7$, or cycloalkyl($C_1$-$C_6$ alkyl) optionally substituted with one or more $R_7$. In certain embodiments, $R_2$ is $C_1$-$C_6$ alkyl optionally substituted with one or more $R_7$, aryl($C_1$-$C_2$ alkyl) optionally substituted with one or more $R_8$, heteroaryl($C_1$-$C_2$ alkyl) optionally substituted with one or more $R_8$, heterocyclyl($C_1$-$C_2$ alkyl) optionally substituted with one or more $R_7$, or cycloalkyl($C_1$-$C_2$ alkyl) optionally substituted with one or more $R_7$.

In certain embodiments of the disclosure, the compound of formula (I)-(I-6) as otherwise described herein is wherein $R_2$ is $C_1$-$C_6$ alkyl optionally substituted with one or more $R_7$, aryl($C_1$-$C_2$ alkyl) optionally substituted with one or more $R_8$, or cycloalkyl($C_1$-$C_2$ alkyl) optionally substituted with one or more $R_7$.

In certain embodiments of the disclosure, the compound of formula (I)-(I-6) as otherwise described herein is wherein $R_2$ is $C_1$-$C_6$ alkyl optionally substituted with one or more $R_7$. In certain embodiments, $R_2$ is $C_1$-$C_4$ alkyl optionally substituted with one or more $R_7$. In certain embodiments, $R_2$ is $C_1$-$C_2$ alkyl optionally substituted with one or more $R_7$.

In certain embodiments of the disclosure, the compound of formula (I)-(I-6) as otherwise described herein is wherein $R_2$ is $C_1$-$C_4$ alkyl. In certain other embodiments of the disclosure, the compound of formula (I)-(I-6) as otherwise described herein is wherein $R_2$ is $C_1$-$C_2$ alkyl.

Another embodiment of the disclosure provides compounds of formula (I)-(I-6) as otherwise described herein wherein $R_7$ is independently selected from the group consisting of halogen, —CN, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —CONH₂, —CONH($C_1$-$C_6$ alkyl), —CON($C_1$-$C_6$ alkyl)₂, —CO₂H, and —CO₂($C_1$-$C_6$ alkyl). In some embodiments, $R_7$ is independently selected from the group consisting of halogen, —ON, —NH₂, —NH($C_1$-$C_6$ alkyl), —N($C_1$-$C_6$ alkyl)₂, —OH, $C_1$-$C_6$ alkoxy, and $C_1$-$C_6$ haloalkoxy; or wherein $R_7$ is independently selected from the group consisting of halogen, —NH₂, —NH($C_1$-$C_6$ alkyl), —N($C_1$-$C_6$ alkyl)₂, —OH, $C_1$-$C_6$ alkoxy, and $C_1$-$C_6$ haloalkoxy. In some embodiments, $R_7$ is independently halogen.

Particularly useful compounds of formula (I) are those having the structure:

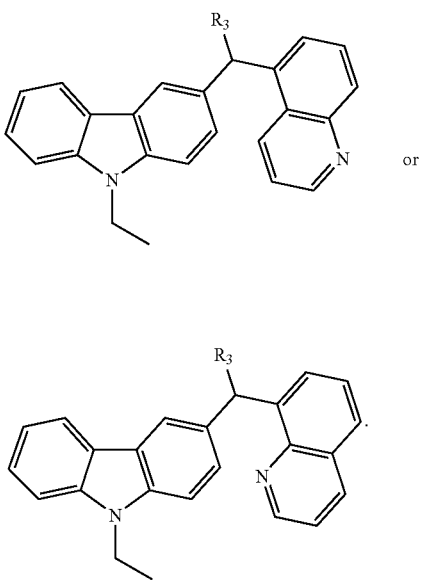

or

In certain additional embodiments, including any of the embodiments described with reference to formulae (I)-(I-6) and the preceding embodiment, the compounds are those where $R_3$ is —OH.

Another embodiment of the disclosure provides compounds of formula (I)-(I-6) and the preceding embodiments wherein $R_3$ is —OH, —O($C_1$-$C_6$ alkyl), —NH₂, —NH($C_1$-$C_6$ alkyl), or —N($C_1$-$C_6$ alkyl)₂. In certain embodiments, $R_3$ is —OH or —O($C_1$-$C_6$ alkyl). In certain embodiments, $R_3$ is —OH or —OCH₃. In certain embodiments, $R_3$ is —OH, —NH₂, or —SH.

The compounds of the disclosure may be racemic or enantiomerically pure. In certain embodiments, the compound of formula (I)-(I-6) as otherwise described herein is racemic. In certain embodiments, the compound of formula (I)-(I-6) as otherwise described herein is substantially enantiomerically pure (e.g., more than 90%, or more than 95%, or even more than 99% is a single enantiomer). In some embodiments, the substantially enantiomerically pure may be a (−)-enantiomer. In some embodiments, the substantially enantiomerically pure may be a (+)-enantiomer.

Some example compounds of formula (I) include, but are not limited to:

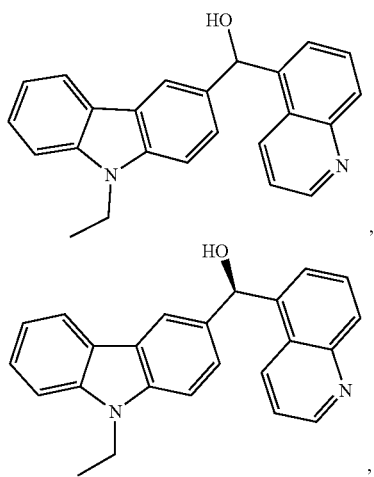

,

-continued

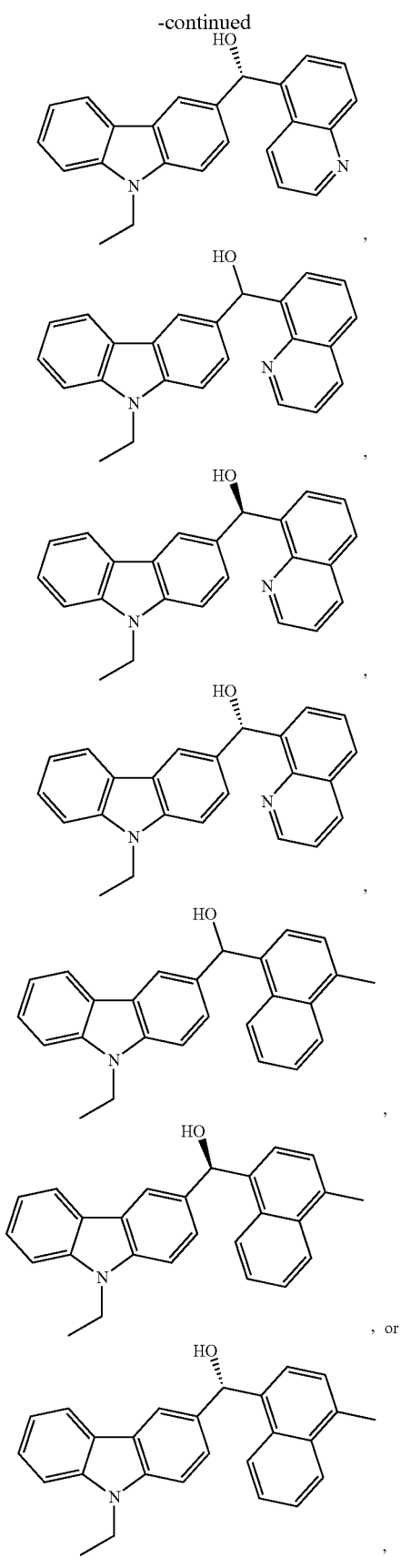

or pharmaceutically acceptable salt thereof.

In some embodiments of the disclosure the compound of formula (I) is (9-ethyl-9H-carbazol-3-yl)(quinolin-5-yl)methanol or a pharmaceutically acceptable salt thereof, or a stereoisomer thereof.

In some embodiments of the disclosure the compound of formula (I) is (9-ethyl-9H-carbazol-3-yl)(quinolin-8-yl)methanol or a pharmaceutically acceptable salt thereof, or a stereoisomer thereof.

In some embodiments of the disclosure the compound of formula (I) is (9-ethyl-9H-carbazol-3-yl)(4-methylnaphthalen-1-yl)methanol.

In certain additional embodiments, including any of the embodiments described with reference to formulae (I)-(I-6) and embodiments disclosed above, each cycloalkyl recited in any one of the preceding embodiments is a 3-7 membered monocyclic cycloalkyl. For example, in certain particular embodiments, each cycloalkyl recited in any one of the preceding embodiments is a cyclopropyl, a cyclobutyl, a cyclopentyl, a cyclopentenyl, a cyclohexyl or a cyclohexenyl.

In certain additional embodiments, including any of the embodiments described with reference to formulae (I)-(I-6) and embodiments disclosed above, each heterocycloalkyl recited in any one of the preceding embodiments is a 4-7 membered monocyclic heterocycloalkyl having 1-2 heteroatoms selected from O, S and N. For example, in certain particular embodiments, each heterocycloalkyl recited in any one of the preceding embodiments is a pyrrolidinyl, a tetrahydrofuranyl, a tetrahydrothienyl, a piperidinyl, a piperazinyl, a morpholinyl, a thiomorpholinyl, a tetrahydro-2H-pyranyl, or a tetrahydro-2H-thiopyranyl. In certain particular embodiments, each heterocycloalkyl recited in any one of the preceding embodiments is a pyrrolidine, a piperidine, a piperazine, a tetrahydrofuran, a (1H)dihydropyran, or a morpholine.

In certain additional embodiments, including any of the embodiments described with reference to formulae (I)-(I-6) and embodiments disclosed above, each aryl is phenyl.

In certain additional embodiments, including any of the embodiments described with reference to formulae (I)-(I-6) and embodiments disclosed above, each heteroaryl is a 5-6 membered monocyclic heteroaryl having 1-3 heteroatoms selected from O, S and N. For example, in certain particular embodiments, each heteroaryl is a monocyclic heteroaryl. In certain particular embodiments, each heteroaryl is a furanyl, a thienyl, a pyrrolyl, a pyrazolyl, an imidazolyl, an oxazolyl or a thiazolyl.

Therapeutics Applications

The disclosure also provides methods of treating cancer. Such method includes administering to a subject in need of such treatment an effective amount of one or more compounds of the disclosure as described herein or a pharmaceutical composition of the disclosure as described herein.

Many different cancers can be treated with compounds and compositions of the disclosure. Particularly suitable cancers are BRAF-mutant cancers and their metastasis. In certain embodiments, the cancer is melanoma, brain cancer, colorectal cancers, lung cancer, breast cancer, head and neck tumors, and lymphoma. In certain embodiments, the cancer is glioblastoma multiforme or BRAF-mutant glioblastoma. In certain embodiments, the cancer develops in peripheral tissues and metastasizes to the brain.

In certain embodiments, the cancer is glioblastoma comprising PAD-7$^{mut}$. In certain embodiments, the cancer is glioblastoma comprising one or more phenotypes of GBM8 glioblastoma cells.

Other examples of cancers include, but are not limited to, carcinomas, sarcomas, and astrocytomas. In certain embodiments, the cancer is breast cancer, prostate cancer, lung cancer (e.g., small-cell lung carcinoma (SCLC) and non-small-cell lung carcinoma (NSCLC)), gastric cancer, colorectal cancer, cervical cancer, endometrial cancer, ovarian cancer, skin cancer (e.g., basal-cell skin cancer (BCC), squamous-cell skin cancer (SCC), and melanoma), pancreatic cancer, kidney cancer, adrenal gland cancer, sarcoma, thyroid cancer, cholangiocarcinoma, glioblastoma, astrocytoma, oligodendroglioma, high-grade glioma, malignant glioma, glioma, neuroblastoma, leukemia or lymphoma. Suitable cancers also include a hematological malignancy, such as leukemia or lymphoma. In certain embodiments, the cancer is acute myeloid leukemia (AML), chronic myeloid leukemia (CML), acute lymphoblastic leukemia (ALL), chronic lymphocytic leukemia (CLL), or lymphoma.

The compounds and compositions of the disclosure as described herein may also be administered in combination with one or more secondary therapeutic agents. Thus, in certain embodiment, the method also includes administering to a subject in need of such treatment an effective amount of one or more compounds of the disclosure as described herein (e.g., compounds of formula (I)-(I-6) or compounds 8, 9, 10, 11, 12, 13, 14, 16, 18, 20, 22, 23, 24, 25, 26, 28, 31, or 35) or a pharmaceutical composition of the disclosure as described herein and one or more secondary therapeutic agents.

"Combination therapy," in defining use of a compound of the present disclosure and another therapeutic agent, is intended to embrace administration of each agent in a sequential manner in a regimen that will provide beneficial effects of the drug combination (e.g., the compounds and compositions of the disclosure as described herein and the secondary therapeutic agents can be formulated as separate compositions that are given sequentially), and is intended as well to embrace co-administration of these agents in a substantially simultaneous manner, such as in a single capsule having a fixed ratio of these active agents or in multiple or a separate capsules for each agent. The disclosure is not limited in the sequence of administration: the compounds of and compositions of the disclosure may be administered either prior to or after (i.e., sequentially), or at the same time (i.e., simultaneously) as administration of the secondary therapeutic agent.

In certain embodiments, the secondary therapeutic agent may be administered in an amount below its established half maximal inhibitory concentration ($IC_{50}$). For example, the secondary therapeutic agent may be administered in an amount less than 1% of, e.g., less than 10%, or less than 25%, or less than 50%, or less than 75%, or even less than 90% of the inhibitory concentration ($IC_{50}$).

In certain embodiments, the secondary therapeutic agents includes one or more of temozolomide (Temodar®), camptothecin, doxorubicin, daunorubicin, vincristine, paclitaxel, vemurafenib (PLX4032, Zelboraf®), fluorouracil (5-FU), neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, chloroquine, hydroxychloroquine, autophagy inhibitors, abt-737, leucovorin, psilocybin, netupitant, palonosetron, aprepitant, 3,4-methylenedioxymethamphetamine, nicotine, ketamine, lithium salt (e.g., lithium citrate), valproic acid, bevacizumab, bortezomib, gemcitabine, irinotecan, oxaliplatin, adalimumab, azathioprine, infliximab, citalopram, mirtazapine, sertraline, esketamine, fluoxetine, paroxetine, venlafaxine, fenfluramine, vigabatrin, clobazam, stiripentol, cyclosporine, tacrolimus, methylprednisolone, megestrol acetate, biguanide (e.g., metformin), and sulphonyl urea (e.g., glipizide, tolbutamide).

In certain embodiments, the method includes administering to a subject in need of such treatment an effective amount of one or more compounds of the disclosure as described herein (e.g., (e.g., compound 8, 9, 10, 11, 12, 13, 14, 16, 18, 19, 20, 22, 23, 24, 25, 26, 28, 31, or 35 or any of compounds of formula (I)-(I-6)) or a pharmaceutical composition of the disclosure as described herein and one or more secondary therapeutic agents selected from paclitaxel, vemurafenib, and fluorouracil. In certain embodiments, the method includes administering the one or more compounds of the disclosure and paclitaxel. In certain embodiments, the method includes administering the one or more compounds of the disclosure and vemurafenib. In certain embodiments, the method includes administering the one or more compounds of the disclosure and fluorouracil. In certain embodiments of this method, the paclitaxel, vemurafenib, or fluorouracil is administered in an amount below its established $IC_{50}$; e.g., in an amount less than 1% of, e.g., less than 10%, or less than 25%, or less than 50%, or less than 75%, or even less than 90% of the $IC_{50}$.

In certain embodiments, a composition provided herein is conjointly administered with a suitable secondary therapeutic agent which is a chemotherapeutic agent. Suitable chemotherapeutic agents may include, natural products such as vinca alkaloids (e.g., vinblastine, vincristine, vindesine, vinflunine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P 1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS I (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., FNK128), kinase inhibitor (e.g., GS-1 101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

There are large numbers of antineoplastic agents available in commercial use, in clinical evaluation and in pre-clinical development, which would be selected for treatment of neoplasia by combination therapy. Thus, in certain embodiments, the method also includes administering to a subject in need of such treatment an effective amount of one or more compounds of the disclosure as described herein (e.g., compounds of formula (I)) or a pharmaceutical composition thereof and one or more secondary therapeutic agents selected from antineoplastic agents. In general antineoplastic agents fall into several major categories, namely, antibiotic-type agents, alkylating agents, antimetabolite agents, hormonal agents, immunological agents, interferon-type agents and a category of miscellaneous agents. Suitable antineoplastic agents, in certain embodiments, may include, alkylating agents, antimetabolites, anthracyclines, topoisomerase inhibitors, B-raf enzyme inhibitors and microtubule inhibitors.

A family of antineoplastic agents which may be used in combination with compounds of the present disclosure consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol. Alkylating agents include the nitrogen mustards (such as mechlorethamine, cyclophosphamide, ifosfamide, melphalan and chlorambucil), ethylenamine and methylenamine derivatives (such as altretamine, thiotepa), alkyl sulfonates (such as busulfan), nitrosoureas (such as carmustine, lomustine, estramustine), triazenes (such as dacarbazine, procarbazine, temozolomide), and platinum-containing antineoplastic agents (such as cisplatin, carboplatin, oxaliplatin).

A family of antineoplastic agents which may be used in combination with compounds of the present disclosure consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin. Antimetabolites include 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate, Pemetrexed (Alimta®).

A family of antineoplastic agents which may be used in combination with compounds of the present disclosure includes miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

A family of antineoplastic agents which may be used in combination with compounds of the present disclosure includes B-raf enzyme inhibitors such as vemurafenib (Zelboraf®) dabrafenib (Tafinlar®), and encorafenib (Braftovi®).

A family of antineoplastic agents which may be used in combination with compounds of the present disclosure consists of antibiotic-type antineoplastic agents. Suitable antibiotic-type antineoplastic agents may be selected from but not limited to the group consisting of Taiho 4181-A, aclarubicin, actinomycin D, mitomycin-C, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin (Adriamycin®), doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Alternatively, the compounds of the disclosure may also be used in combination therapy with other antineoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105 AD7 MAb (CRC Technology), idiotypic CEA MAb (Trilex), LYM-1-iodine 131 Mab (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors, TNF inhibitors, metallomatrix proteases inhibitors (MMP) and VEGFR inhibitors.

In one aspect, the disclosure provides a method where the additional therapeutic agent is an immune activating agent, i.e. a therapeutic that activates the immune response. Examples include checkpoint inhibitors, co-activating receptor agonists, and cancer-focused or pathogen-focused vaccines.

The compounds or the pharmaceutical compositions of the disclosure as described herein may also be used in combination with radiation therapy, hormone therapy, surgery and immunotherapy, which therapies are well known to those skilled in the art.

The disclosure also provides methods of disrupting MT function in a cell. Such methods include administering one or more compounds of the disclosure to the cell. Disrupting MT function may include binding tubulin with the compound of the disclosure, or disrupting MT function may include treating melanocytes expressing BRAF mutants with the compound of the disclosure.

The disclosure also provides methods of killing cancer cells. Such methods include administering one or more compounds of the disclosure to the cell. The cell killing profile may include $EC_{50}$ of between 100 nm and 1 μM in PD-GBM (proneural) assay, $EC_{50}$ of between 200 nm and 1.5 μM in PD-GBM (classical) assay, and/or $EC_{50}$ of between 100 nm and 2.5 μM in PD-GBM (mesenchymal) assay. In certain embodiments, the cell killing profile may include $EC_{50}$ of between 316 and 542 nM in PD-GBM (proneural) assay, $EC_{50}$ of between 407 and 846 nM in PD-GBM (classical) assay, and $EC_{50}$ of between 268 and 1823 nM in PD-GBM (mesenchymal) assay.

Another aspect of the disclosure provides a method of treating diseases associated with $CB_1$ receptor and/or $CB_2$ receptor, in a subject in need thereof. Such method includes administering one or more compounds of the disclosure as described herein (e.g., compounds of formula (I)-(I-6) or compounds 8, 9, 10, 11, 12, 13, 14, 16, 18, 20, 22, 23, 24, 25, 26, 28, 31, or 35) or a pharmaceutical composition of the disclosure as described herein. Such diseases include, but are not limited to attention-deficit/hyperactivity disorder (ADHD)/attention-deficit disorder (ADD), alcohol use disorder, allergic asthma, amyotrophic lateral sclerosis (ALS), Alzheimer's, anorexia (e.g. human immunodeficiency virus (HIV)-related cachexia), anxiety disorders (e.g., social anxiety disorder, specific phobia, test anxiety, generalized anxiety disorder), autism, bipolar disorder, cancer pain, Charcot-Marie-Tooth disease, chronic inflammatory demyelinating polyneuropathies, chronic pain, cocaine use disorder, complex regional pain syndrome, depression, fibromyalgia, fragile X syndrome/fragile X-associated tremor and ataxia syndrome (FXTAS), frontotemporal dementias (behavioral variant), glaucoma, glioblastoma, Huntington's disease, inflammatory bowel disease (IBD)/irritable bowel syndrome (IBS), inflammatory myopathies, leukodystrophies, migraine, multiple sclerosis, nausea (e.g. chemotherapy-induced nausea and vomiting (CINV), motion sickness), neuropathic pain (e.g., postherpetic neuralgia, painful diabetic neuropathy), nightmare disorder, non-alcoholic fatty liver disease, obesity, obsessive-compulsive disorder, opioid sparing, opioid use disorder, osteoarthritis, osteoporosis, Parkinson's, post-concussion syndrome/traumatic brain injury, psychosis/schizophrenia, posttraumatic stress disorder (PTSD), rapid eye movement (REM) sleep behavior disorder, Rett syndrome, rheumatoid arthritis, skin conditions (e.g. acne, psoriatic arthritis), sleep disorders (e.g., insomnia, restless legs syndrome (RLS)), spinocerebellar ataxias, tobacco use disorder/nicotine dependence, Tourette's, trigeminal neuralgia, and epilepsies. In certain embodiments, the disease associated with $CB_1$ receptor and/or $CB_2$ receptor is ADHD/ADD, alcohol use disorder, allergic asthma, ALS, Alzheimer's, autism, cancer pain, Charcot-Marie-Tooth disease, chronic inflammatory demyelinating polyneuropathies, chronic pain, complex regional pain syndrome, fibromyalgia, fragile X syndrome/FXTAS, frontotemporal dementias (behavioral variant), glioblastoma, Huntington's disease, IBD/IBS, inflammatory myopathies, migraine, multiple sclerosis, neuropathic pain (e.g., postherpetic neuralgia, painful diabetic neuropathy), non-alcoholic fatty liver disease, opioid sparing, opioid use disorder, osteoarthritis, osteoporosis, Parkinson's, post-concussion syndrome/traumatic brain injury, Rett syndrome, rheumatoid arthritis, skin condition (e.g. acne, psoriatic arthritis), spinocerebellar ataxias, Tourette's, trigeminal neuralgia, and epilepsy.

Pharmaceutical Compositions

In another aspect, the present disclosure provides compositions comprising one or more of compounds as described herein (e.g., a compound of formula (I) or Table 1) and an appropriate carrier, solvent, adjuvant, or diluent. The exact nature of the carrier, solvent, adjuvant, or diluent will depend upon the desired use for the composition, and may range from being suitable or acceptable for veterinary uses to being suitable or acceptable for human use. The composition may optionally include one or more secondary therapeutic agents. In certain embodiments, the composition may include one or more secondary anticancer therapeutic agents.

When used to treat or prevent such diseases, the compounds described herein may be administered singly, as mixtures of one or more compounds or in mixture or combination with other secondary agents as described above useful for treating such diseases and/or the symptoms associated with such diseases.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

In some embodiments, the pharmaceutical composition is formulated for oral administration once a day or QD, and in some such formulations is a unit where the effective amount of the active ingredient ranges from 50 mg to 5000 mg. Alternatively, an oral solution may be provided ranging from a concentration of 1 mg/ml to 50 mg/ml or higher.

One aspect of the disclosure includes administering a compound of the disclosure to provide a serum concentration ranging from 0.1 µM to 50 µM. One aspect of the disclosure includes administering a compound of the disclosure to provide a serum concentration ranging from 1 µM to 20 µM. One aspect of the disclosure includes administering a compound of the disclosure to provide a serum concentration ranging from 5 µM to 20 µM. One aspect of the disclosure includes administering a compound of the disclosure to provide a serum concentration of 10 µM, 20 µM, 5 µM, 1 µM, 15 µM, or 40 µM.

One aspect of the disclosure includes administering a compound of the disclosure at a dose of 1 to 100 mg/kg/day, 5-40 mg/kg/day, 10-20 mg/kg/day, 1-2 mg/kg/day, 20-40 mg/kg/day, 45-50 mg/kg/day, 50-60 mg/kg/day, 55-65 mg/kg/day, 60-70 mg/kg/day or 65-75 mg/kg/day.

As one aspect of the present disclosure contemplates the treatment of the disease/conditions with the compounds of the disclosure, the disclosure further relates to pharmaceutical compositions in kit form. When the composition of the disclosure is a part of a combination therapy with a secondary therapeutic agent, the kit may comprise two separate pharmaceutical compositions: one of compound of the present disclosure, and another of a second therapeutic agent. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Definitions

The following terms and expressions used herein have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)—O—$C_1$-$C_6$alkyl indicate the same functionality; similarly arylalkyl and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)$_a$, wherein a is 0 or 1. In such instances, when a is 0 the moiety is —B and when a is 1 the moiety is —B-A.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, and —CH$_2$CH(CH$_2$CH$_3$)CH$_2$—.

The term "alkylene" refers to a bivalent alkyl group. In certain embodiments, an "alkylene chain" is a polymethylene group, i.e., —(CH$_2$)$_n$—, wherein n is a positive integer, preferably from one to six, from one to four, from one to three, from one to two, or from two to three. A substituted alkylene chain is a bivalent alkyl group in which one or more hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thioxo.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thioxo. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thioxo.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl, a bicyclic ring, or a tricyclic ring system containing at least one heteroaromatic ring. In certain embodiments, the heteroaryl is a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The tricyclic heteroaryl consists of a monocyclic heteroaryl fused to two rings selected from a phenyl, a monocyclic cycloalkyl, a monocyclic cycloalkenyl, a monocyclic heterocyclyl, and a monocyclic heteroaryl. The fused cycloalkyl or heterocyclyl portion of the bicyclic heteroaryl group is optionally substituted with one or two groups which are independently oxo or thioxo. When the bicyclic or tricyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, 2,3-dihydrothieno[3,4-b][1,4]dioxan-5-yl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thioxo.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thioxo. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thioxo.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thioxo" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts. These salts can be prepared in situ during the final isolation and purification of a compound provided herein, or by separately reacting the compound in its free base form with a suitable organic or inorganic acid and isolating the salt thus formed. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Additional examples of pharmaceutically acceptable salts are provided in Berge et al. "Pharmaceutical Salts", *J. Pharm. Sci.* 66: 1-19 (1977).

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

The term "prodrug" means compounds that are transformed in vivo to yield a compound of the present disclosure. The transformation may occur by various mechanisms, such as through hydrolysis in blood. A discussion of the use of prodrugs is provided by Higuchi and Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. To illustrate, for example, if a compound of the present disclosure comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O—$C_1$-$C_6$ alkyl)$_2$ or glycosyl (the radical resulting from the removal of a hydroxyl group of the hemiacetal form of a carbohydrate).

As used herein, chemical structures which contain one or more stereocenters depicted with dashed and bold bonds (i.e., and —) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers. Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

As used herein and unless otherwise indicated, the term "stereoisomer" or"stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule. As described above, this disclosure encompasses the use of stereomerically pure forms of such compounds, as well as the use of mixtures of those forms. For example, mixtures comprising equal or unequal amounts of the enantiomers of a particular compound of the disclosure may be used in methods and compositions of the disclosure. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

The compounds of the disclosure may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the disclosure, whether radioactive or not, are intended to be encompassed within the scope of the disclosure. For example, if a variable is said or shown to be H, this means that variable may also be deuterium (D) or tritium (T).

The compounds disclosed herein include all pharmaceutically acceptable isotope-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotope-labeled compounds of the disclosure, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotope-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotope-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed. E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-4, general procedures (below), and/or analogous synthetic procedures. One of skill in the art can adapt the reaction sequences of Schemes 1-4, general procedures, and Examples 1-33 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

The route for the synthesis of several compounds of the disclosure is outlined in Scheme 1. For example, compounds 8, 10, 11, 12, 13, 14, 16, 17, 25 and 31 were prepared from commercially available carbazoles via consecutive substitution with the corresponding n-alkyl bromide under alkaline conditions, followed by a Friedel-Crafts reaction using the corresponding acyl chloride derivatives as illustrated in Scheme 1.

Scheme 1

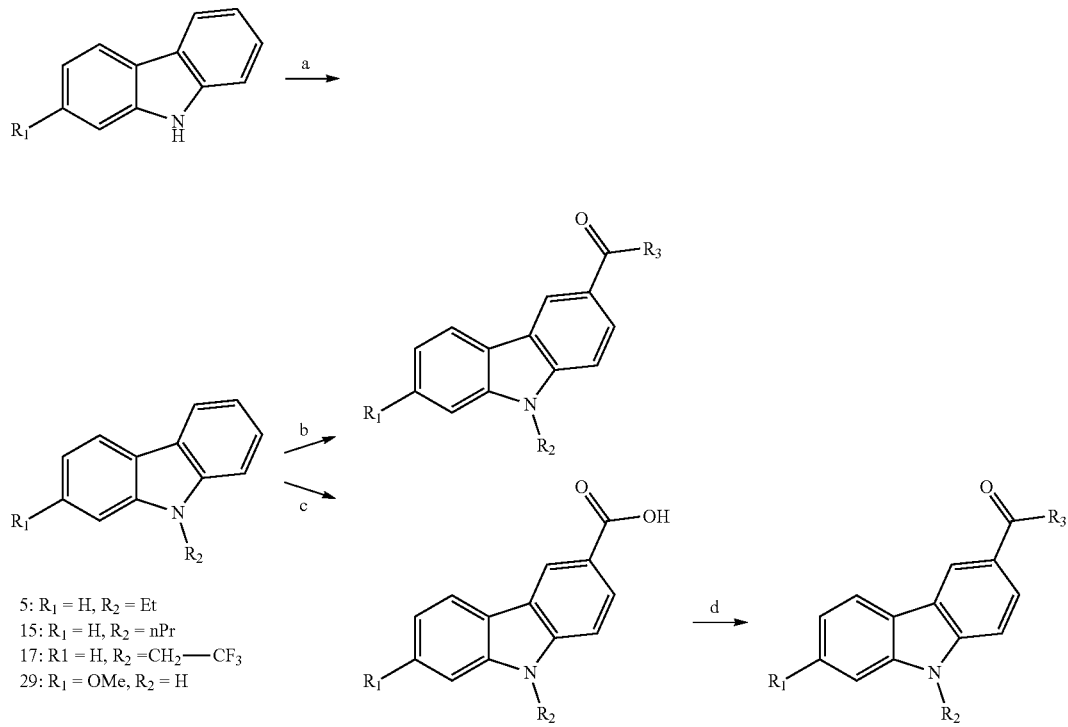

5: R₁ = H, R₂ = Et
15: R₁ = H, R₂ = nPr
17: R1 = H, R₂ = CH₂—CF₃
29: R₁ = OMe, R₂ = H

Reagents and conditons: a. Cs₂CO₃, alkylbromide, DMF, room temperature; b. acyl chloride, AlCl₃, benzene 0° C. to room temperature; c. i. POCl₃, DMF, μW, 1 h, 100° C.; ii. KMnO₄, water/acetone, reflux; d. EDC, DMAP, DIPEA, amine, DMF.

Reagents and conditions: a. $Cs_2CO_3$, alkylbromide, DMF, room temperature; b. acyl chloride, $AlCl_3$, benzene 0° C. to room temperature; c. i. $POCl_3$, DMF, μW, 1 h, 100° C.; ii. $KMnO_4$, water/acetone, reflux; d. EDC, DMAP, DIPEA, amine, DMF.

8: $R_1$=H, $R_2$=ethyl, $R_3$=4-methylnaphthalenyl
9: $R_1$=H, $R_2$=ethyl, $R_3$=4-methylpiperazinyl
10: $R_1$=H, $R_2$=ethyl, $R_3$=4-chlorophenyl
11: $R_1$=H, $R_2$=ethyl, $R_3$=4-fluorophenyl
12: $R_1$=H, $R_2$=ethyl, $R_3$=p-tolyl
13: $R_1$=H, $R_2$=ethyl, $R_3$=methylbenzene
14: $R_1$=H, $R_2$=ethyl, $R_3$=naphthalenyl
16: $R_1$=H, $R_2$=propyl, $R_3$=4-methylnaphthalenyl
17: $R_1$=H, $R_2$=2,2,2-trifluoroethyl, $R_3$=4-methylnaphthalenyl
31: $R_1$=MeO—, $R_2$=ethyl, $R_3$=4-methylnaphthalenyl Carbazole 28 was obtained by alkylation of carbazole with 4-methylnaphthalene-1-carbonyl chloride under basic conditions. As provided in Scheme 2, bromine-lithium exchange of bromo-carbazole derivative (t-BuLi, −78° C.), followed by the addition of quinolone aldehyde derivatives, furnished the corresponding alcohols, 19 and 21, which were oxidized to form 20 and 22. Quinoline derivatives 23 and 24 were conveniently prepared after reduction of compounds 20 and 22, respectively.

Scheme 2

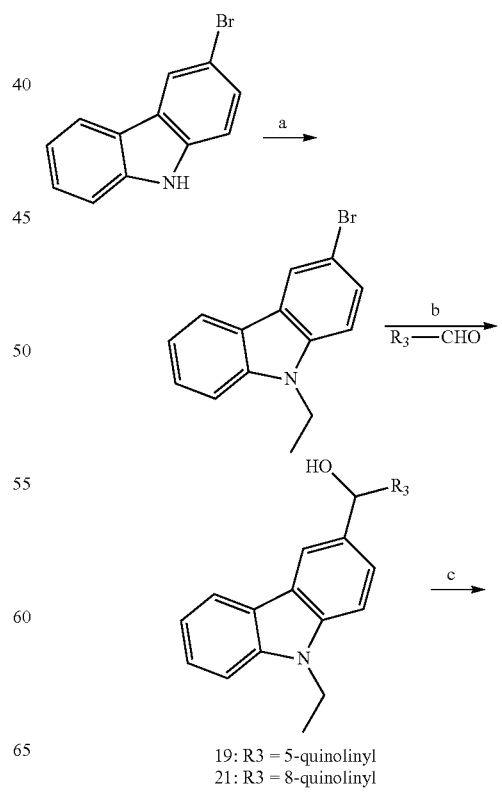

19: R3 = 5-quinolinyl
21: R3 = 8-quinolinyl

-continued

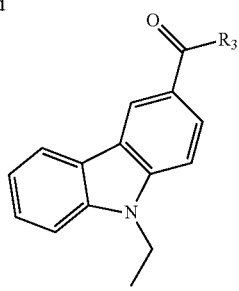

20: R3 = 5-quinolinyl
22: R3 = 8-quinolinyl

Reagents and conditions: a. Cs₂CO₃, ethylbromide, DMF; b. t-BuLi, THF, -78 to 0° C.; c. PDC, CH₂Cl₂, molecular sieves room temperature Reagents and conditions: a. Cs₂CO₃, ethylbromide, DMF; b. t-BuLi, THF, −78 to 0° C.; c. PDC, CH₂Cl₂, molecular sieves room temperature As provided in Scheme 3, compounds 26 and 27 were obtained by heating amide 8 with Lawesson's reagent under microwave conditions and by reducing its carbonyl with NaBH₄, respectively.

Reagents and conditions: a. Lawesson's reagent, toluene; b. NaBH₄, MeOH.

Compound 35 was prepared from phenylhydrazine and ethyl-4-oxocyclohexanecarboxylate as provided in Scheme 4.

Scheme 4

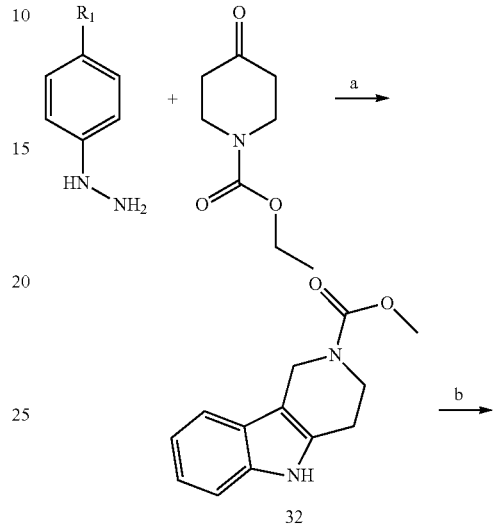

Scheme 3

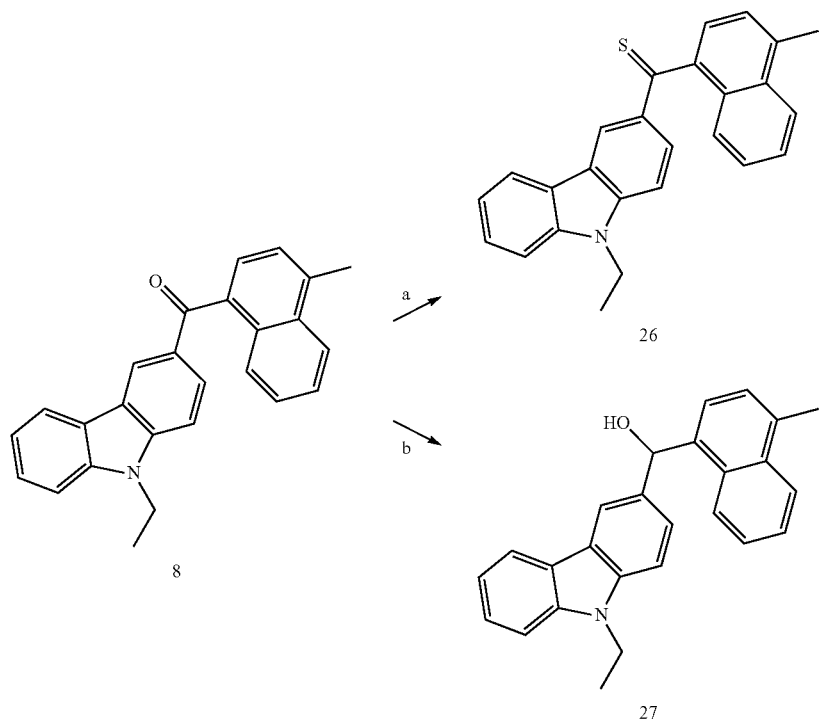

Reagents and conditions: a. Lawesson's reagent, toluene; b. NaBH₄, MeOH.

41

-continued

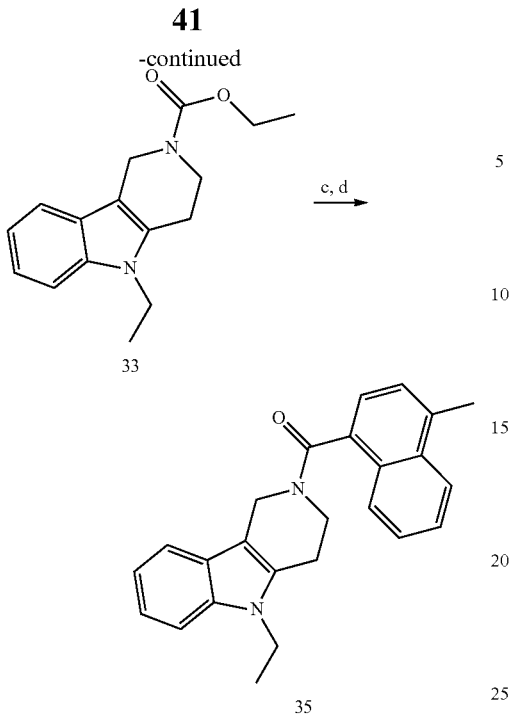

Reagents and conditions: a. HCl, EtOH; b. NaH, alkylbromide, DMF;
c. KOH, H₂O, EtOH, reflux; d. EDC, DMAP, DIPEA, amine, DMF,
35: R₁ = H, R₂ = ethyl, R₃ = 4-methylnaphthalenyl Reagents and conditions: a. HCl, EtOH; b. NaH, alkylbromide, DMF; c. KOH, H₂O, EtOH, reflux; d. EDC, DMAP, DIPEA, amine, DMF.

35: $R_1$=H, $R_2$=ethyl, $R_3$=4-methylnaphthalenyl

EXAMPLES

The preparation of the compounds of the disclosure is illustrated further by the following examples, which are not to be construed as limiting the disclosure in scope or spirit to the specific procedures and compounds described in them.

Example 1: 9-ethyl-9H-carbazole (5)

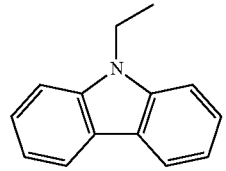

Under argon, a solution of carbazole (5.0 g, 29.9 mmol), bromoethane (4.45 mL, 35.9 mmol), and Cs₂CO₃ (14.6 g, 44.8 mmol) in dimethylformamide (20 mL) was stirred at 80° C. for 16 hours. The reaction mixture was cooled, diluted with ethyl acetate (50 mL), and filtered. The organic solvents were evaporated in vacuo. The resultant dark oil was purified by column chromatography on silica gel using heptanes/ethyl acetate in different proportions to afford the title compound as a light-yellow oil (5.075 g, 87%). ¹H NMR (500 MHz, CDCl₃) δ ppm 8.18 (d, J=7.79 Hz, 2H), 7.54 (t, J=7.66 Hz, 2H), 7.46 (d, J=8.06 Hz, 2H), 7.26-7.35 (m, 2H), 4.40 (q, J=7.25 Hz, 3H), 1.41-1.52 (m, 3H)¹³C NMR (126 MHz, CDCl₃) δ ppm 139.85, 125.54, 122.85, 120.37, 118.68, 108.37, 37.42, 13.75.

Example 2: 9-ethyl-9H-carbazole-3-carbaldehyde (6)

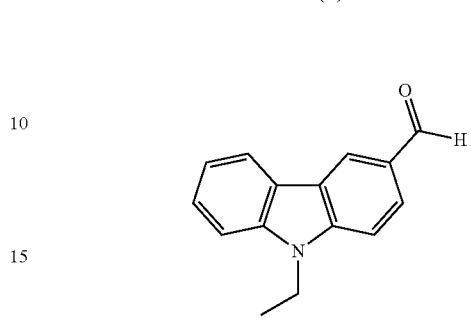

POCl₃ (1.4 mL, 10.2 mmol) was added, over a period of 10 min, to ice-cooled, stirred dimethylformamide (3.2 mL, 40.8 mmol) under argon. The reddish solution was stirred at room temperature for 1 hour. 9-ethyl-9H-carbazole 5 (1.0 g, 5.1 mmol) was added over 10 min, and the mixture was subjected to microwave irradiation at 100° C. for 1 hour. The reaction mixture was cooled and then poured into crushed ice. After warming to room temperature, the resultant product was extracted with ethyl acetate. The organic phase was washed with water, and brine, dried (MgSO₄), filtered, and evaporated in vacuo. The residue was purified by column chromatography on silica gel using heptanes/ethyl acetate in different proportions to afford the title compound as a white solid (1.054 g, 93%); ¹H NMR (400 MHz, CDCl₃) δ ppm 10.03 (s, 1H), 8.57 (s, 1H), 8.12 (d, J=7.7 Hz, 1H), 7.94 (d, J=8.5 Hz, 1H), 7.52 (t, J=7.6 Hz, 1H), 7.41 (d, J=8.6 Hz, 2H), 7.30 (t, J=7.4 Hz, 1H), 4.26 (t, J=7.2 Hz, 2H), 1.45 (t, J=7.2 Hz, 3H). ¹³C NMR (101 MHz, CDCl₃) δ ppm 191.83, 144.18, 141.27, 128.56, 127.23, 126.82, 124.06, 123.14, 123.08, 120.84, 120.40, 109.53, 109.05, 42.76, 13.91.

Example 3: 9-ethyl-9H-carbazole-3-carboxylic acid (7)

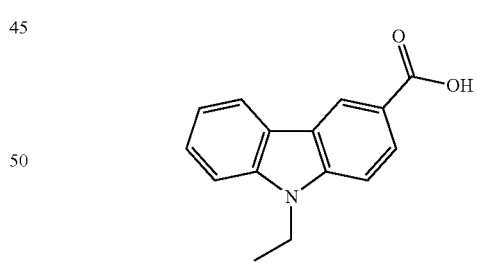

To an ice-cold solution of 9-ethyl-3-carbaldehyde 6 (1.0 g, 4.5 mmol) in water/acetone (50 mL, 1:1) was added dropwise with stirring a solution of potassium permanganate (711 mg, 4.5 mmol) in acetone (25 mL). The mixture was heated 3 hours at reflux and then allowed to cool to room temperature. After that, the reaction mixture was quenched with ethanol (20 mL) and then stirred for 30 min at reflux. After cooling to room temperature, the mixture was filtered through a pad of Celite© and concentrated in vacuo. The concentrated solution was diluted with water (100 mL), basified with NaOH to pH ca. 10, and extracted with heptane/ether (4:1, 50 mL×3) to remove the unreacted starting material. The aqueous solution was cooled on an ice-water bath and then acidified with an ice-cold solution of 2 N HCl to pH ca. 2. The resultant precipitate was extracted with ethyl acetate (150 mL). The organic layer was washed with brine (30 mL), dried over MgSO$_4$, filtered, and concentrated in vacuo. The precipitated product was collected by filtration, washed with heptanes (20 mL), and dried overnight to produce the title compound 7 (527.2 mg, 49%) as a yellow oil; $^1$H NMR (500 MHz, CDCl$_3$) δ ppm 12.34 (s, 1H), 8.89 (d, J=1.6 Hz, 1H), 8.31 (dd, J=8.6, 1.6 Hz, 1H), 8.12 (d, J=7.7 Hz, 1H), 7.51 (ddd, J=8.3, 7.1, 1.3 Hz, 1H), 7.37 (d, J=8.2 Hz, 1H), 7.34 (d, J=8.7 Hz, 1H), 7.28 (ddd, 7.9, 6.9, 1 Hz, 1H), 4.32 (t, J=7.2 Hz, 2H), 1.45 (t, J=7.2 Hz, 3H). $^{13}$C NMR (126 MHz, CDCl$_3$) δ ppm 173.30, 143.47, 141.17, 128.13, 126.62, 123.87, 123.14, 122.67, 120.88, 120.33, 119.82, 109.34, 108.45, 42.57, 14.01.

Example 4: 9-ethyl-3-[(4-methylnaphthalen-1-yl)carbonyl]-9H-carbazole (8)

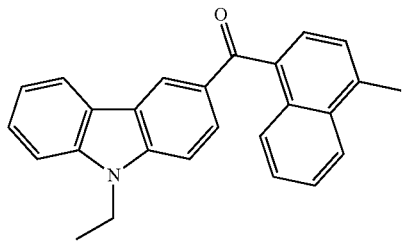 [SMILES: CCn1c2ccccc2c2cc(C(=O)c3ccc(C)c4ccccc34)ccc21]

Under argon, AlCl$_3$ (199 mg, 1.5 mmol) was added to a solution of 9-ethyl-9H-carbazole 7 (300 mg, 1.25 mmol) in anhydrous benzene (30 mL), and the solution was cooled by an ice bath for 20 min. 4-methyl-1-naphthoyl chloride (282 mL, 2.43 mmol) was added dropwise via a syringe to the solution, and the reaction mixture was stirred for 16 hours while warming at room temperature. The reaction mixture was cooled on an ice-water bath, then poured onto a mixture of ice and a 4 M NaOH solution (50 mL) and extracted with ethyl acetate (150 mL). The obtained residue was purified by column chromatography on silica gel eluting with ethyl acetate/heptanes in different proportions to yield the target product (296.3 mg, 64%) as a light yellow solid: $^1$H NMR (400 MHz, CDCl$_3$) δ ppm 8.63 (s, 1H), 8.00-8.18 (m, 4H), 7.37-7.61 (m, 7H), 7.24-7.27 (m, 1H), 4.41 (q, J=7.28 Hz, 2H), 2.81 (s, 3H), 1.47 (t, J=7.28 Hz, 3H). $^{13}$C NMR (101 MHz, CDCl$_3$) δ ppm 197.9, 142.9, 140.7, 137.3, 136.2, 132.9, 131.3, 129.8, 128.6, 126.9, 126.6, 126.6, 126.5, 126.2, 125.3, 124.4, 124.3, 123.3, 122.7, 120.9, 120.0, 109.0, 108.1, 37.9, 19.9, 13.9. HRMS calculated for C$_{26}$H$_{22}$NO (M+H)$^+$: 364.1684, found HRMS: 364.1701.

Example 5: 9-ethyl-3-(4-methylpiperazine-1-carbonyl)-9H-carbazole (9)

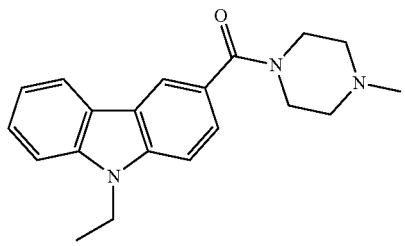 [SMILES: CCn1c2ccccc2c2cc(C(=O)N3CCN(C)CC3)ccc21]

9-ethyl-9H-carbazole-3-carboxylic acid 7 (200 mg, 0.84 mmol), 1-methylpiperazine (171 mg, 1.29 mmol), N,N-diisopropylethylamine (DIPEA) (284 μL, 1.7 mmol), and 4-dimethylaminopyridine (DMAP) (122 mg, 1 mmol) were added to dichloromethane (26 mL) under N$_2$. The obtained solution was cooled on an ice-water bath. 1-Ethyl-3-(3-dimethylaminopropyl)carbodiimide (EDC) (275 mg, 1.44 mmol) was added to the solution, and the reaction mixture was then allowed to warm to room temperature and stirred for 16 hour. The solvent was removed in vacuo, and the obtained residue was extracted into ethyl acetate (100 mL). The organic layer was washed consecutively with 5% citric acid solution (50 mL×3), concentrated NaHCO$_3$ (50 mL×3), brine (50 mL), dried over MgSO$_4$, filtered, and concentrated in vacuo. The residue was purified on silica gel using heptanes/ethyl acetate in different proportions to afford 199 mg (74%) of 9 as a yellow glass. $^1$H NMR (400 MHz, CDCl$_3$) δ ppm 8.24 (s, 1H), 8.10 (d, J=7.45 Hz, 1H), 7.50-7.59 (m, 2H), 7.41-7.48 (m, 2H), 7.29 (t, J=7.53 Hz, 1H), 4.40 (q, J=7.19 Hz, 2H), 3.72 (br s, 1H), 2.52 (br s, 1H), 2.44 (s, 3H), 2.17 (s, 1H), 1.40-1.49 (m, 4H). $^{13}$C NMR (101 MHz, CDCl$_3$) δ ppm 167.78, 141.17, 140.49, 126.63, 125.27, 122.83, 122.51, 120.72, 120.66, 119.79, 108.93, 108.46, 53.47, 43.58, 37.79, 26.89, 13.78. HRMS calculated for C$_{20}$H$_{24}$N$_3$O (M+H)$^+$: 322.1913, found: 322.1952.

Example 6: 3-(4-chlorobenzoyl)-9-ethyl-9H-carbazole (10)

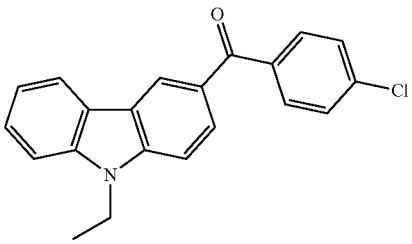 [SMILES: CCn1c2ccccc2c2cc(C(=O)c3ccc(Cl)cc3)ccc21]

Under argon, AlCl$_3$ (1.13 g, 8.44 mmol) was added to a solution of 5 (1.5 g, 7.68 mmol) in anhydrous benzene (20 mL), and the solution was cooled by an ice bath for 20 min. 4-chlorobenzoic acid (1.12 mL, 8.83 mmol) was added dropwise via a syringe to the solution, which was tightly capped in a microwave vessel and subjected to microwave irradiation at 100° C. for 1 hour and then cooled to room temperature. The reaction mixture was cooled on an ice-water bath, then poured onto a mixture of ice and a 4 M NaOH solution (50 mL) and extracted with ethyl acetate (150 mL). The organic phase was washed with saturated aqueous NaHCO$_3$ and brine, dried (MgSO$_4$), filtered and evaporated in vacuo. The residue was purified by column chromatography on silica gel eluting with ethyl acetate/heptanes in different proportions to yield the target product (1.374 g, 54%) as a white solid: $^1$H NMR (400 MHz, CDCl$_3$) δ ppm 8.63 (d, J=1.30 Hz, 1H), 8.16 (d, J=7.77 Hz, 1H), 8.04 (dd, J=8.58, 1.67 Hz, 1H), 7.87-7.98 (m, 2H), 7.56 (td, J=7.64, 1.03 Hz, 1H), 7.45-7.53 (m, 2H), 7.29-7.37 (m, 1H), 7.17-7.28 (m, 2H), 4.43 (q, J=7.23 Hz, 2H), 1.51 (t, J=7.23 Hz, 3H). $^{13}$C NMR (101 MHz, CDCl$_3$) δ ppm 195.06, 166.11, 163.60, 142.43, 140.57, 135.12, 135.09, 132.36, 132.28, 128.25, 128.22, 126.46, 123.76, 123.04, 122.51, 120.68, 119.92, 115.30, 115.08, 108.95, 107.99, 37.75, 13.74. ESI: m/z 334.1 (M+H)⁺. HRMS calculated for $C_{21}H_{17}ClNO$ (M+H)⁺ 334.0999, found 334.0981.

Example 7: 9-ethyl-3-(4-fluorobenzoyl)-9H-carbazole (11)

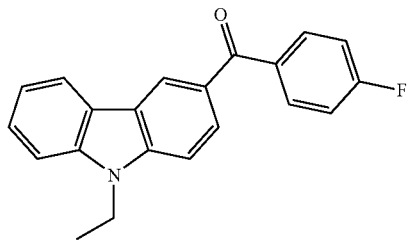 [SMILES: CCn1c2ccccc2c2cc(C(=O)c3ccc(F)cc3)ccc21]

Using 9-ethyl-9H-carbazole 5 (1.57 g, 8.05 mmol) and 4-fluorobenzoic acid (1.1 mL, 9.26 mmol), as starting compounds, the title compound was prepared by the procedures described in the preparation of compound 10 to yield 1.07 g (42%) of 11 as an orange oil. ¹H NMR (400 MHz, CDCl₃) δ ppm 8.48-8.63 (m, 1H), 8.10 (d, J=7.67 Hz, 1H), 7.99 (dd, J=8.62, 1.50 Hz, 1H), 7.78 (d, J=8.34 Hz, 2H), 7.37-7.60 (m, 5H), 7.21-7.34 (m, 1H), 4.40 (q, J=7.23 Hz, 2H), 1.40-1.55 (m, 3H). ¹³C NMR (101 MHz, CDCl₃) δ ppm 195.28, 142.56, 140.62, 137.93, 137.30, 131.28, 128.60, 128.45, 128.26, 128.06, 126.53, 123.89, 123.08, 122.58, 120.75, 120.01, 109.00, 108.07, 37.83, 26.87, 13.79. HRMS calculated for $C_{21}H_{17}FNO$ (M+H)⁺ 318.1294, found 318.0766.

Example 8: 9-ethyl-3-(4-methylbenzoyl)-9H-carbazole (12)

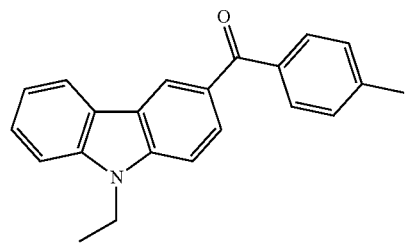 [SMILES: CCn1c2ccccc2c2cc(C(=O)c3ccc(C)cc3)ccc21]

Using 9-ethyl-9H-carbazole 5 (325 mg, 1.67 mmol) and p-toluoyl chloride (246 mg, 2.00 mmol) as starting compounds, the title compound was prepared by the procedures described in the preparation of compound 10 to yield 241 mg (46%) of 12 as a yellow glass. ¹H NMR (400 MHz, CDCl₃) δ ppm 8.63 (d, J=1.30 Hz, 1H), 8.16 (d, J=7.77 Hz, 1H), 8.04 (dd, J=8.58, 1.67 Hz, 1H), 7.64-7.73 (m, 2H), 7.56 (td, J=7.64, 1.03 Hz, 1H), 7.29-7.37 (m, 1H), 7.17-7.28 (m, 4H), 4.43 (q, J=7.23 Hz, 2H), 2.31 (s, 3H) 1.51 (t, J=7.23 Hz, 3H). ¹³C NMR (101 MHz, CDCl₃) δ ppm 197.02, 143.46, 141.52, 135.19, 135.07, 131.36, 131.28, 128.15, 128.12, 126.46, 123.76, 122.64, 122.22, 120.66, 119.72, 115.90, 115.68, 108.95, 107.54, 36.98, 21.43, 13.13. HRMS calculated for $C_{22}H_{20}NO$ (M+H)⁺: 314.1539, found: 314.1545.

Example 9: 1-(9-ethyl-9H-carbazol-3-yl)-2-phenylethan-1-one (13)

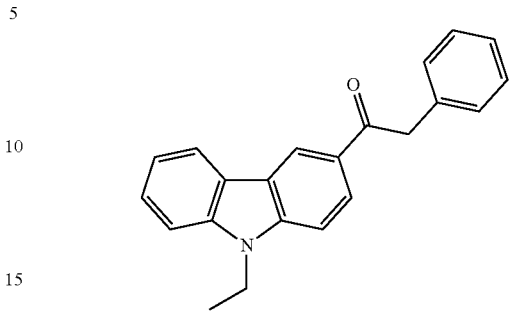

Using 9-ethyl-9H-carbazole 5 (325 mg, 1.67 mmol) and phenylacetyl chloride (246 mg, 2.00 mmol) as starting compounds, the title compound was prepared by the procedures described in the preparation of compound 10 to yield 299 mg (57%) of 13 as a yellow glass. ¹H NMR (400 MHz, CDCl₃) δ ppm 8.81 (d, J=1.30 Hz, 1H), 8.24 (d, J=7.77 Hz, 1H), 8.09 (dd, J=8.58, 1.67 Hz, 1H), 7.59-7.69 (m, 2H), 7.29-7.37 (m, 2H), 7.23-7.36 (m, 5H), 4.43 (q, J=7.23 Hz, 2H), 4.12 (s, 2H), 2.31 (s, 3H), 1.51 (t, J=7.23 Hz, 3H). ¹³C NMR (101 MHz, CDCl₃) δ ppm 195.38, 141.72, 135.66, 129.74, 129.13, 128.19, 128.42, 126.35, 124.32, 123.64, 122.22, 120.63, 119.79, 115.57, 115.35, 108.78, 107.54, 44.43, 36.98, 13.13. HRMS calculated for $C_{22}H_{20}NO$ (M−H)⁻ 314.1539, found: 314.1530.

Example 10: 9-ethyl-3-(naphthalene-1-carbonyl)-9H-carbazole (14)

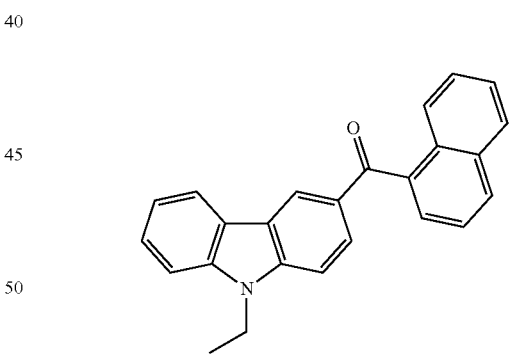

Using 9-ethyl-9H-carbazole 5 (100 mg, 0.40 mmol) and 1-naphthoyl chloride (74 mL, 0.71 mmol) as starting compounds, the title compound was prepared following the procedures described in the preparation of compound 10. Compound 14 as a yellowish viscous oil was obtained. Yield: 141.1 mg (41.5%). ¹H NMR (400 MHz, CDCl₃) δ 8.65 (s, 1H), 8.16 (d, 1H), 8.04 (t, 2H), 7.96 (d, 1H), 7.51 (d, 2H), 7.42 (m, 2H), 7.33 (m, 4H), 7.18 (t, 1H), 4.18 (q, 2H), 1.45 (t, 3H). ¹³C NMR (101 MHz, CDCl₃) δ 197.79, 143.02, 140.73, 137.27, 133.77, 130.44, 128.64, 128.37, 126.56, 126.38, 125.97, 124.58, 124.33, 120.89, 120.12, 109.05, 108.13, 37.92, 13.87. HRMS calculated for $C_{25}H_{19}NO$ (M+H)⁺: 350.1466, found: 350.1536.

Example 11: 9-propyl-9H-carbazole (15)

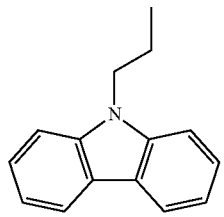 [SMILES: CCCn1c2ccccc2c2ccccc21]

Using carbazole (550 mg, 2.52 mmol) and 1-bromopropane (369 mg, 3 mmol), as the starting compounds, the title compound was prepared by the procedures described in the preparation of compound 10 to yield 410 mg (74%) of 15 as a yellow oil. $^1$H NMR (400 MHz, CDCl$_3$) δ 8.09 (d, J=7.8 Hz, 2H), 7.44 (ddd, J=8.2, 6.9, 1.2 Hz, 2H), 7.39 (d, J=8.1 Hz, 2H), 7.21 (ddd, J=8.0, 6.8, 1.1 Hz, 2H), 4.24 (t, J=7.2 Hz, 2H), (m, 2H), 0.95 (t, J=7.4 Hz, 3H). $^{13}$C NMR (101 MHz, CDCl$_3$) δ 140.71, 125.75, 123.00, 120.53, 118.90, 108.89, 44.80, 22.51, 12.02.

Example 12: 9-propyl-3-[(4-methylnaphthalen-1-yl)carbonyl]-9H-carbazole (16)

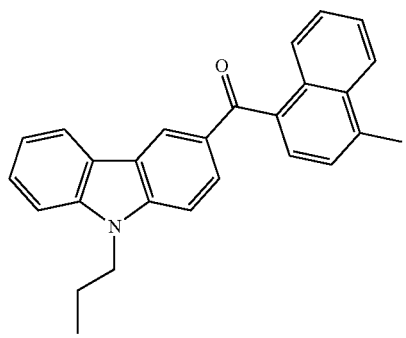 [SMILES: CCCn1c2ccccc2c2cc(C(=O)c3ccc(C)c4ccccc34)ccc21]

Using 9-propyl-9H-carbazole 15 (350 mg, 1.67 mmol) and 4-methyl-1-naphthoyl chloride (246 mg, 2.00 mmol) as starting compounds, the title compound was prepared by the procedures described in the preparation of compound 10 to yield 327 mg (52%) of 16 as a yellow glass. $^1$H NMR (400 MHz, CDCl$_3$) δ ppm 8.62 (s, 1H), 8.14 (d, J=8.53 Hz, 1H), 8.04 (t, J=9.03 Hz, 2H), 7.96 (d, J=7.78 Hz, 1H), 7.47-7.55 (m, 2H), 7.38-7.47 (m, 2H), 7.27-7.38 (m, 3H), 7.18 (t, J=7.40 Hz, 1H), 4.18 (t, J=7.03 Hz, 2H), 2.73 (s, 3H), 1.78-1.90 (m, 2H), 0.97 (t, J=7.40 Hz, 3H). $^{13}$C NMR (101 MHz, CDCl$_3$) δ ppm 197.63, 143.30, 141.06, 137.08, 132.71, 129.58, 128.35, 126.76, 126.41, 126.04, 125.42, 124.24, 122.97, 122.41, 120.53, 119.84, 118.56, 109.16, 108.57, 44.62, 60.38, 22.72, 19.67, 11.83. HRMS calculated for C$_{27}$H$_{24}$NO (M+H)$^+$: 378.1852, found: 378.1851.

Example 13: 9-(2,2,2-trifluoroethyl)-9H-carbazole (17)

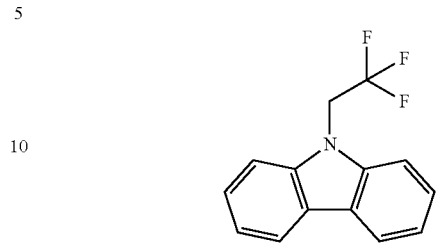

Using carbazole (300 mg, 1.80 mmol) and 2-chloro-1,1,1-trifluoroethane (0.25 mL, 1.28 mmol) as starting compounds, the title compound was prepared by the procedures described in the preparation of compound 10 to yield 372 mg (83%) of 17 as a yellow oil. $^1$H NMR (500 MHz, CDCl$_3$) δ ppm 8.17 (d, J=7.86 Hz, 2H), 7.53 (t, J=7.63 Hz, 2H), 7.37 (d, J=7.86 Hz, 2H), 7.22-7.32 (m, 2H), 4.35 (s, 2H). $^{13}$C NMR (126 MHz, CDCl$_3$) δ ppm 140.14, 127.44, 122.91, 120.53, 118.77, 111.23, 108.37, 72.14, 19.7.

Example 14: 3-(4-methylnaphthalene-1-carbonyl)-9-(2,2,2-trifluoroethyl)-9H-carbazole (18)

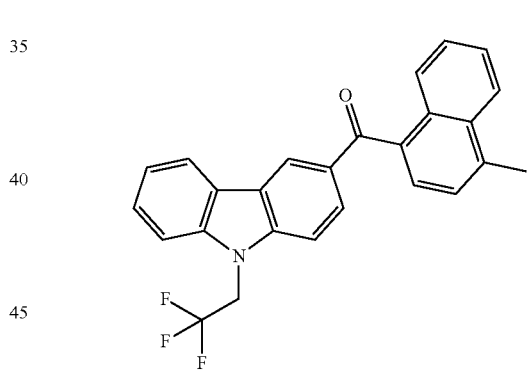

Using 9-(2,2,2-trifluoroethyl)-9H-carbazole 17 (350 mg, 1.41 mmol) and 4-methyl-1-naphthoyl chloride (246 mg, 2.00 mmol) as starting compounds, the title compound was prepared by the procedures described in the preparation of compound 10 to yield 363 mg (62%) of 18 as a yellow glass. $^1$H NMR (400 MHz, CDCl$_3$) δ 8.64 (s, 1H), 8.00-8.19 (m, 4H), 7.36-7.59 (m, 7H), 7.24-7.27 (m, 1H), 4.37 (s, 2H), 2.79 (s, 3H). $^{13}$C NMR (101 MHz, CDCl$_3$) δ ppm 197.6, 142.8, 139.7, 136.6, 136.1, 133.2, 131.2, 129.5, 128.8, 126.7, 126.9, 126.7, 126.5, 126.2, 125.2, 124.9, 124.6, 123.3, 122.4, 120.9, 120.0, 112.7 109.8, 108.6, 71.8, 19.7. HRMS calculated for C$_{26}$H$_{19}$F$_3$NO (M+H)$^+$: 418.1413, found: 418.1345.

Example 15: (9-ethyl-9H-carbazol-3-yl)(quinolin-5-yl)methanol (19, also as ST-401)

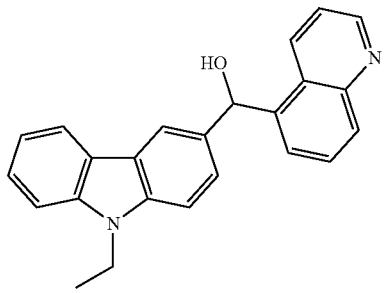 [SMILES: CCn1c2ccccc2c2cc(C(O)c3cccc4ncccc34)ccc21]

A solution of 1.5 M tert-buthyllithium in pentane (9 mL) was added dropwise in 20 min. at −78° C. to a solution of 3-bromo-9-ethyl-9H-carbazole (1.9 g; 0.007 mol) dissolved in dry tetrahydrofuran (50 mL). The solution was stirred at −78° C. for 1 hour. A brownish precipitate formed. TLC in cyclohexane/dichloromethane 9/1: 100% conversion. A solution of quinoline-5-carbaldehyde (1.1 g; 0.007 mol) dissolved in 50 mL of dry tetrahydrofuran was added dropwise at −78° C. in 15 min. The resulting solution was stirred at −78° C. for 1.5 hours. 220 mL of a saturated NH$_4$Cl solution was added. The product was then extracted with ethyl acetate (200 mL and then 50 mL). The organic phases were combined and washed with water (2×100 mL) and dried over MgSO$_4$. The solution was concentrated under reduced pressure. The residue was purified by column chromatography on silica gel eluting with ethyl acetate/cyclohexanes to afford the pure product as a pale yellow solid. Yield: 1.54 g (62.4%). $^1$H NMR (400 MHz, CDCl$_3$) δ 8.78 (d, J=4.0, 1H), 8.40 (d, J=8.6, 1H), 8.12 (s, 1H), 8.06 (d, J=8.4, 1H), 8.02 (d, J=7.8, 1H), 7.82 (d, J=7.1, 1H), 7.78-7.67 (m, 1H), 7.45 (t, J=7.6, 1H), 7.39 (td, J=4.7, 2.3, 2H), 7.31 (d, J=8.5, 1H), 7.23 (d, J=4.2, 1H), 7.20 (t, J=7.3, 1H), 6.65 (s, 1H), 4.32 (q, J=7.2, 2H), 2.47 (s, 1H), 1.39 (t, J=7.2, 3H). $^{13}$C NMR (101 MHz, CDCl$_3$) δ 149.94, 139.74, 139.66, 133.53, 132.82, 129.69, 128.90, 125.94, 124.93, 124.89, 120.80, 120.53, 119.17, 119.01, 108.70, 108.61, 74.18, 37.65, 13.83.

Alternatively, compound 19 was obtained by adding t-butyl lithium in pentane (20.67 mL, 1.7 M, 35.14 mmol) to a solution of 3-bromo-9-ethyl-9H-carbazole (5.0 g, 18.2 mmol) in anhydrous tetrahydrofuran (130 mL) at −78° C. under argon dropwise over 30 minutes. After the resulting yellow reaction mixture was stirred at −78° C. for 1 hour, a solution of quinolone-5-carbaldehyde (2.86 g, 18.2 mmol) in anhydrous tetrahydrofuran (130 mL) was added dropwise over 1 hour. The resulting yellow solution was stirred at −78° C. under argon for another 1.5 hours before saturated aqueous NH$_4$Cl (250 mL) was added slowly. After warming to room temperature, the mixture was extracted with ethyl acetate (250 mL×2). The combined organic extracts were washed with saturated aqueous NaCl (250 mL), dried (MgSO$_4$), and concentrated in vacuo. Purification by silica gel chromatography using 50% and 70% ethyl acetate/hexane and lyophilization with CH$_3$CN/H$_2$O afforded compound 19 (4.7 g, 73%) as an off-white solid.

Example 16: 9-ethyl-3-(quinoline-5-carbonyl)-9H-carbazole (20)

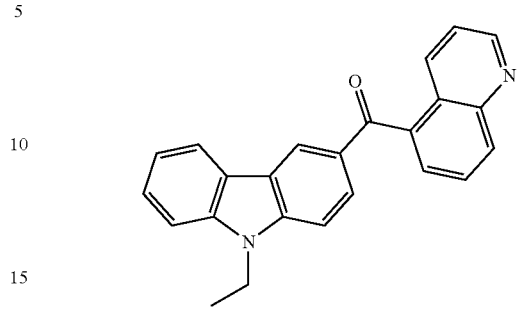

A suspension of 19 (1.4 g; 3.97 mmol) dissolved in dichloromethane (20 mL), pyridinium dichromate (PDC) (2.95 g, 7.84 mmol) and molecular sieves 4 Å (2.95 g) was stirred for 2 hours at room temperature. The resulting solution was filtered over a pad of SiO$_2$ and eluted with ethyl acetate. 350 mL of solvent (ethyl acetate and dichloromethane) was collected, and the solutions were combined and concentrated under reduced pressure to afford the pure product as a pale yellow solid. Yield: 995 mg (78.7%). $^1$H NMR (400 MHz, CDCl$_3$) δ 9.04-8.92 (m, 1H), 8.62 (s, 1H), 8.49 (d, J=8.5, 1H), 8.31 (d, J=8.3, 1H), 8.06 (d, J=7.4, 2H), 7.87-7.77 (m, 1H), 7.75 (d, J=6.9, 1H), 7.52 (t, J=7.6, 1H), 7.49-7.43 (m, 2H), 7.43-7.39 (m, 1H), 7.31-7.25 (m, 2H), 4.42 (q, J=7.2, 2H), 1.48 (t, J=7.2, 3H). $^{13}$C NMR (101 MHz, CDCl$_3$) δ 196.38, 150.91, 148.35, 143.07, 140.74, 137.72, 134.31, 132.13, 129.16, 128.54, 128.02, 127.78, 126.69, 126.63, 124.37, 123.19, 122.84, 121.95, 120.87, 120.24, 109.11, 108.24, 37.96, 13.86. HRMS calculated for C$_{24}$H$_{19}$N$_2$O (M+H)$^+$: 351.1491, found: 351.1487.

Example 17: (9-ethyl-9H-carbazol-3-yl)(quinolin-8-yl)methanol (21)

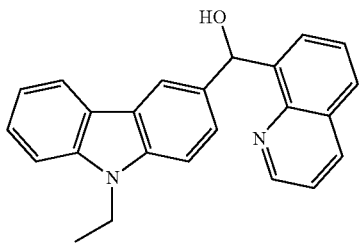 [SMILES: CCn1c2ccccc2c2cc(C(O)c3cccc4cccnc34)ccc21]

To an oven-dried round-bottom flask flushed with N$_2$ was added 3-bromo-9-ethyl-9H-carbazole (508 mg, 1.85 mmol) in 13 mL dry tetrahydrofuran. The mixture was cooled to −78° C. and tert-BuLi (2M in heptane) (1.85 mL, 3.7 mmol) was added dropwise. The mixture was stirred at −78° C. for 1 hour, then 8-Quinolinecarboxaldehyde (291 mg, 1.85 mmol) was added. The resulting mixture was stirred at −78° C. for 1.5 hour, then allowed to warm to 0° C. 50 mL sat. NH$_4$Cl was added, then organics were extracted with ethyl acetate (2×30 mL), washed with water and brine, and dried over MgSO$_4$. Solvents were removed in vacuo, and the resulting oil was purified by column chromatography eluting with a gradient of 12-100% ethyl acetate in heptane to yield the title compound as a dark purple oil (303 mg, 46.4% yield). ¹H NMR (400 MHz, CDCl₃) δ 8.90 (dd, J=4.3, 1.8 Hz, 1H), 8.26-8.24 (m, 1H), 8.22 (dd, J=8.4, 1.8 Hz, 1H), 8.06 (dt, J=7.8, 1.0 Hz, 1H), 7.75 (dd, J=8.0, 1.7 Hz, 1H), 7.60 (dd, J=8.4, 1.7 Hz, 1H), 7.45 (dd, J=6.1, 1.8 Hz, 2H), 7.39 (d, J=5.0 Hz, 1H), 7.19 (ddd, J=7.9, 6.9, 1.2 Hz, 1H), 6.97 (s, 1H), 6.67 (s, 1H), 4.36 (q, J=7.2 Hz, 2H), 1.42 (t, J=7.2 Hz, 3H).

Example 18: 9-ethyl-3-(quinoline-8-carbonyl)-9H-carbazole (22)

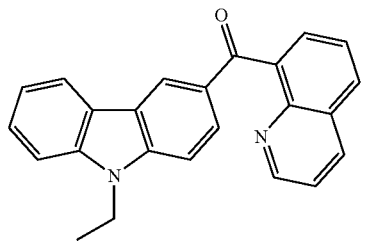 [SMILES: CCn1c2ccccc2c2cc(C(=O)c3cccc4cccnc34)ccc21]

A suspension of (9-ethyl-9H-carbazol-3-yl)(quinolin-8-yl)methanol 21 (300 mg, 0.85 mmol) dissolved in dichloromethane (5 mL), PDC (641 mg, 1.70 mmol) and molecular sieves 4 Å (632 mg) was stirred for 3 hours at room temperature. The resulting solution was filtered under a pad of SiO₂, and eluted with ethyl acetate. 350 mL of solvent (ethyl acetate and dichloromethane) were collected and the solutions were combined and then concentrated in vacuo. The resulting oil was purified using column chromatography eluting with a gradient of 7-50% ethyl acetate in heptane to afford the pure product as a bright-orange solid (73 mg, 24.4% yield). ¹H NMR (400 MHz, CDCl₃) δ 8.87 (dd, J=4.2, 1.8 Hz, 1H), 8.60 (d, J=1.7 Hz, 1H), 8.25 (dd, J=8.3, 1.8 Hz, 1H), 8.05 (dd, J=8.7, 1.7 Hz, 1H), 8.03-7.97 (m, 2H), 7.81 (dd, J=7.0, 1.5 Hz, 1H), 7.67 (dd, J=8.2, 7.0 Hz, 1H), 7.48 (ddd, J=8.3, 7.0, 1.2 Hz, 1H), 7.44-7.40 (m, 2H), 7.38 (d, J=8.7 Hz, 1H), 7.23 (ddd, J=8.0, 7.0, 1.1 Hz, 1H), 4.39 (q, J=7.2 Hz, 2H), 1.45 (t, J=7.2 Hz, 3H). ¹³C NMR (101 MHz, CDCl₃) δ 197.39, 150.97, 146.36, 143.05, 140.69, 140.37, 136.04, 129.42, 129.26, 128.56, 128.37, 128.06, 126.37, 125.92, 124.20, 123.44, 122.79, 121.58, 120.83, 119.96, 108.97, 108.02, 77.36, 77.25, 77.05, 76.73, 37.86, 13.83. HRMS calculated for C₂₄H₁₈N₂O (M+H)⁺: 351.1492, found: 351.1656.

Example 19: (9-ethyl-9H-carbazol-3-yl)(1,2,3,4-tetrahydroquinolin-5-yl)methanone (23)

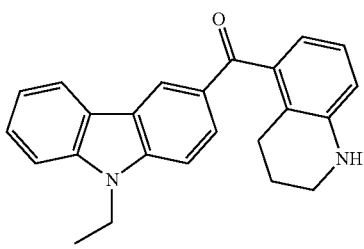 [SMILES: CCn1c2ccccc2c2cc(C(=O)c3cccc4c3CCCN4)ccc21]

To a solution of 9-ethyl-3-(quinoline-5-carbonyl)-9H-carbazole 20 (106.3 mg, 0.30 mmol) in MeOH (1.5 mL) and tetrahydrofuran (1 mL) was added sodium cyanoborohydride (95.46 mg, 1.52 mmol). Boron trifluoride diethyl etherate (190.9 μL, 1.52 mmol) was added dropwise to the resulting solution, with evolution of gas. The solution was stirred and refluxed at 63° C. for 3.5 hours under N₂. 3 mL NH₃ (25% in water) was added to the reaction mixture, then diluted with another 10 mL of water. The product was extracted with ethyl acetate (2×15 mL), and washed with brine (1×30 mL). The organic layers were dried over anhydrous MgSO₄, and the solvent was removed in vacuo. Raw product was purified with flash chromatography (16-40% ethyl acetate in heptane) to yield 23 as a sticky yellow solid (43.9 mg, 41.3% yield). ¹H NMR (400 MHz, CDCl₃) δ 8.68-8.52 (m, 1H), 8.11 (d, J=7.7 Hz, 0H), 8.08-8.00 (m, 1H), 7.51 (ddd, J=8.1, 6.3, 2.6 Hz, 1H), 7.42 (dd, J=15.0, 8.5 Hz, 1H), 7.32-7.27 (m, 0H), 7.05 (t, J=7.7 Hz, 1H), 6.75-6.65 (m, 1H), 6.61 (dt, J=8.1, 2.2 Hz, 1H), 4.40 (q, J=7.2 Hz, 1H), 4.10 (s, 1H), 3.32 (dd, J=7.0, 3.9 Hz, 1H), 2.72 (t, J=6.2 Hz, 1H), 1.88 (p, J=6.0 Hz, 1H), 1.47 (t, J=7.2 Hz, 2H). ¹³C NMR (101 MHz, CDCl₃) δ 198.70, 145.01, 142.90, 140.68, 140.54, 129.03, 128.31, 126.44, 126.14, 124.07, 123.36, 122.73, 120.90, 120.03, 119.09, 116.93, 115.51, 108.97, 108.01, 41.73, 37.88, 24.76, 21.89, 13.85. HRMS calculated for C₂₄H₂₂N₂O (M+H)⁺: 355.1804, found: 355.1810.

Example 20: 9-ethyl-3-(1,2,3,4-tetrahydroquinoline-8-carbonyl)-9H-carbazole (24)

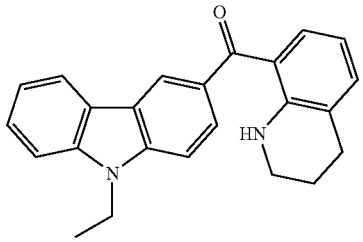 [SMILES: CCn1c2ccccc2c2cc(C(=O)c3cccc4c3NCCC4)ccc21]

To a solution of 9-ethyl-3-(quinoline-8-carbonyl)-9H-carbazole 22 (60 mg, 0.171 mmol) in MeOH (0.75 mL) and tetrahydrofuran (0.5 mL) was added sodium cyanoborohydride (54.8 mg, 0.856 mmol). Boron trifluoride diethyl etherate (108 μL, 0.856 mmol) was added dropwise to the resulting solution, with evolution of gas. The solution was stirred and refluxed at 60° C. for 3.5 hours under nitrogen. 2 mL ammonia (25% in water) was added to the reaction mixture, which was then diluted with another 10 mL of water. The product was extracted with ethyl acetate (2×15 mL) and washed with brine (1×30 mL). The organic layers were dried over anhydrous MgSO₄ and the solvent was removed in vacuo. Raw product was purified with flash chromatography twice eluting with a gradient of 15-55% ethyl acetate in heptane and then 10-100% dichloromethane in heptane to yield 24 as a yellow oil (12.6 mg, 20.8% Yield). ¹H NMR (400 MHz, CDCl₃) δ 8.43 (t, J=2.5 Hz, 2H), 8.10 (d, J=7.7 Hz, 1H), 7.84 (dd, J=8.5, 1.7 Hz, 1H), 7.50 (ddd, J=8.2, 6.9, 1.2 Hz, 1H), 7.47-7.40 (m, 3H), 7.27 (d, J=8.1 Hz, 1H), 7.08 (dd, J=7.1, 1.4 Hz, 1H), 6.47-6.39 (m, 1H), 4.41 (q, J=7.2 Hz, 2H), 3.49 (td, J=5.9, 2.7 Hz, 2H), 2.86 (t, J=6.3 Hz, 2H), 2.02-1.94 (m, 2H), 1.47 (t, J=7.2 Hz, 3H). ¹³C NMR (101 MHz, CDCl₃) δ 199.08, 148.76, 141.63, 140.59, 133.38, 133.30, 131.50, 127.75, 126.19, 123.24, 122.92, 122.46, 122.28, 120.77, 119.61, 117.18, 112.80, 108.83, 107.77, 77.35, 77.23, 77.03, 76.71, 41.26, 39.00, 37.80, 35.45, 34.15, 31.91, 29.52, 29.45, 29.05, 27.93, 25.05, 22.71, 22.68, 20.81, 20.18, 19.19, 14.42, 14.12, 13.85, 11.41, 10.97. HRMS calculated $C_{24}H_{22}N_2O$ (M+H)$^+$: 355.1805, found 355.1815.

Example 21: 9-ethyl-3-[(1,2,3,4-tetrahydroquinolin-1-yl)carbonyl]-9H-carbazole (25)

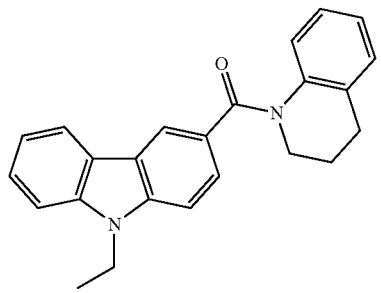 [SMILES: CCn1c2ccccc2c2cc(C(=O)N3CCCc4ccccc43)ccc21]

Using 9-ethyl-9H-carbazole-3-carboxylic acid 7 (200 mg, 0.84 mmol) and 1,2,3,4-tetrahydroquinoline (171 mg, 1.29 mmol) as starting compounds, the title compound was prepared following the procedures described for the preparation of compound 9 to yield 241 mg (81%) of 25 as a yellow glass. $^1$H NMR (400 MHz, CDCl$_3$) δ ppm 8.62 (s, 1H), 8.04 (t, J=9.03 Hz, 2H), 7.96 (d, J=7.78 Hz, 1H), 7.41-7.54 (m, 3H), 7.08 (t, J=7.40 Hz, 1H), 6.89-7.01 (m, 3H), 4.38 (t, J=7.03 Hz, 2H), 2.73-2.84 (m, 2H), 1.54-1.70 (m, 4H), 1.28 (t, J=7.40 Hz, 3H). $^{13}$C NMR (101 MHz, CDCl$_3$) δ ppm 166.05, 141.72, 135.50, 131.12, 129.53, 128.00, 126.77, 125.17, 124.85, 124.46, 123.83, 123.56, 122.45, 121.39, 118.95, 118.55, 118.26, 107.58, 106.98, 51.10, 42.14, 28.87, 25.32, 20.09, 14.72. HRMS calculated for $C_{24}H_{23}N_2O$ (M+H)$^+$: 355.1804, found: 355.1831.

Example 22: 9-ethyl-3-(4-methylnaphthalene-1-carbothioyl)-9H-carbazole (26)

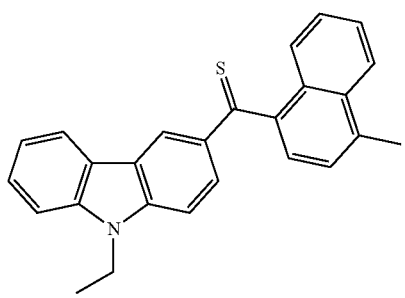 [SMILES: CCn1c2ccccc2c2cc(C(=S)c3ccc(C)c4ccccc34)ccc21]

Under argon, a solution of carbazole 8 (62 mg, 0.17 mmol) and Lawesson's reagent (49 mg, 0.12 mmol) in toluene (3 mL) was tightly capped in a 5 mL microwave vessel. The mixture was subjected to microwave irradiation at 140° C. for 4 hours and then cooled to room temperature. The organic solvent was evaporated in vacuo, and the residue was purified by column chromatography on silica gel using heptanes/ethyl acetate in different proportions to yield thioamide 26 as a yellow glass. Yield: 20 mg (31%). $^1$H NMR (400 MHz, CDCl$_3$) δ ppm 8.63 (s, 1H), 8.10 (m, 4H), 7.49 (m, 7H), 7.26 (t, 1H), 4.41 (q, 2H), 2.82 (s, 3H), 1.46 (t, 3H). $^{13}$C NMR (101 MHz, CDCl$_3$) δ ppm 218.89, 142.92, 140.70, 137.27, 129.82, 128.61, 126.94, 126.60, 126.49, 126.21, 125.32, 124.35, 120.88, 120.05, 109.01, 108.06, 37.91, 19.92, 13.87. HRMS calculated for $C_{26}H_{22}NS$ (M+H)$^+$: 380.1467, found: 380.1498.

Example 23: (9-ethyl-9H-carbazol-3-yl)(4-methylnaphthalen-1-yl)methanol (27)

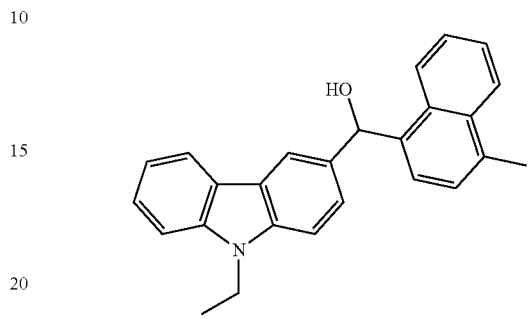

Carbazole 8 (2.59 g; 0.071 mol) was dissolved in 62 mL of dioxane, and 100 mL of MeOH was added. NaBH$_4$ (400 mg; 0.01 mol) was added to the solution over 10 min. The solution was stirred for 14 hours at room temperature. 110 mg of NaBH$_4$ was added to complete the reduction, and the reaction mixture was stirred at room temperature for 14 hours 250 mL of water was added. The product was then extracted with ethyl acetate (250 mL) from water. The organic phases were combined and washed with water (2×100 mL) and dried over MgSO$_4$. The solution was concentrated under reduced pressure. Flash-chromatography of the crude mixture using a dichloromethane/cyclohexane gradient afforded the pure product as a pale yellow solid. Yield: 1.735 g (66.6%). $^1$H NMR (400 MHz, CDCl$_3$) δ 8.18 (s, 1H), 8.12 (d, J=8.2, 1H), 8.05 (dd, J=15.5, 8.8, 2H), 7.65 (d, J=7.3, 1H), 7.53-7.37 (m, 6H), 7.37-7.29 (m, 2H), 7.23-7.15 (m, 1H), 6.74 (d, J=3.8, 1H), 4.34 (q, J=7.2, 2H), 2.72 (s, 3H), 2.32 (d, J=3.9, 1H), 1.44-1.36 (m, 8H). $^{13}$C NMR (101 MHz, CDCl$_3$) δ 140.31, 139.56, 137.57, 134.38, 134.12, 133.06, 130.84, 126.16, 125.72, 125.37, 125.11, 124.80, 124.69, 124.18, 122.99, 122.89, 120.56, 119.26, 118.84, 108.51, 74.17, 37.62, 26.95, 19.66, 13.84.

Example 24: 9-(4-methylnaphthalene-1-carbonyl)-9H-carbazole (28)

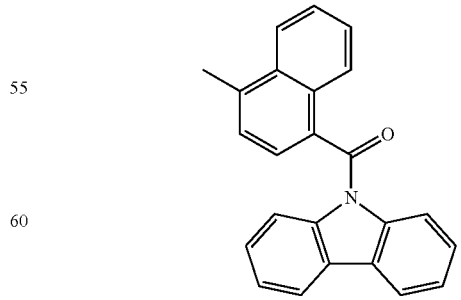

Using carbazole (300 mg, 1.80 mmol), and 4-methyl-1-naphthoyl chloride (0.25 mL, 1.28 mmol) as starting compounds, the title compound was prepared by the procedures described for the preparation of compound 5 to yield 96 mg (16%) of 28 as a yellow oil. (400 MHz, CDCl₃) δ ppm 8.92 (s, 1H), 8.55 (d, J=7.53 Hz, 1H), 8.16 (d, J=7.22 Hz, 1H), 7.81-7.91 (m, 2H), 7.49-7.62 (m, 3H), 7.11-7.25 (m, 4H), 2.63 (s, 3H). $^{13}$C NMR (101 MHz, CDCl₃) 5 ppm 167.81, 140.09, 139.36, 133.72, 132.29, 131.84, 129.61, 128.79, 126.76, 126.41, 126.04, 125.42, 120.53, 120.14, 119.49, 115.17, 19.64. HRMS calculated for $C_{24}H_{18}NO$ (M+H)$^+$: 336.1382, found: 380.1399.

Example 25: 9-ethyl-2-methoxy-9H-carbazole (29)

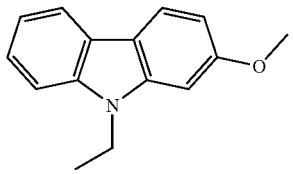 [SMILES: CCn1c2ccccc2c2ccc(OC)cc21]

Using 7-methoxycarbazole (1.2 g, 4.7 mmol), bromoethane (0.697 mL, 9.4 mmol) and Cs₂CO₃ (3.46 mg, 10 mmol) in dimethylformamide (40 mL) as starting compounds, the title compound was prepared by the procedures described for the preparation of compound 5 to yield 1.03 g (77%) of 29 as a greenish solid. $^1$H NMR (400 MHz, CDCl₃) δ 8.69 (dd, J=1.6, 0.6 Hz, 1H), 8.08 (dd, J=8.7, 1.7 Hz, 1H), 7.99 (d, J=8.4 Hz, 1H), 7.31 (d, J=8.6 Hz, 1H), 6.89 (dd, J=8.5, 2.2 Hz, 1H), 6.85 (d, J=2.1 Hz, 1H), 4.28 (q, J=7.2 Hz, 2H), 3.96 (s, 3H), 3.93 (s, 3H), 1.41 (t, J=7.2 Hz, 3H). $^{13}$C NMR (101 MHz, CDCl₃) δ 168.02, 159.55, 142.81, 141.95, 130.20, 127.23, 126.14, 122.90, 121.91, 121.47, 120.78, 116.88, 108.06, 107.67, 93.43, 55.75, 51.91, 37.76, 13.68.

Example 26: 9-ethyl-7-methoxy-9H-carbazole-3-carboxylic acid (30)

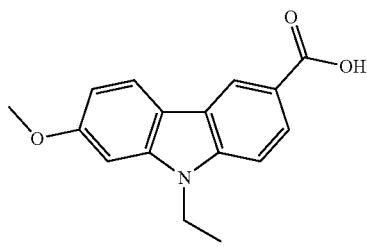 [SMILES: CCn1c2ccc(C(=O)O)cc2c2ccc(OC)cc21]

Using 9-ethyl-2-methoxy-9H-carbazole 29 (1.413 g, 4.99 mmol), as the starting compound, the title compound was prepared by the procedures described for the preparation of compound 6 to yield 990 mg (52%) of 29 as an orange solid. $^1$H NMR (400 MHz, DMSO-d₆) δ ppm 12.60 (br s, 1H), 8.68 (s, 1H), 8.12 (d, J=8.53 Hz, 1H), 7.99 (dd, J=8.53, 1.51 Hz, 1H), 7.58 (d, J=8.53 Hz, 1H), 7.18 (d, J=1.76 Hz, 1H), 6.86 (dd, J=8.53, 1.76 Hz, 1H), 4.42 (q, J=6.86 Hz, 2H), 3.89 (s, 3H), 1.24-1.37 (m, 4H). $^{13}$C NMR (101 MHz, DMSO-d₆) δ ppm 168.11, 159.27, 142.18, 141.72, 125.76, 122.22, 121.53, 121.47, 121.16, 115.80, 108.56, 108.40, 93.58, 55.52, 37.13, 13.56.

Example 27: 9-ethyl-2-methoxy-6-(4-methylnaphthalene-1-carbonyl)-9H-carbazole (31)

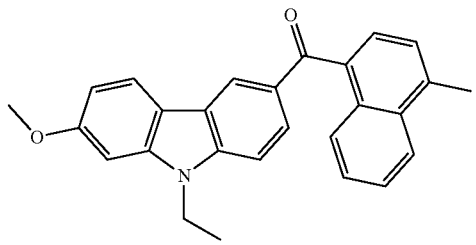

Using 7-methoxy-9-pentyl-9H-carbazole-3-carboxylic acid 26 (1.57 g, 8.05 mmol), and 1-methylnaphthalene (1.1 mL, 9.26 mmol) as starting compounds, the title compound was prepared by the procedures described for the preparation of compound 10 to yield 133 mg (42%) of 31 as an orange oil. $^1$H NMR (400 MHz, CDCl₃) δ 8.53 (d, J=1.7 Hz, 1H), 8.16-8.04 (m, 2H), 7.98 (dd, J=8.6, 1.7 Hz, 1H), 7.91 (d, J=8.4 Hz, 1H), 7.62-7.55 (m, 1H), 7.54 (d, J=7.1 Hz, 1H), 7.48 (ddd, J=8.2, 6.7, 1.3 Hz, 1H), 7.42-7.38 (m, 1H), 7.35 (d, J=8.5 Hz, 1H), 6.86 (dd, J=8.5, 2.2 Hz, 2H), 4.34 (q, J=7.3 Hz, 2H), 3.94 (s, 3H), 2.80 (d, J=1.0 Hz, 3H), 1.45 (t, J=7.2 Hz, 3H). $^{13}$C NMR (101 MHz, DMSO-d₆) δ ppm 168.10, 159.29, 142.19, 141.74, 125.77, 122.23, 121.55, 121.48, 121.16, 115.81, 108.58, 108.43, 93.60, 55.54, 37.15, 30.67, 13.58. HRMS calculated for $C_{27}H_{24}NO_2$ (M+H)$^+$: 394.1807, found 394.0875.

Example 28: ethyl 5-ethyl-1H,2H,3H,4H,5H-pyrido[4,3-b]indole-2-carboxylate (33)

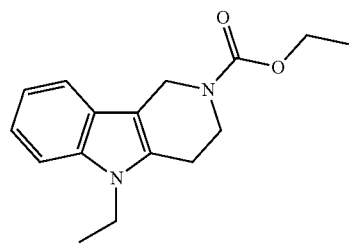 [SMILES: CCOC(=O)N1CCc2c(c3ccccc3n2CC)C1]

Step 1: Preparation of ethyl 1H,2H,3H,4H,5H-pyrido[4,3-b]indole-2-carboxylate (32)

12 M HCl (1.2 mL) was added to a solution of phenylhydrazine (3.64 mL, 36.99 mmol) and ethyl-4-oxocyclohexanecarboxylate (0.98 mL, 5.73 mmol) in ethanol (10 mL). The solution was microwaved at 140° C. for 3 hours. The reaction mixture was cooled on an ice-water bath, then poured onto a mixture of ice and a 4 M NaOH solution (50 mL) and extracted with ethyl acetate (150 mL). The organic phase was washed with saturated aqueous NaHCO₃ and brine, dried (MgSO₄), filtered and evaporated in vacuo. The residue was purified by column chromatography on silica gel eluting with ethyl acetate/heptanes in different proportions to yield 731 mg (52%) of 32 as an orange solid: $^1$H NMR (500 MHz, CDCl₃) δ ppm 7.77 (br. s., 1H), 7.28 (t, J=7.80 Hz, 1H), 7.14 (t, J=7.80 Hz, 1H), 7.02 (t, J=8.08 Hz, 1H), 6.98 (d, J=8.08 Hz, 1H), 4.15-4.29 (m, 2H), 3.90 (s, 2H), 3.39 (dd, J=16.01, 5.15 Hz, 2H), 2.92 (m, 1H), 2.22-2.31 (m, 1H), 1.32 (t, J=7.10 Hz, 3H). $^{13}$C NMR (126 MHz, CDCl$_3$) δ ppm 175.89, 137.20, 131.02, 127.33, 121.85, 117.32, 108.25, 103.93, 60.39, 45.13, 40.67, 25.86, 14.23.

Step 2: Preparation of ethyl 5-ethyl-1H,2H,3H,4H,5H-pyrido[4,3-b]indole-2-carboxylate (33)

Under argon, a solution of ethyl 1H,2H,3H,4H,5H-pyrido[4,3-b]indole-2-carboxylate 32 (1.5 g, 6.15 mmol), bromoethane (0.20 mL, 26.8 mmol), and NaH (131 mg, 44.8 mmol) in dimethylformamide (30 mL) was stirred for 30 min at room temperature The reaction mixture was diluted with dichloromethane (50 mL) and filtered through Celite©. The organic solvents were evaporated in vacuo. The concentrated residue was extracted with methyl tert-butyl ether/ethyl acetate (5:1, v/v, 150 mL). The organic layer was washed with NaHCO$_3$ (100 mL), dried over MgSO$_4$, filtered, and concentrated in vacuo. The resultant oil was purified by column chromatography on silica gel using heptanes/ethyl acetate (4:1, v/v) to afford the title compound as an orange oil, 1455 mg (87%) $^1$H NMR (500 MHz, CDCl$_3$) δ ppm 7.77 (br. s., 1H), 7.28 (t, J=7.80 Hz, 1H), 7.14 (t, J=7.80 Hz, 1H), 7.02 (t, J=8.08 Hz, 1H), 6.98 (d, J=8.08 Hz, 1H), 4.15-4.29 (m, 2H), 3.90 (s, 2H), 3.39 (dd, J=16.01, 5.15 Hz, 2H), 2.92 (m, 1H), 2.22-2.31 (m, 1H), 1.32 (t, J=7.10 Hz, 3H) $^{13}$C NMR (126 MHz, CDCl$_3$) δ ppm 175.74, 136.24, 131.72, 127.12, 121.58, 117.21, 108.32, 103.83, 60.27, 45.42, 40.55, 37.22, 25.79, 15.25, 14.12.

Example 29: 5-ethyl-1H,2H,3H,4H,5H-pyrido[4,3-b]indole (34)

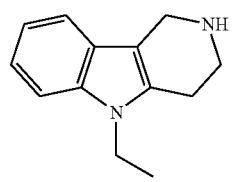

A solution of ethyl 5-ethyl-1H,2H,3H,4H,5H-pyrido[4,3-b]indole-2-carboxylate 33 (1400 mg, 5.15 mmol) and KOH (726 mg, 7.73 mmol) in a mixture of H$_2$O (2 mL) and ethanol (9 mL) was refluxed for 48 hours. The reaction mixture was cooled and diluted with ethyl acetate (50 mL), and the organic phase was washed with water and brine, dried (MgSO$_4$), filtered, and evaporated in vacuo. The resultant oil was purified by column chromatography on silica gel using heptanes/ethyl acetate in different proportions to afford the title compound as a light yellow oil, 988 mg (96%). δ ppm 7.50-7.56 (m, 1H), 7.09-7.15 (m, 3H), 4.09 (q, J=7.06 Hz, 2H), 3.66 (br. s., 2H), 3.26-3.34 (m, 2H), 2.87-2.96 (m, 2H), 1.16 (t, J=7.06 Hz, 3H). $^{13}$C NMR (101 MHz, DMSO-d$_6$) δ ppm 135.11, 132.14, 129.12, 122.15, 119.24, 118.56, 108.33, 108.10, 44.99, 41.59, 37.18, 25.77, 15.15.

Example 30: 5-ethyl-2-[(4-methylnaphthalen-1-yl)carbonyl]-1H,2H,3H,4H,5H-pyrido[4,3-b]indole (35)

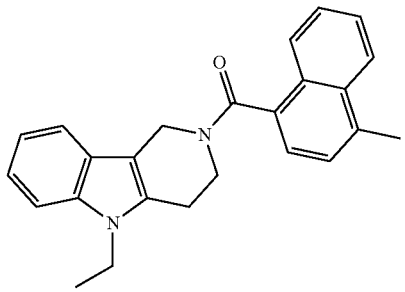 [SMILES: CCn1c2c(c3ccccc31)CN(C(=O)c1ccc(C)c3ccccc13)CC2]

Using 5-ethyl-1H,2H,3H,4H,5H-pyrido[4,3-b]indole 34 (250 mg, 1.25 mmol), and 4-methyl-1-naphthoic acid (348 mg, 1.87 mmol) as starting compounds, the title compound was prepared by the procedures described for the preparation of compound 7 to yield 193 mg (42%) of 35 as an orange oil. $^1$H NMR (400 MHz, DMSO-d$_6$) δ ppm 8.71 (d, J=8.20 Hz, 1H), 8.07 (d, J=8.42 Hz, 1H), 7.72-7.81 (m, 2H), 7.52-7.66 (m, 2H), 7.35-7.50 (m, 2H), 7.29-7.35 (m, 2H), 6.98-7.02 (m, 1H), 6.91-6.96 (m, 1H), 4.36 (br s, 2H), 4.02 (q, J=7.01 Hz, 2H), 3.41-3.53 (m, 2H), 3.04-3.14 (m, 2H), 2.64 (s, 3H), 1.18 (t, J=7.01 Hz, 3H). $^{13}$C NMR (101 MHz, DMSO-d$_6$) δ ppm 168.86, 135.21, 135.14, 133.16, 132.09, 132.04, 129.15, 126.62, 126.32, 125.96, 125.91, 125.12, 124.65, 124.58, 123.15, 119.31, 118.70, 108.30, 108.00, 44.20, 42.78, 37.05, 25.47, 19.07, 15.15. HRMS calculated for C$_{25}$H$_{25}$N$_2$O (M+H)$^+$: 369.1961, found: 369.1936.

Example 31: Example Pharmaceutical Compositions Comprising Compound 19

Several pharmaceutical compositions comprising compound 19 were developed for in vivo testing in mice. Specifically, compound 19 was mixed in several known formulations (e.g., suitable compounds with hydrophobic Log P values) and maintained at −4° C. for 2 weeks (N=3 independent experiments). Compound 19 was found to be soluble at a concentration of 60 mM in the following pharmaceutical compositions:

(a) 10% dimethyl sulfoxide (DMSO) and 20% cremophore (CRE) in PBS buffer (DPBS), (b) 5% ethanol (EtOH) and 10% CRE in DPBS (i.e., 1:2:17), and (c) 5% EtOH and 20% CRE in DPBS (i.e., 1:4:15)

In contrast, compound 20 had lower solubility, and was found to be soluble in these compositions at concentrations of 45 mM.

Compound 19 was also found to be partially soluble at a concentration of 60 mM in 20% CRE in DPBS, and insoluble at a concentration of 60 mM in 10% DMSO in DPBS.

Example 32: (+)-(9-ethyl-9H-carbazol-3-yl)(quinolin-5-yl)methanol ((+)-19, ST-402)

(+)-19 enantiomer was obtained by chiral HPLC enantiomer purification of compound 19 using 50% EtOH with 0.1% isopropyl alcohol, and had 1.20 minutes retention time. NMR analysis polarimetry analysis of (+)-19 found that its optical rotation was +6.33°.

Example 33: (−)-(9-ethyl-9H-carbazol-3-yl)(quinolin-5-yl)methanol ((−)-19, ST-403)

(−)-19 enantiomer was obtained by chiral HPLC enantiomer purification of compound 19 using 50% EtOH with 0.1% isopropyl alcohol, and had 1.55 minutes retention time. NMR analysis polarimetry analysis of (−)-19 found that its optical rotation was −5.00°.

Biological Example 1: Antitumor Activity of Compounds of the Disclosure in the Human GBM Cell Line T98G Two prototypical MTAs that target the colchicine site, combretastatin A-4 (1) and nocodazole (3), exhibited the expected antitumor $EC_{50}$ s activity in the human GBM cells line, T98G (0.6 and 29 nM, respectively), but only killed T98G cells by a maximum of 30.4%±2.1 at 10 nM and 45.6%±1.7 at 10 µM, respectively, as measured by the cell viability assay, WST-1, 72 hours following treatment initiation (FIG. 1A). FIG. 1D shows that antitumor activity of 3 additional references MTAs: $EC_{50}$ and maximal killing values for colcemide were 113 nM and 35.9%±6.4 at 10 µM, for vinblastine were 184 nM and 36.0%±2.3 and for paclitaxel were 148 µM and 63.2%±2.5 at 30 µM. These results indicate that MTAs that inhibit assembly and destabilize MTs exhibit moderate activity in T98G cells.

Figure 2:
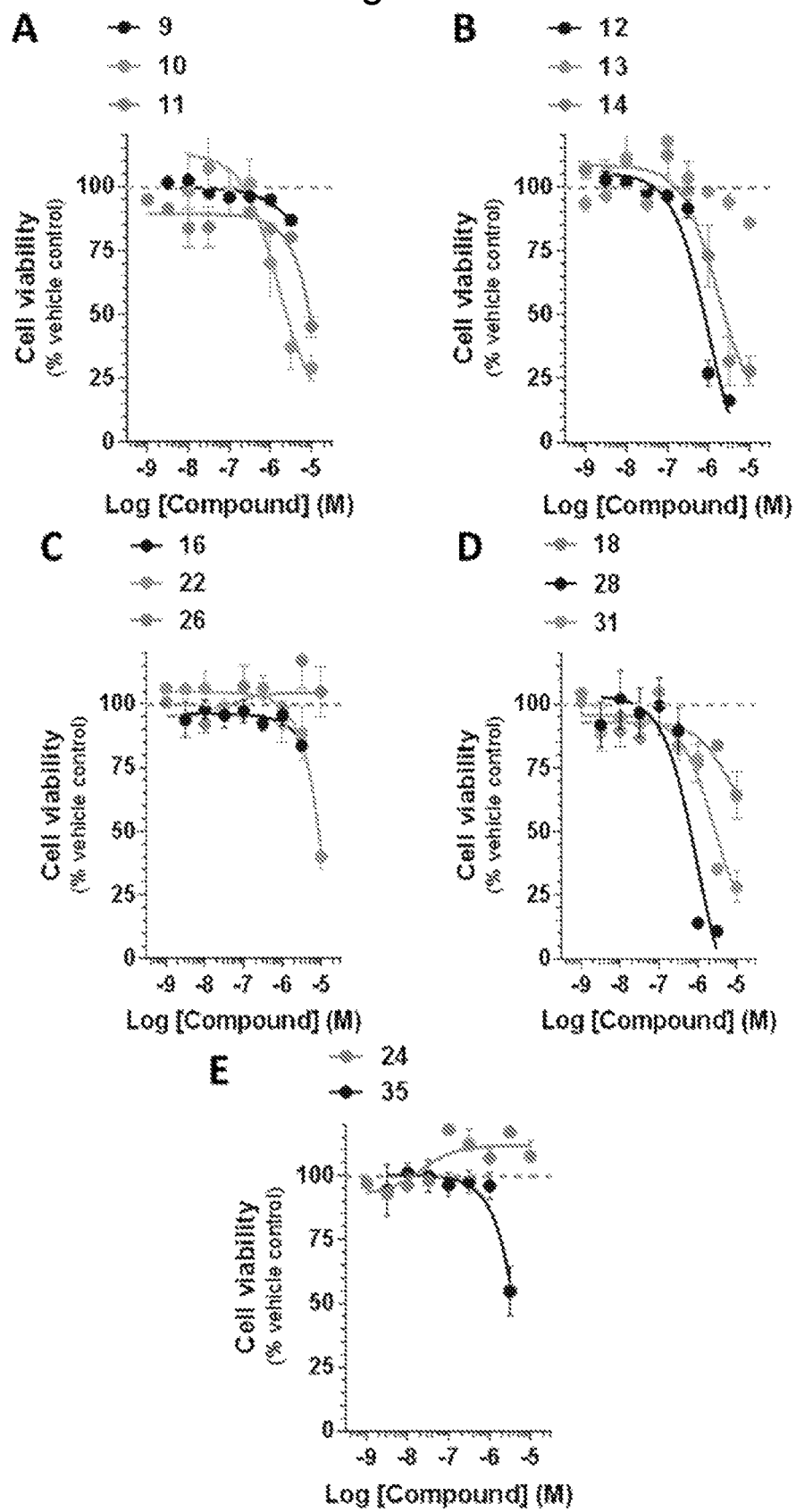
FIG. 2 illustrates cell-killing activity of the compounds of the disclosure tested in T98G cells in culture. T98G cells in culture were treated with increasing concentrations of compound and cell viability was measured 72 hours following treatment using WST-1. The dotted line shows 100% vehicle control. Data are the mean±SEM of at least three independent experiments performed in triplicate.

Using the same experimental design, T98G cells were treated with the compounds of the disclosure and the $EC_{50}$ and maximal efficacy values of their antitumor activities are provided in Table 1. Cells were treated with increasing concentrations of the compounds and cell viability was measured 72 hours following initiation of treatment using WST-1. $EC_{50}$ values were calculated using Prism® software, the curves shown in FIG. 1 and FIG. 2. When the curves could not be extrapolated, the $EC_{50}$ could not be calculated and values are indicated as >10 µM. Unless otherwise noted, maximal efficacies were measured at 10 µM. Data are the mean of at least three independent experiments performed in triplicate.

Table 1. Antitumor activity in T98G cells in culture.

TABLE 1

Antitumor activity in T98G cells in culture.

| Compound | Antitumor activity $EC_{50}$ | maximal killing (% ± SEM) |
|---|---|---|
| 8 | 87 nM | 45.3 ± 4.1 |
| 9 | >10 µM | 13.2 ± 1.7 |
| 10 | 1.5 µM | 71.1 ± 5.3 |
| 11 | 8 µM | 54.8 ± 4.0 |
| 12 | 993 nM | 83.6 ± 2.2 (at 3 µM) |
| 13 | >10 µM | 14.0 ± 2.1 (at 3 µM) |
| 14 | 1.7 µM | 72.0 ± 5.7 |
| 16 | >10 µM | 16.3 ± 2.2 |
| 18 | 5.6 µM | 35.6 ± 9.4 |
| 20 | 184 nM | 74.4 ± 1.7 (at 1 µM) |
| 22 | 8.8 µM | 60.0 ± 4.9 |
| 23 | >10 µM | −17.0 ± 10.8 (at 3 µM) |
| 24 | >10 µM | −18.0 ± 5.2 (at 100 nM) |
| 25 | 757 nM | 89.0 ± 0.7 (at 1 µM) |

TABLE 1-continued

Antitumor activity in T98G cells in culture.

| Compound | Antitumor activity $EC_{50}$ | maximal killing (% ± SEM) |
|---|---|---|
| 26 | >10 µM | −17.0 ± 10.8 (at 3 µM) |
| 27 | 560 nM | 72.8 ± 7.6 (at 3 µM) |
| 28 | 957 nM | 89.1 ± 0.7 |
| 31 | 2.6 µM | 71.6 ± 6.1 |
| 35 | >10 µM | 45.1 ± 9.9 (at 3 µM) |

FIGS. 1B and 1C show the concentration-dependent antitumor activities of five compounds: 8, 20, 23, 25 and 27. The concentration-dependent killing activities for the remaining compounds are provided in FIG. 2. First, fourteen compounds that have an ethyl moiety linked to the nitrogen of the carbazole and a carbonyl moiety to distinct biaromatic rings exhibited different $EC_{50}$ values. Specifically, five such compounds killed T98G cells with $EC_{50}$ values below 1 µM: 8 (87 nM)<20 (184 nM)<27 (560 nM)<25 (757 nM)<12 (993 nM), two compounds killed T98G cells with $EC_{50}$ values between 1 and 2 µM: 10 (1.5 µM) and 14 (1.7 µM), and seven compounds were only active at concentrations above five micromolar: 9, 13, 16, 18, 23, 24 and 26. The replacement of the methylnaphthyl group present in the most potent compound 8 by either toluyl (as in 12), a non-substituted naphthyl moiety (as in 14) or a benzyl moiety (as in 13) increased $EC_{50}$ values by 11-fold, 20-fold and more than 115-fold, respectively.

Second, compounds of the disclosure and carboline exhibited different maximal efficacies at killing T98G cells. Specifically, nine compounds killed T98G cells by more than 50% (i.e. the maximal killing efficacy reached by the reference MTAs). Thus, the rank order of these compounds is: 25 (89%)>12 (84%)>20 (74%)>14 (72%)=31 (72%)>27 (67%)>10 (61%)>22 (60%)>11 (55%). Three compounds, 8, 18 and 35, killed T98G cells by 35-45%; and six compounds did not affect T98G cell viability significantly, 9, 13, 16, 23, 24 and 26. These data show that the position of the nitrogen atom in the quinoline portion of compounds of the disclosure is relevant for maximal antitumor efficacy, as exemplified by the change in maximal efficacy at killing cells when moving the nitrogen atom from position 1 (as in the most efficacious compound 25) to position 5 (as in 20) or position 8 (as in 22), which reduces maximal antitumor efficacy by 29 and 96%, respectively.

Third, introduction of a nitrogen atom in position 6 of the carbazole scaffold increases the $EC_{50}$ value by more than 115-fold as indicated by comparing the response of 8 (87 nM) and 35 (>10 µM). Without being bound by a particularly theory, it is believed that a possible explanation for the change in $EC_{50}$ is that both the carbazole moiety and the aromatic moiety attached to the carbonyl impact the positioning of the lipophilic moiety attached to the carbonyl.

Fourth, the relevance of the carbonyl linker in determining the compound's $EC_{50}$ was evidenced by comparing 8 (87 nM) with both 27 (560 nM) and 26 (>10 µM), resulting in 6- and 115-fold increase in $EC_{50}$ values, respectively, possibly due to loss of a hydrogen bond interaction. Specifically, thiocarbonyl derivatives destabilize hydrogen bond formation through higher steric demands that are imposed by both the larger sulfur atom and the lower electronegativity compared with the oxygen atom. By contrast, the carbonyl linker differentially impacted on the maximal anti-tumor killing efficacy, as 27 exhibits a more pronounced maximal killing activity than 8 (67% vs 43%, respectively).

Fifth, the impact of the chain born by the endocyclic nitrogen is evident by comparing the $EC_{50}$ values of the ethyl compound 8 (87 nM) with both the trifluoroethyl compound 18 (5.6 µM) and the propyl compound 16 (>10 µM), corresponding to a 64- and 115-fold increase in the $EC_{50}$ values, respectively. The chain linked to the endocyclic nitrogen appears to have less impact on the maximal killing efficacy: 8 (43%) and 18 (35%). The positioning of the methylnaphthyl moiety appears to also have relevance, as exemplified by the $EC_{50}$ values of 8 (87 nM) and 28 (957 nM); exhibit different activities and yet 28 also exhibits excellent cell killing activity (89%). This result suggests an interaction site between the chain borne by the endocyclic nitrogen of compounds of the disclosure and the target ((i.e. colchicine site of tubulin) to trigger antitumor activity.

Sixth, the $R^1$-position (i.e., position 7) of the carbazole moiety also affects the $EC_{50}$, as suggested by comparing 8 (87 nM) with 31 (2.6 µM), which contains a small methoxy substituent as the $R^1$ group that increases the $EC_{50}$ value by 30-fold. Without being bound to a particular theory, this result suggests that an interaction site between the carbazole and the target exist and might be essential for activity. However, 31 had a greater maximal efficacy at killing T98G cells (72%) compared with 8 (43%). Together, these results show that the potency ($EC_{50}$) and maximal efficacy (% killing) of compounds of the disclosure at killing cancer cells can be mechanistically separated.

Biological Example 2: Killing Activity in Patient-Derived GBM Cells and the Human Liver Cell Line HepG2

Figure 3:
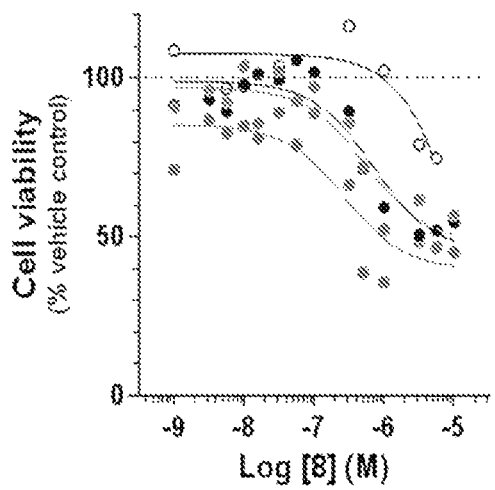
FIG. 3 illustrates cell-killing activity of select compounds of the disclosure in patient-derived glioblastoma cells and HepG2 cells. PD-GBM cells and HepG2 cells in culture were treated with increasing concentrations of compound and cell viability was measured 72 hours following treatment using WST-1. The dotted line shows 100% vehicle control. Data are the mean±SEM of at least three independent experiments performed in triplicate.
Figure 3:
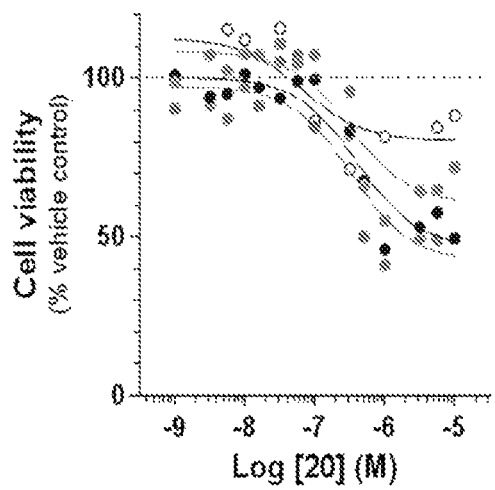
Figure 3:
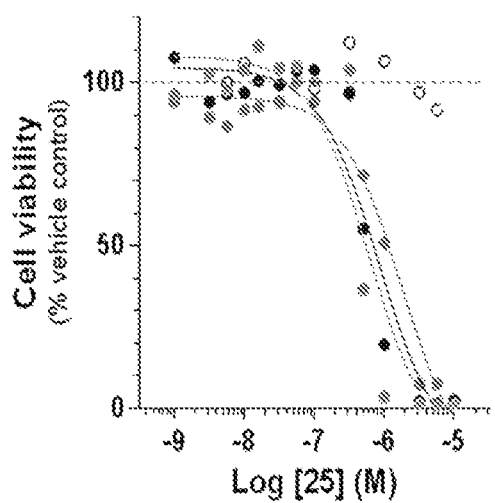
Figure 3:
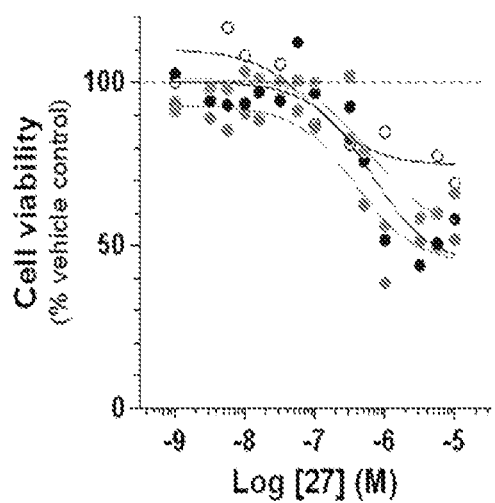

To explore further the therapeutic potential of the compounds of the disclosure, the antitumor activity in human patient-derived GBM (PD-GBM) cells was measured in culture. Specifically, these cells represent a recognized preclinical model system for testing for the efficacy of novel treatments of GBM as they are categorized by their mutation profile in three subtypes (i.e., proneural, mesenchymal and classical) that may differentially respond to treatment. To test for potential liver toxicity, the human liver cell line HepG2, a commonly used cell culture model system, was treated. Therefore, the PD-GBM cells in culture were treated with the four most potent compounds of the disclosure (8, 20, 27 and 25) from the initial screen and found that they kill the PD-GBM cells with $EC_{50}$ and maximal efficacy values that mirrored their activity on T98G cells and remained within similar values irrespective of the subtype (Table 2). These four compounds exhibited lower cell-killing activity in HepG2 cells, reaching only 8-41% maximal efficacy as compared with the PD-GBM cells where the maximal efficacy reached 44-99%. PD-GBM and HepG2 cells in culture were treated with increasing concentrations of compound. Cell viability was measured using WST-1 72 hours after treatment. $EC_{50}$ values were calculated using Prism® software using the curves shown in FIG. 3. Maximal killing activity was measured at 5.6 µM. Data are the mean of at least three independent experiments performed in triplicate. Not converged (NC).

Table 2. Cell-killing activity in patient-derived GBM and liver HepG2 cells.

TABLE 2

Cell-killing activity in patient-derived GBM and liver HepG2 cells.

| | Cell Killing Activity | | | | | | | |
|---|---|---|---|---|---|---|---|---|
| | PD-GBM (proneural) | | PD-GBM (classical) | | PD-GBM (mesenchymal) | | HepG2 (liver) | |
| Comp. | $EC_{50}$ (nM) | maximal killing (% ± SEM) | $EC_{50}$ (nM) | maximal killing (% ± SEM) | $EC_{50}$ (nM) | maximal killing (% ± SEM) | $EC_{50}$ (nM) | maximal killing (% ± SEM) |
| 8 | 542 | 53.3% ± 10.9 (at 5.6 µM) | 698 | 47.9% ± 6.5 (at 3 µM) | 268 | 64.3% ± 1.3 (at 1 µM) | 1689 | 25.0% ± 3.8 (at 5.6 µM) |
| 20 | 316 | 44.8% ± 10.5 (at 1 µM) | 407 | 53.9% ± 4.2 (at 1 µM) | 335 | 58.9% ± 1.4 (at 1 µM) | 66 | 28.6% ± 13.9 (at 0.6 µM) |
| 25 | 613 | 98.9% ± 0.1 (at 5.6 µM) | 846 | 98.6% ± 0.9 (at 5.6 µM) | 1823 | 97.2% ± 0.8 (at 10 µM) | NC | 8.3% ± 8.5 (at 5.6 µM) |
| 27 | 630 | 44.0% ± 14.2 (at 1 µM) | 633 | 56.0% ± 3.8 (at 3 µM) | 386 | 50.6% ± 6.2 (at 3 µM) | 101 | 30.8% ± 13.3 (at 10 µM) |

The sensitivity of GBM to the compounds of the disclosure compared with HepG2 suggests a promising therapeutic index (i.e., the ratio of the amount of agent that causes the therapeutic effect to the amount that causes toxicity). Compound 25 demonstrated a killing of 95-100% of the PD-GBM cells when applied at 1-10 µM while remaining inactive at these concentrations in HepG2 cells (Table 2 and FIG. 3). Another advantage of the compounds of the disclosure is that they kill all PD-GBM subtypes independent of their genetic make-up. This addresses one of the extensively highlighted issues concerning the selectivity of targeting GBM tumors, which are known to rapidly become heterogeneous in their genetic make-up, often encompassing all subtypes (proneural, mesenchymal and classical). Therefore, the equally potent and efficacious killing activities of the compounds of the disclosure measured in PD-GBM subtypes shows their potential to kill the majority of GBM cells forming the heterogeneous tumor mass.

Figure 4:
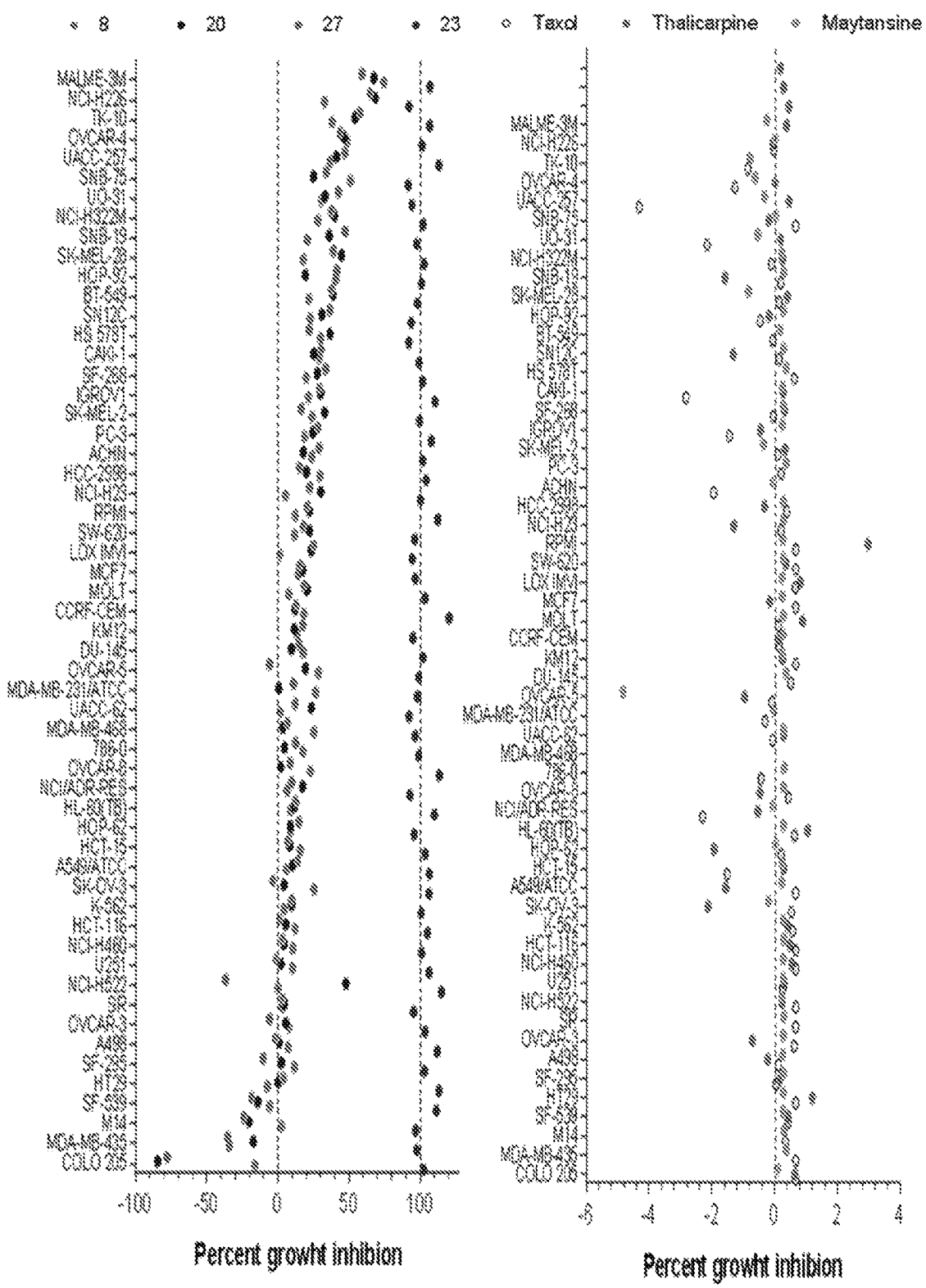
FIG. 4 illustrates analysis of cell-killing activity of select compounds of the disclosure in NCI-60 cancer cell line panel. 8, 20, 27 and 23 (left panel) and taxol, thalipcarpine, and maytansine activity (right panel) in the NCI-60 cell lines. Drugs are applied at 10 µM and both inhibition of cell proliferation (% growth inhibition positive values) and cell killing activity (% growth inhibition negative values) are measured after 48 hours. For both Y axes, cell lines were rank ordered according to the average cell killing activity of 8, 20 and 27; from the least sensitive cancer cell line, MALME-3M (top) to the most sensitive cancer cell line, COLO-205 (bottom).
Figure 5:
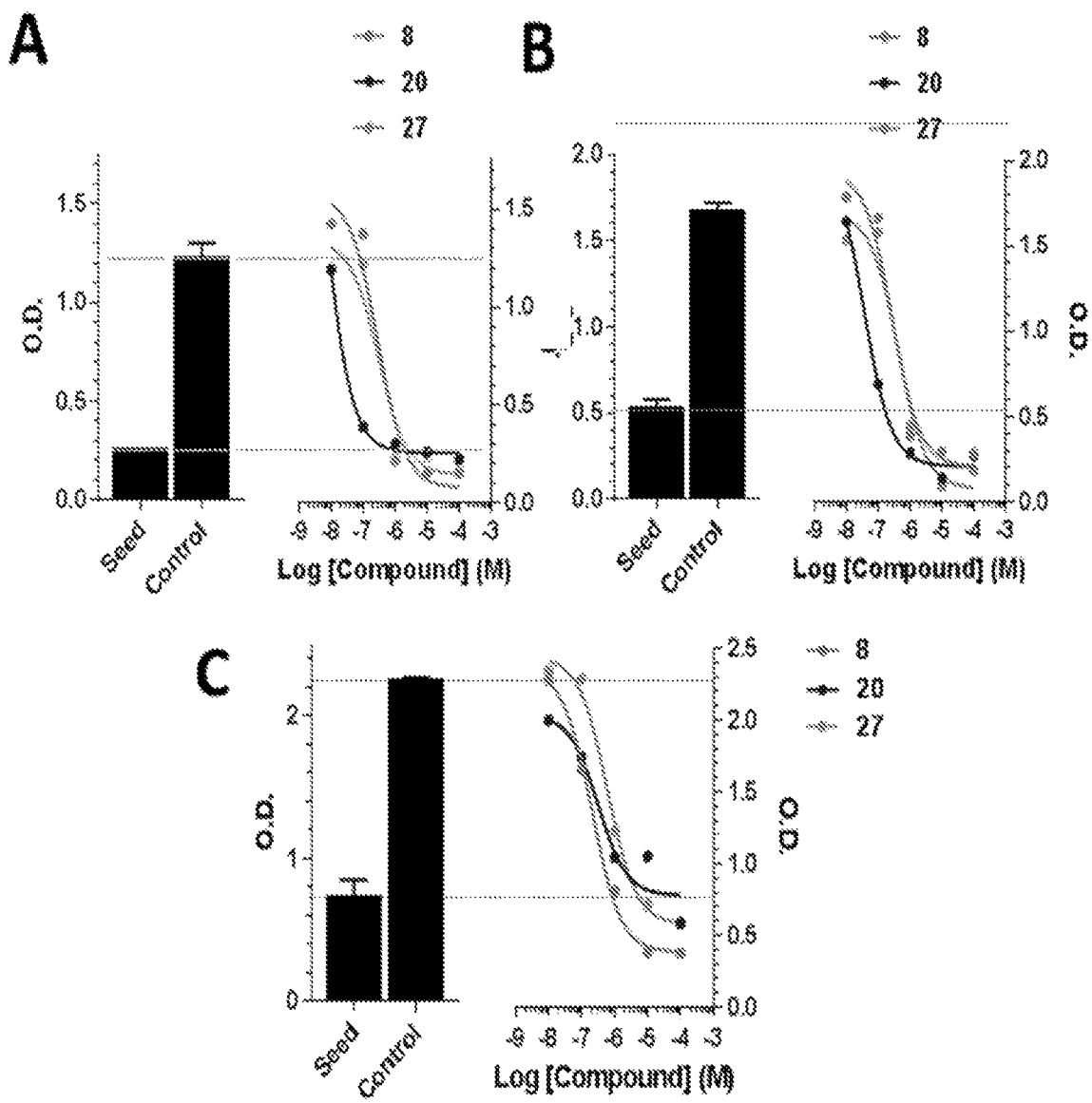
FIG. 5 illustrates cell-killing activity of 8, 20 and 27 in HT-29, Colo205 and HCC-2998 colon NCI-60 cell lines in culture. A: HT29 cells in culture, B: Colo-205 cells in culture and C: HCC-2998 cells in culture were treated with increasing concentrations of compounds 8, 20 and 27. Cell viability was measured 48 hours following treatment using Alamar blue and is expressed as optical density (O.D.). Data are gathered at seeding and after 48 h, providing an index of the inhibition of cell proliferation (between both dotted lines) and triggering of cell death (below Seed dotted line). D: table showing compounds, origin and name of cell line, and parameters of cell-killing activity ($GI_{50}$, Total Growth Inhibition (TGI) and $LC_{50}$).
Figure 6:
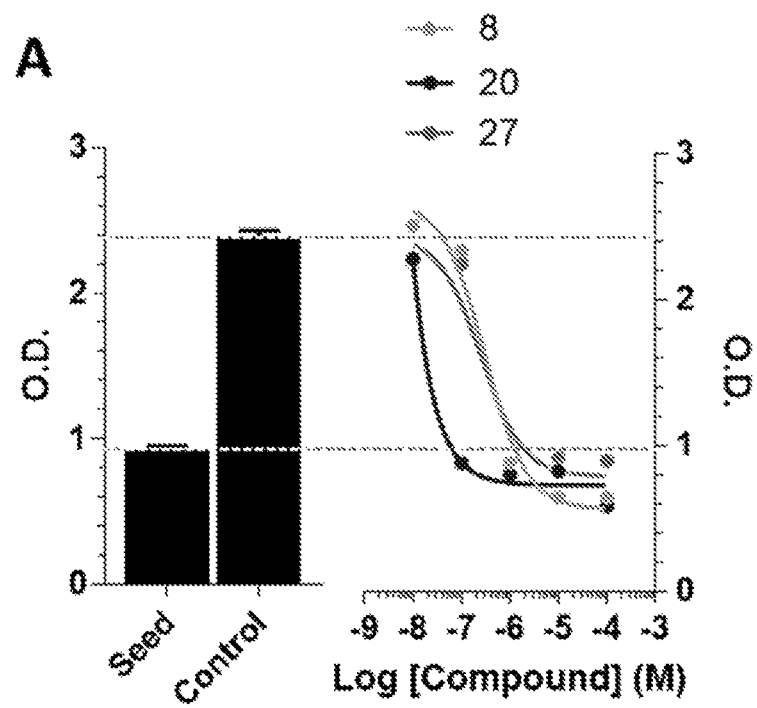
FIG. 6 illustrates cell-killing activity of select modified-carbazoles in SF-539 and SF-295 GBM cells in culture. A: SF-539 cells in culture and B: SF-295 cells in culture were treated with increasing concentrations of compounds 8, 20 and 27. Cell viability was measured 48 hours following treatment using Alamar blue and is expressed as optical density (O.D.). Data are gathered at seeding and after 48 h, providing an index of the inhibition of cell proliferation (between both dotted lines) and triggering of cell death (below Seed dotted line).
Figure 6:
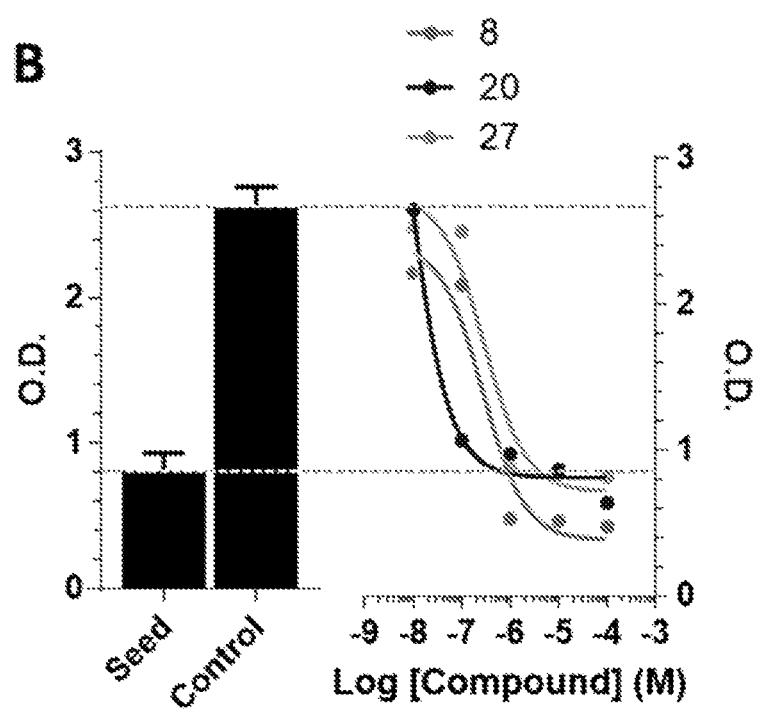

Biological Example 3: Cell-Killing Activity and MOA in the NCI-60 Cancer Cell Line Panel The Developmental Therapeutics Program's NCI 60 cell screen was utilized to study the differentiating MOA by which the three most potent compounds of the disclosure: 8, 20 and 27, and the inactive analogue 23 might kill cancer cell lines. This screening platform measures the antitumor activities of compounds expressed as percent growth inhibition, which differentiates the compound's activity at inhibiting cell proliferation and reducing cell number (i.e. killing cells). The compound 23 did not significantly affect the proliferation and viability of any of the cell lines (growth inhibition: mean 102.05; delta 10.42, and range 28.77) (FIG. 4). By contrast, the three active compounds 8, 20 and 27 significantly reduced the proliferation of 41 cell lines (from 67% to 10% percent growth inhibition), halted the proliferation of 11 cell lines (from 9% to −1% growth inhibition) and killed 4 cell lines (13% to 60% loss in cell number) (FIG. 4). Two GBM cells lines included in the NCI-60 panel, SF-295 and SF-539, were among the top ten cell lines that were the most sensitive to 8, 20 and 27 treatments (FIG. 6). Their respective $EC_{50}$ values of the compounds measured in these cells mirrored their $EC_{50}$ values measured in T98G cells. Additional cell lines among the top ten cell lines that were sensitive to these three compounds were three cell lines of colon cancer origin: Colo205, HT-29 and HCC-2998 (FIG. 5).

The COMPARE and CellMiner web applications allow for the statistical analysis of the antitumor activities of drugs tested in the NCI-60 cell line panel, and allow identification of compounds that similarly impact the proliferation and viability of NCI 60 cells. Using these applications, three MTAs (paclitaxel, thalicarpine and maytansine) were found among the top eight compounds that exhibit antitumor activities tested in the NCI-60 cell line panel that correlate with the antitumor activities of 8, 20 and 27. While this result suggests that 8, 20 and 27 kill cancer cells by disrupting MTs, the respective correlation parameters were relatively low, pointing to a somewhat different MOA as compared to that of paclitaxel, thalicarpine and maytansine, and all other MTAs tested in this platform. Based on these results, it was reasonable to expect that the compounds of the disclosure would interact with tubulin or MTs through a different MOA.

Biological Example 4: Activity of Compounds of the Disclosure with Tubulin and Microtubules First, it was determined whether compounds of the disclosure compete for [$^3$H]colchicine binding to native purified tubulin as previously described. Colchicine binding to tubulin and tubulin assembly (as assessed by turbidity development of tubulin solutions) were inhibited in a dose dependent manner by combretastatin A-4 (1) and nocodazole (3) (positive controls) and by the selected compounds of the disclosure. In this assay, 1 (5 μM) and 3 (5 μM) competed for binding by 98% and 74%, respectively (Table 3). Results are the mean±standard deviation (SD) of at least three independent experiments. MT and free tubulin partitioning was shifted toward free tubulin by all compounds indicating MT destabilization. $EC_{50}$ values are the results from representative experiments that were repeated three times with comparable results. Not determined (ND).

Table 3. Activity of selected compounds of the disclosure with tubulin and microtubules.

TABLE 3

Activity of selected compounds of the disclosure with tubulin and microtubules.

| Comp. | Colchicine Binding % inhibition (mean ± SD) | | Tubulin Assembly $IC_{50}$ (μM) | MT-Tubulin Partitioning |
|---|---|---|---|---|
| | at 5 μM | at 1 μM | (mean ± SD) | $IC_{50}$ (μM) (mean) |
| 1 | 98 ± 0.1 | 89 ± 3 | 0.64 ± 0.01 | 0.6 |
| 3 | 74 ± 0.8 | 23 ± 0.8 | 0.48 ± 0.01 | 2.4 |
| 23 | 4 ± 1 | ND | >20 | >20 |
| 25 | 41 ± 4 | ND | 4.4 ± 0.4 | 5.3 |
| 8 | 53 ± 3 | ND | 1.4 ± 0.2 | 2.1 |
| 27 | 70 ± 1 | ND | 1.6 ± 0.01 | 6.4 |
| 20 | 91 ± 1 | 61 ± 4 | 0.89 ± 0.04 | 3.4 |

Under these experimental conditions, compounds of the disclosure competed for colchicine binding with increasing affinity (23<<25<8<27<20) that mirrored their respective $EC_{50}$ values at killing GBM cells. Next tested was their ability to inhibit the assembly of purified tubulin using an in vitro turbidity assay as previously described. In this assay, where tubulin is present at 10 μM in 0.8 M glutamate with 0.4 mM GTP and the extent of assembly is measured after 20 min at 30° C., 1 and 3 have $IC_{50}$ values of 0.6 μM and 0.5 μM, respectively (Table 3). Under these experimental conditions, 8, 20 and 27 exhibited $IC_{50}$s of 1.4, 0.9 and 1.6 μM, respectively, and 23 was inactive at concentrations up to 20 μM (Table 3). To build on these results, the ability of compounds of the disclosure to influence the partitioning of MT dimers and polymers, an index of MT assembly and disassembly as previously described, was measured. In this assay, compounds are incubated with sheared MTs at 37° C. and the resulting amounts of tubulin dimers (free tubulin) and polymer (MT) after 15 min is measured on polyacrylamide gels. Under these experimental conditions, 1 and 3 have $IC_{50}$s of 0.6 and 2.4 μM, respectively; 8, 20 and 27 have $IC_{50}$ values of 2.1, 3.4 and 6.6 μM, respectively; and 23 was inactive when tested up to 20 μM (Table 3). Thus, the $IC_{50}$ values of these compounds of the disclosure to bind to the colchicine site on tubulin parallels their $EC_{50}$ values to kill GBM cells, whereas their $IC_{50}$ values to trigger MT disassembly does not correlate as well and remained in the micromolar range as measured in two in vitro assays.

The analysis of the structure-activity relationships (SARs) of compounds of the disclosure to bind to the colchicine site, disrupt MT assembly and favor disassembly provide initial mechanistic insights on how their binding to the colchicine site in tubulin might favor conformational changes in this protein that might affect MT dynamics. The potency of compounds of the disclosure is in the micromolar range when affecting MT assembly and disassembly. A possible explanation is that the affinity of compounds of the disclosure for the colchicine site depends on specific interactions with a subset of amino acid within the binding pocket, whereas the conformational changes in tubulin that are stabilized by the compounds of the disclosure are only reached at high concentrations. Thus, the compounds of the disclosure may represent new chemical tools to study how binding to the colchicine site might affect tubulin conformation and how this affects MT end dynamics.

Biological Example 5: Gas Phase Pharmacophore Study

Figure 7:
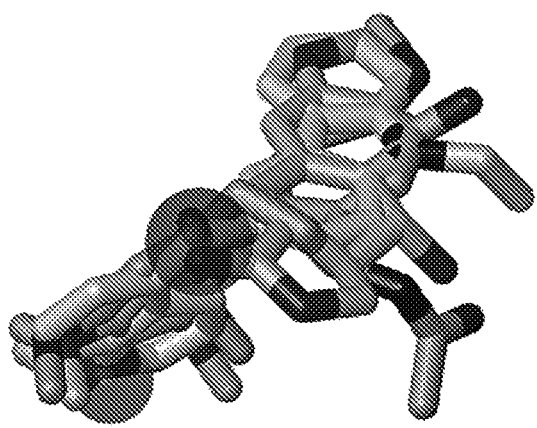
FIG. 7 illustrates gas phase pharmacophore overlap model of colchicine, podophyllotoxin, and 20. Panel A illustrates a three-dimensional stick rendering of the gas phase pharmacophoric overlap model for colchicine (carbons in medium gray), podophyllotoxin (carbons in gray), and 20 (carbons in very light gray). For purposes of visual clarity, oxygen atoms are colored dark gray in podophyllotoxin and deeper red for both colchicine and 20. In all three structures, nitrogen atoms are colored black. The light gray circles correspond to the two 20 polar hydrogen bond acceptor features in common with colchicine or podophyllotoxin. Panels B, C and D are two-dimensional illustrations of the pharmacophore overlap model depicted in Panel A. Panel B illustrates colchicine. Panel C illustrates podophyllotoxin and Panel D illustrates 20. In Panels B-D, the bolded black atoms correspond to the steric overlaps of the colchicine and podophyllotoxin atoms that are in common with 20; otherwise, atoms in Panels B-D are colored medium gray for colchicine, medium gray for podophyllotoxin and light gray for 20. As with Panel A, the gray circles in Panels B-D correspond to polar hydrogen bond acceptor features of compound 20 that are in common with colchicine or podophyllotoxin.
Figure 7:
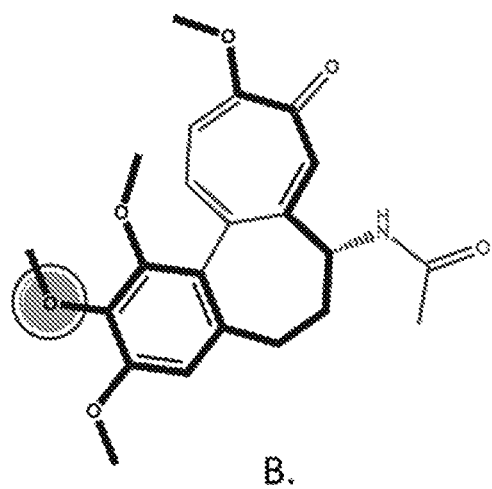
Figure 7:
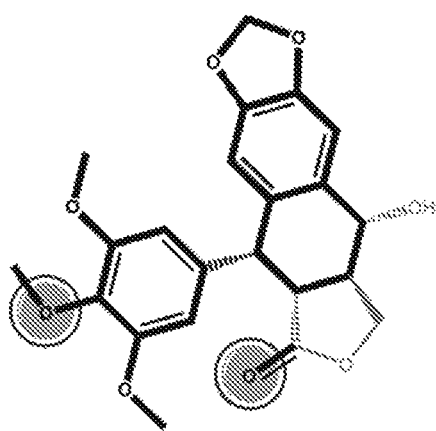
Figure 7:
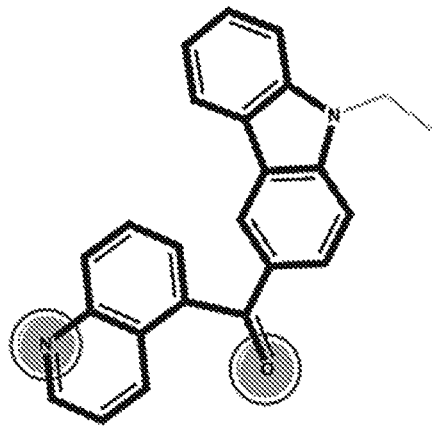

To understand the structural basis of the MT disrupting and antitumor activity of the compounds of the disclosure, a gas phase study was initiated to determine common pharmacophoric features with sterically-relevant colchicine site agent. The structure of 20, the most potent of the series to bind to the colchicine site, was used to compare complementary features and volumetric space filling models of ligand co-crystal structures that currently exist in the Protein Data Bank (PDB) for the colchicine site on tubulin. Two MTAs that target the colchicine site, colchicine and podophyllotoxin, were found to have the most steric, hydrophilic and hydrophobic spatial similarity with the carbazole analogues. Using methodology employed previously, the X-ray based configurations and conformations of the two chiral molecules (colchicine and podophyllotoxin, taken from the X-ray co-crystals 402B, and 1SA1, respectively) were employed as templates for the translational and conformational overlap modeling of 20. FIG. 7 displays the results of the gas phase pharmacophore overlap study for colchicine, podophyllotoxin and 20.

The results from the gas-phase pharmacophore overlap study identified the common steric features between 20, podophyllotoxin and colchicine. The atoms of 20 are almost completely subsumed within the steric space of podophyllotoxin and approximately 80% of the steric space of colchicine. The common steric overlap between these three molecules is largely composed of hydrophobic atoms. However, the two key polar atoms of 20 are the basic quinoline N and its ketone O. The quinoline N atom of 20 shows remarkable spatial consistency with the central methoxy oxygen atoms of the trimethoxylated-aryl moieties of podophyllotoxin and colchicine (FIG. 7), whereas the ketone oxygen atom of 20 is isosteric with the lactone carbonyl of podophyllotoxin. Unique to the 20 scaffold is the relatively strong hydrogen bond acceptor quinoline N in spatial proximity to the comparatively much weaker hydrogen bond accepting ether oxygen atoms of podophyllotoxin and colchicine. Furthermore, the 10-membered aromatic quinoline ring system of 20 offers unique topology to satisfy the binding requirements of the subsite normally occupied by the trimethoxylated-aryl systems of podophyllotoxins and colchicine. An additional unique feature of the 20 scaffold is the ethyl moiety attached to the carbazole N (FIG. 7). The consistent polar, hydrophobic and steric overlap identified by the gas phase pharmacophore study provides a template to conduct molecular docking studies to determine a detailed, all-atom rationalization of the compounds of the disclosure' structure activity relationships in the colchicine site.

Biological Example 6: Molecular Docking Studies

Given the close steric congruency with podophyllotoxin, the alpha and beta tubulin subunits of the recently solved 2.30 Å co-crystal of the podophyllotoxin analogue: 4β-(1, 2,4-triazol-3-ylthio)-4-deoxypodophyllotoxin (PDB entry code=5JCB) were employed as the initial geometry to conduct the molecular docking studies of the compounds of the disclosure series. Maestro protein preparation tools (utilizing the OPLS force field) were utilized for X-ray co-crystal comparisons and to prepare the structure for molecular mechanics energy refinement simulations. The 5JCB coordinates were optimized in a stepwise fashion (hydrogens first, followed by side chain and backbone) resulting in an all-atom energy-refined structure used as the starting structure for the carbazole molecular docking studies. Superimposition of the 5JCB X-ray coordinates onto the resulting energy refined structure revealed only a 0.98 Å RMS deviation between the 13,646 heavy atoms. Of the 6880 backbone atoms compared, only a 0.74 Å deviation was observed. These data signify that very close geometries were obtained between the X-ray and energy refined structures that are well within the expected thermodynamic variation and resolution of the 2.3 Å 5JCB X-ray structure.

Figure 8:
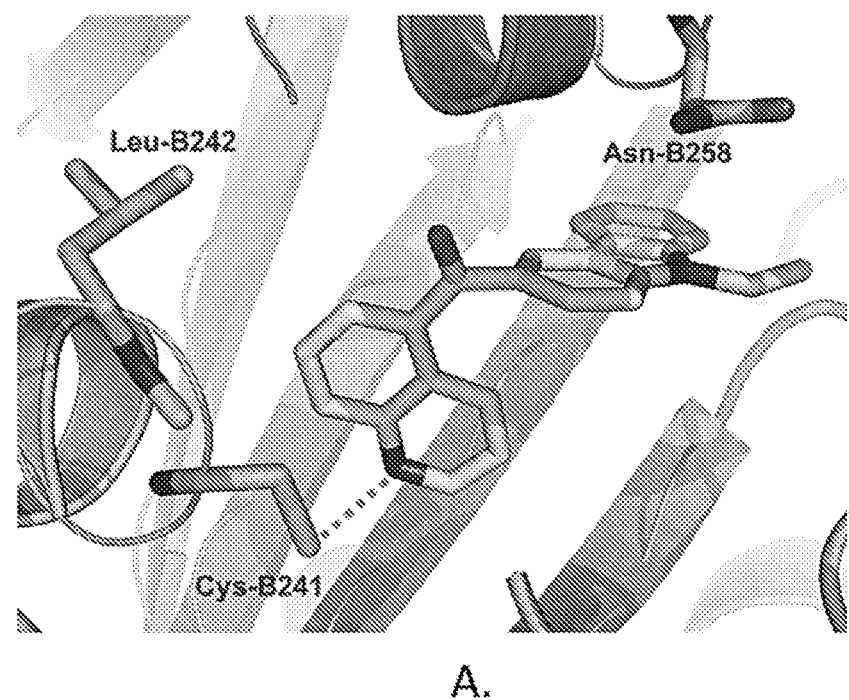
FIG. 8 illustrates comparison of modeling and X-ray poses. Panel A displays the view of the optimized 20 (carbons in light gray) in the colchicine site from the molecular docking studies. In Panel B, the pose of the podophyllotoxin-triazole analog (carbons in dark gray) from the X-ray 5JCB is shown with 20 overlapped from molecular docking studies. In addition to the high degree of steric congruency with the podophyllotoxin-triazole analog, the ketone oxygens of both 20 and podophyllotoxin-triazole are isosteric. Unique to 20, compared to podophyllotoxin and colchicine, is the relatively strong hydrogen bond acceptor quinoline N located in the trimethoxy-aryl subsite (near β-Cys-241). 20 can form a direct hydrogen bond (blue dashed lines in both panels) with the side chain S—H of β-Cys-241. The quinoline N of 20 can form a stronger hydrogen bond with a water bridge to polar backbone atoms compared to the ether oxygen atoms of the central methoxy groups of podophyllotoxin and colchicine.
Figure 8:
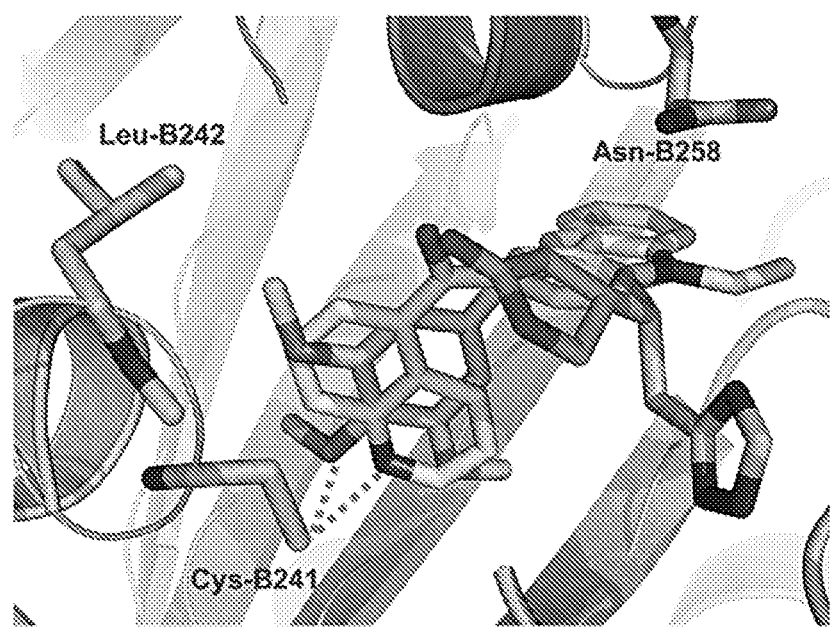

Carbazole structures were built and initially optimized with the MM2 force field and transferred into the cff91/cvff force fields for potential assignment. For molecular docking studies, methodology employed previously with added refinements was used. Briefly, the carbazoles were docked into the energy refined 5JCB X-ray co-crystal structure to examine all translation and rotational steric complementarity between the most potent ligand of the carbazole series, 20, its conformational isomers, and the side chains of the energy-refined podophyllotoxin binding site. The resulting all-atom model was derived from iterative constrained optimizations to refine a maximum complementarity between the atoms of 20 and its contacts with the amino acid side chains of the colchicine site. FIG. 8 shows the optimally docked conformation of 20 and its overlap with the triazole-podophyllotoxin analogue in the model.

Figure 9:
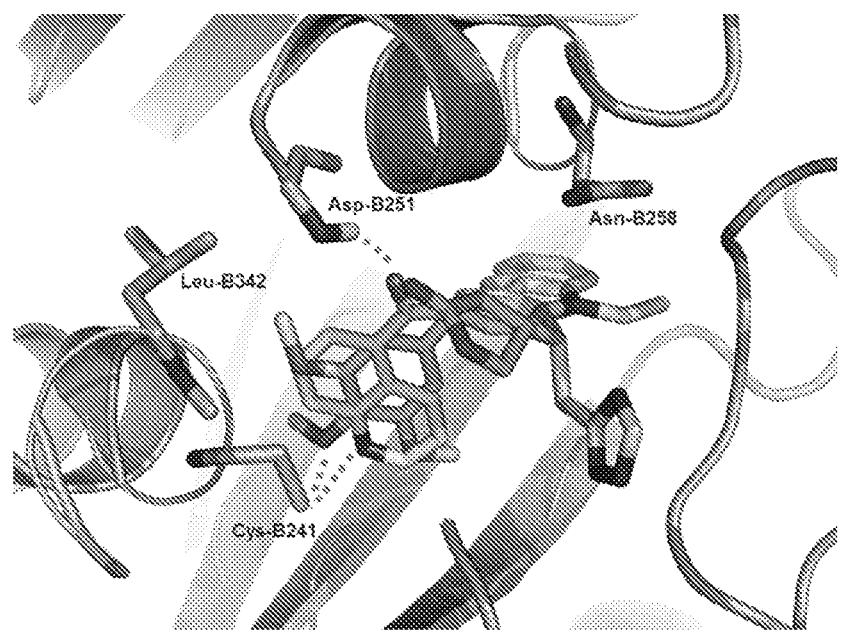
FIG. 9 illustrates view of the optimized 20 (carbons in light gray) in the colchicine binding site overlapped from the podophyllotoxin-triazole (carbons in light gray) analog as the result of the molecular docking study. In addition to the high degree of steric congruency with the podophyllotoxin-triazole analog, the ketone oxygen key polar group can form a direct hydrogen bond (dark colored dashed lines) with the backbone N—H of Asp B251 or via a water bridge. The quinoline N of 20 can also form a much stronger hydrogen bond with the b-Cys-241 side chain or form hydrogen bonds through a water molecule as does the ether oxygen atom of the podophyllotoxin-triazole.
Figure 10:
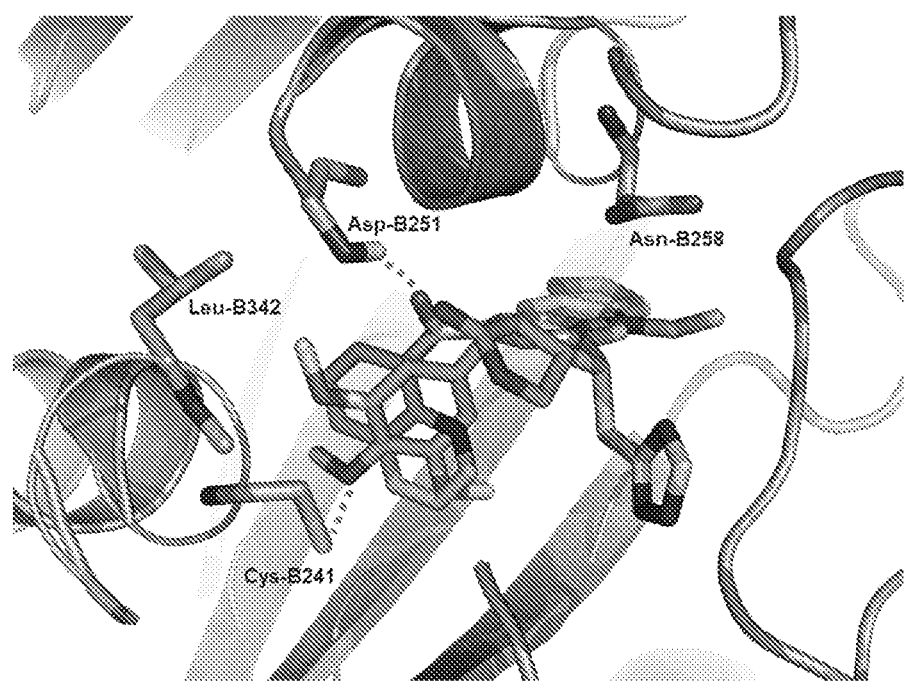
FIG. 10 illustrates view of the optimized 22 (carbons in dark gray) in the colchicine binding site overlapped with the podophyllotoxin-triazole (carbons in light gray) analog as the result of the molecular docking study. In addition to the high degree of steric congruency with the podophyllotoxin-triazole analog, the ketone oxygen key polar group can form a direct hydrogen bond (dark colored dashed lines) with the backbone N—H of Asp B251 or via a water bridge. However, in this case quinoline N of 22 is in the 5 position, and therefore cannot form a hydrogen bond with the b-Cys-241, accounting for a significant loss in activity.

An overlap that includes colchicine can be found in FIGS. 9 and 10. The optimally docked model of 20 served as a template for molecular docking studies with the rest of the carbazole series to rationalize the protein-atom ligand contacts' SARs. Constrained optimizations were performed in an iterative fashion to eliminate bad contacts and biochemically unfeasible hydrophobic-polar interactions as identified by the HINT program. When available, the in vitro binding data were prioritized to rank-order the carbazoles; otherwise the percent inhibition of the rank-ordered congeneric series served as the biological activity data for the SAR. A total of twenty structures (including the R and S enantiomers of 27) provided a structure-based explanation that rationalized the SAR of the carbazole series.

The compounds of the disclosure described herein exemplify a new chemotype for tubulin depolymerizers that interact at the colchicine site. The modeling studies indicate that the 20 scaffold is almost entirely subsumed by the steric space of podophyllotoxin and approximately 80% within the steric space of colchicine. Potent carbazoles bind more efficiently (requiring fewer atoms) in the same steric space than podophyllotoxin because of the conformational restriction imposed by the 13-membered (carbazole) and 10-membered (quinoline/napthalene) rings systems when both are bridged by a methanone. The methanone carbonyl, which functions as a strong hydrogen bond acceptor, is important for potent activity in the carbazole series, as evidenced by a substantial loss of activity when the carbonyl is replaced by a thiocarbonyl (26). Thus, 26 forms a weaker hydrogen bond r and imposes the bulkier S atom in the sterically restricted space where the lactone carbonyl oxygen atom of podophyllotoxins and carbazole oxygen atoms overlap.

Figure 11:
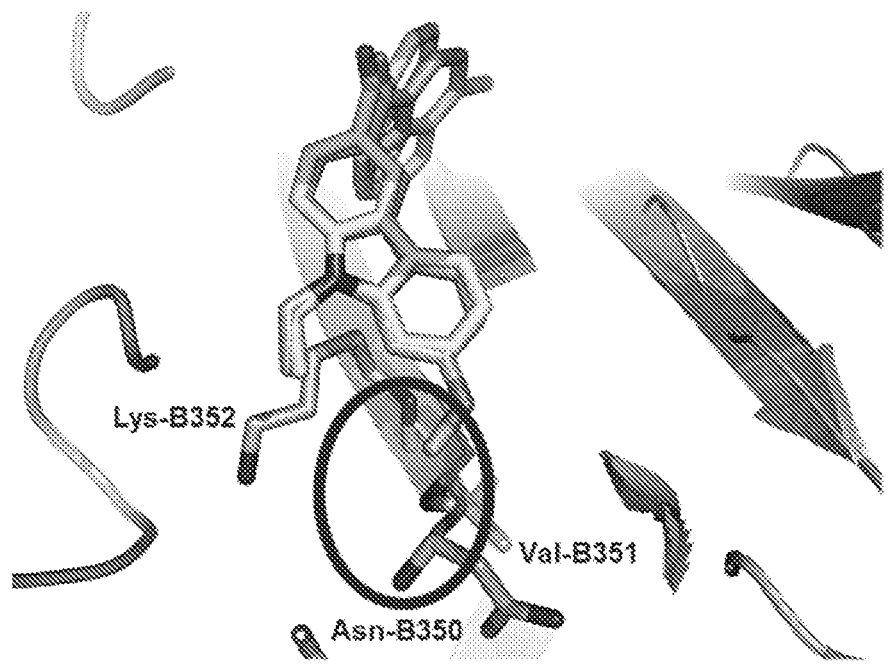
FIG. 11 illustrates view of the optimized 20 in conformational and docking studies. Panel A displays a view of the optimized 20 (carbons in light gray), and the 7-methoxylated analog (31) (carbons in medium gray), overlapped in the energy-refined X-ray (5JCB) structure from molecular docking studies. The dark oval highlights the region where the methyl component of the methoxy may form unfavorable hydrophobic-polar contacts with the polar backbone N—Hs of residues Lys-B352, Val-B351 and Asn-B350. At the same time, the ethyls attached to the carbazole Ns make highly favorable hydrophobic contacts with hydrocarbon component of the Lys-B352 side chain. Panel B illustrates unfavorable hydrophobic-polar interactions (dark oval) with the s, ide chain of Lys-B352 when 1) the carbazole N is substituted with the bulkier propyl (16: carbons in magenta) due to its close proximity with the cationic $NH_3$ and 2) the polar trifluoromethyl group of 18 (carbons in medium gray) due to its close proximity to the hydrocarbon component of the Lys-B352 side chain.
Figure 11:
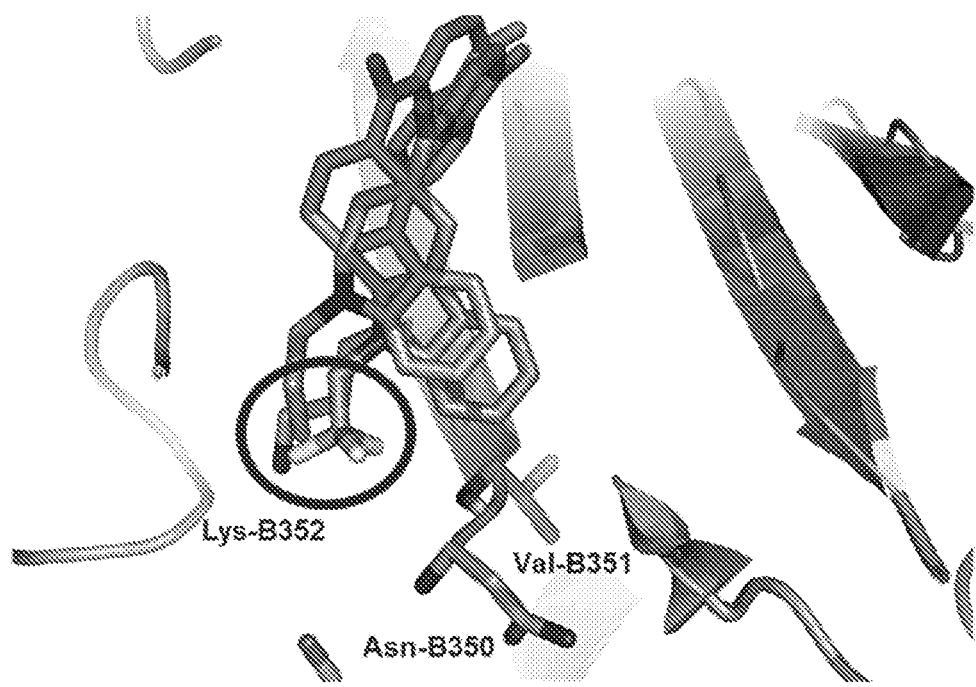

Although most of the atoms that are sterically congruent with podophyllotoxin and colchicine are hydrophobic, 20 introduces several unique structural elements to its colchicine site interactions. 20 poses a 10-membered quinoline aromatic ring system in the colchicine subsite normally occupied by the colchicine/podophyllotoxin trimethoxy-aryl system. With respect to enthalpic interactions, two hydrogen bond acceptors: the methanone oxygen atom, and the quinoline nitrogen atom account for most of the potency of 20. Specifically, the methanone oxygen atom can hydrogen bond with the backbone N—H of β-Asp-251, and the quinoline nitrogen atom located at the 5 position enables the formation of a strong can hydrogen bond with the S—H of β-Cys-241) (FIG. 9). Perhaps this occurs as the tubulin dimers polymerize and could therefore play a significant role in the prevention of MT assembly. By contrast, 22 possesses the quinoline nitrogen atom in the 8 position which greatly reduces activity due to its inability to form the hydrogen bonds characteristic of 20, podophyllotoxin, and colchicine (FIG. 10). The modeling studies indicate that the 8-quinoline nitrogen atom enables the formation a water-mediated intramolecular hydrogen bond that stabilizes a sterically-dissimilar conformation from both 20 and podophyllotoxin, which potentially also contributes to a loss of activity. Removal of the nitrogen atom altogether (as in in 8) to form a naphthalene, also reduces activity due to the loss of the hydrogen bonding nitrogen atom altogether. The docking studies further indicate that the 4-methyl group of 8 forces the naphthalene deeper into the trimethoxy-aryl subsite to avoid unfavorable hydrophobic-polar contacts with backbone polar atoms. This then places the methanone oxygen atom slightly further from the ketone oxygen atom in 20's optimal orientation. The net effect is that 8's methanone oxygen atom is less conformationally available to function as a strong hydrogen bond acceptor. This is also supported by 8's close congener 14, which only differs structurally by the lack of the methyl at the napthalene 4 position, and 14 is markedly less active due to loss of a hydrogen bond acceptor. Conversely, adding a hydrophobic bulk to the carbazole ring system reduces activity, as exemplified by the 7-methoxy substituted carbazole of 31 where the methyl portion of its methoxy forms unfavorable hydrophobic-polar contacts with the backbone N—H atoms of β-Lys-352, β-Val-351-349 and β-Asn-350 (FIG. 11, Panel A). A second unique structural feature of the most potent analogue 20 is the ethyl group attached to the carbazole. Both conformational analysis and docking studies indicate that this ethyl group helps stabilize the scaffold's conformation through steric hindrance during binding. An additional attribute of the ethyl group is that it forms favorable hydrophobic contacts with the aliphatic component of the β-Lys-352 side chain (FIG. 11, Panel A). Accordingly, the less active compound 18, in which the hydrophobic distal carbon of the ethyl is replaced with an isosteric polar trifluoromethyl group, is closer to the hydrocarbon component of β-Lys-352 side chain (FIG. 11, Panel B). Moreover, replacement of this ethyl group with a bulkier hydrophobic propyl group (as with 16) reduces activity because of unfavorable hydrophobic-polar liabilities with the cationic $NH_3$ of the β-Lys-352 side chain (FIG. 11, Panel B).

Figure 12:
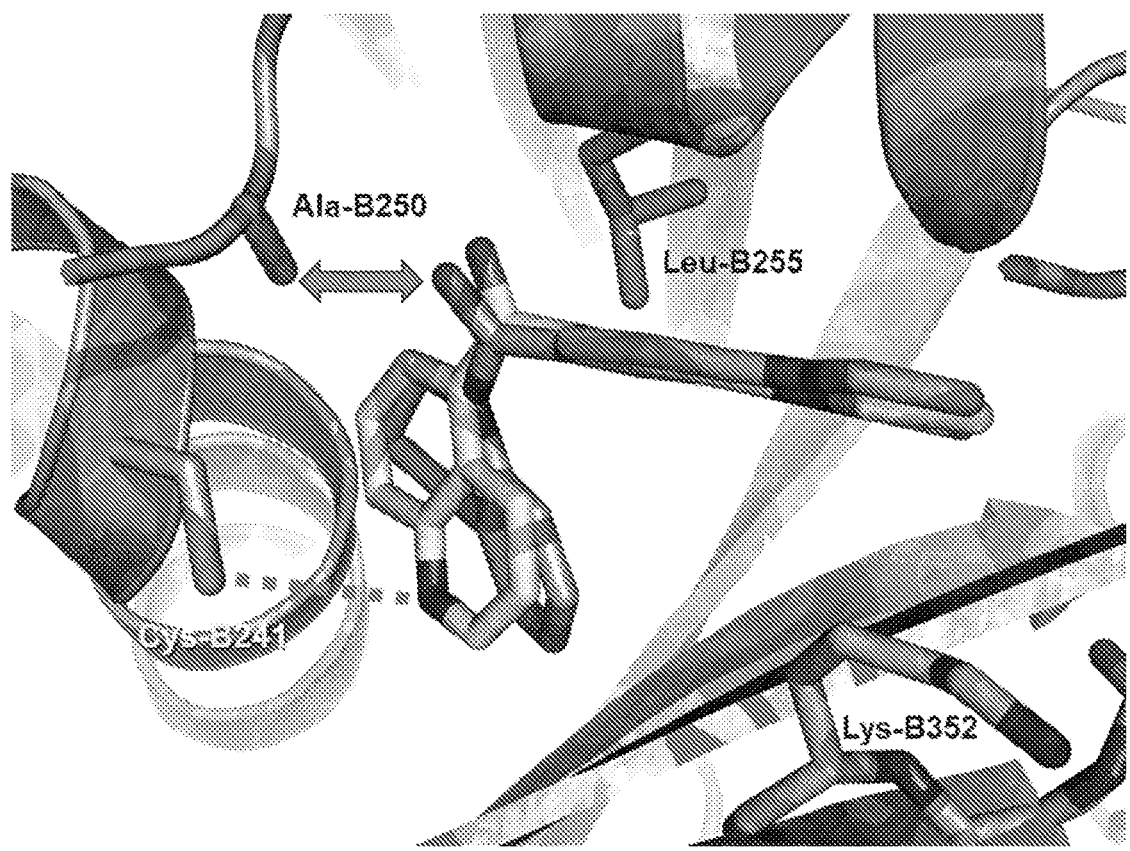
FIG. 12 illustrates a view of 20 (carbons in medium gray) and 25 (carbons in medium gray) overlapped in the energy-refined X-ray (5JCB) structure from molecular docking studies. The rigidity of the amide-like oxygen atom in 25 orients it towards the Ala-B250 side chain creating a hydrophobic-polar liability (gray double arrow) relative to the optimally placed methanone oxygen atom of 20. Also shown is the hydrogen bond acceptor quinoline N of 20 interacting with the side chain of Cys-B241 (gray dashed line). A lack of a hydrogen bond acceptor in this vicinity for 25 also contributes to its reduced activity.

Compound 25 features a 10-membered system linked to the methanone by a nitrogen atom. Since it is a non-planar dihydroquinoline derivative, it also lacks ring aromaticity in this part of the molecule. There are several possible explanations for the reduced activity of 25. First, it could be due to the formation of a more rigid amide-like linkage that produces a less optimal orientation of the hydrogen bond accepting oxygen atom due to the rigidity of the amide. Second, it could be due to the bulkier unsaturated ring that induces a twisted binding mode that potentially introduces an unfavorable hydrophobic-polar interaction liability near the side chain group of β-Ala-250. Third, it could be due to a loss of a hydrogen bond with β-Cys-241 (FIG. 12).

Several conclusions can be drawn from several less active compounds. For example, a feature to highlight is how removal of one the aromatic rings from the naphthalene/quinoline systems of the carbazoles reduces activity. Specifically, despite its p-tolyl methyl group, the single ring of 12 sterically occupies almost half of the trimethoxy-aryl subsite compared with colchicine, podophyllotoxins and 20 and yet it is less potent. An implication for this finding could be that binding to the colchicine site has a minimum steric requirement of occupation at the trimethoxy-aryl subsite to incur significant activity. However, replacement of the 10-membered ring with a 6-membered ring (as in 12 and 10) also increases the number of conformational isomers, which reduces conformational access compared to the more active carbazoles possessing double aromatic ring systems. Another example is 13, which also loses activity by reducing conformational access while increasing conformation isomerism as it extends the single ring linkage to the methanone by a methylene group. Thus, replacement of the p-tolyl methyl of 12 with a hydrophobic and isosteric Cl atom (as in 10) reduces activity by introducing similar disadvantages. The poor activity of 9 is due to the presence of a positive charge introduced by the likely protonated piperazinyl single ring system, reinforcing the finding that the trimethoxy-aryl subsite favors hydrophobic occupation with carefully positioned hydrogen bond acceptors. Accordingly, both 23 and 24 contain hydrogen bond donating N—Hs that are potentially charged.

Figure 13:
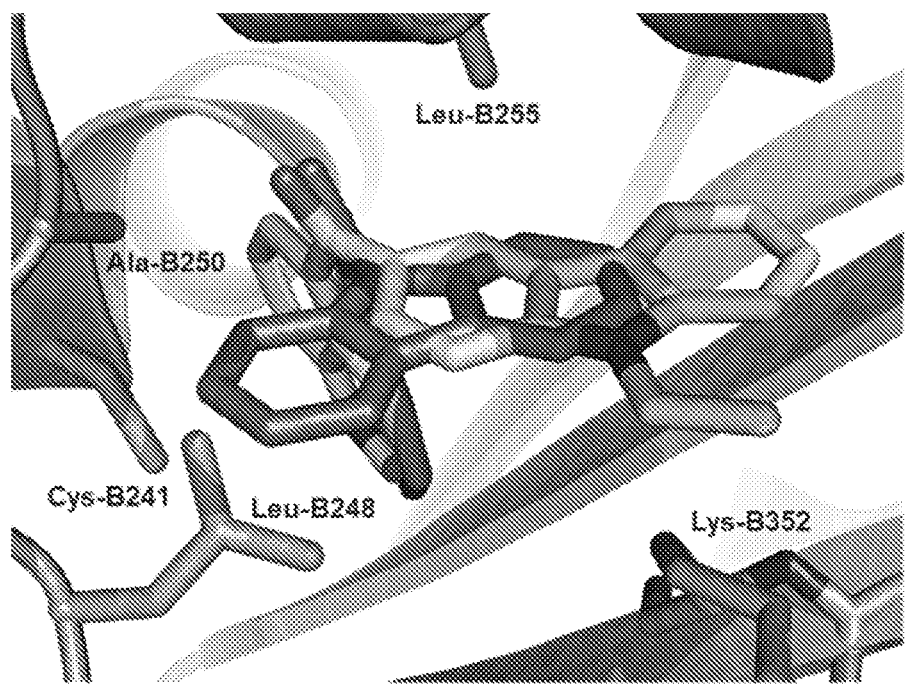
FIG. 13 illustrates view of the optimized 20 in conformational and docking studies. Panel A displays of 20 (carbons in light gray) overlapped with 28 (carbons in magenta) in the energy-refined X-ray (5JCB) structure from molecular docking studies. Panel A highlights the unique space (relative to the rest of the carbazole series) occupied by 28 enabling favorable hydrophobic interactions with Leu-B248. Panel B illustrates that the aromatic ring of 28 that interacts with Leu-248 overlaps with the 5 membered lactone ring of the triazole-podophyllotoxin analog (carbons in light gray). The rest of the carbazole series normally overlaps with the dioxolane component of podophyllotoxins.
Figure 13:
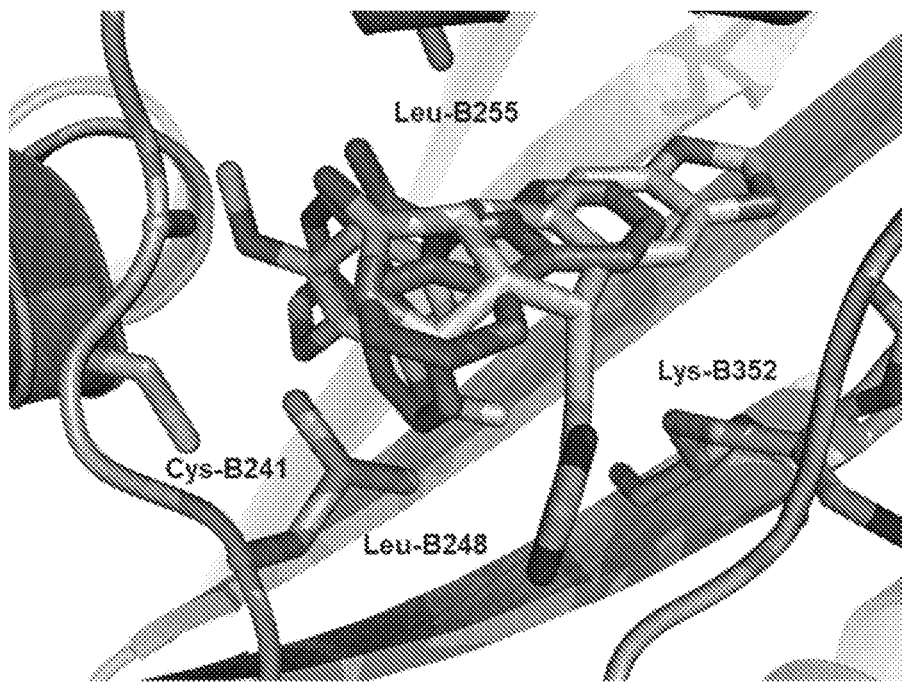
Figure 14:
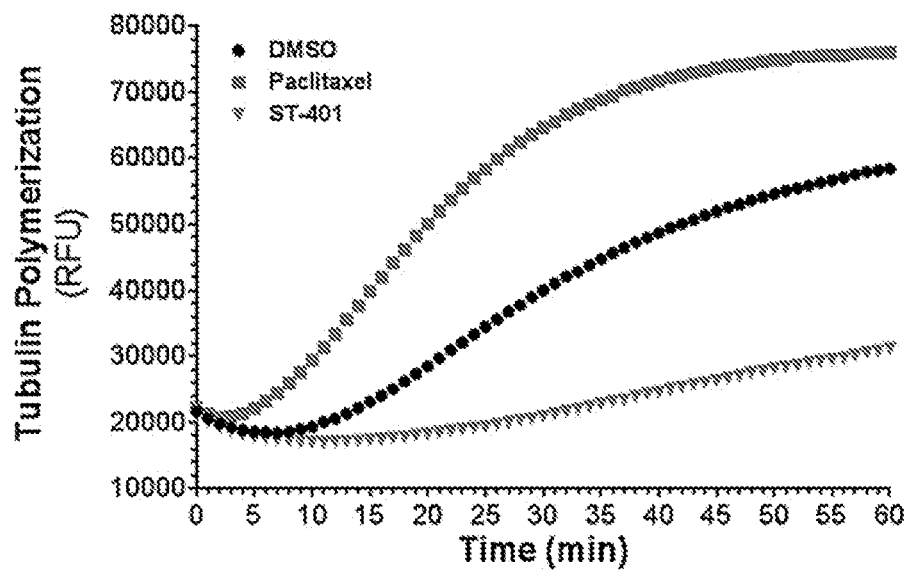
FIG. 14 illustrates that compound 19 (identified as ST-401 throughout the figures) destabilize MT. Real-time tubulin polymerization was measured by quantifying increase in fluorescent tubulin assembly in microtubule (RFU) as a function of time (minutes). Paclitaxel (10 μM) stabilizes MT and 19 (1 μM) destabilizes MT.
Figure 15:
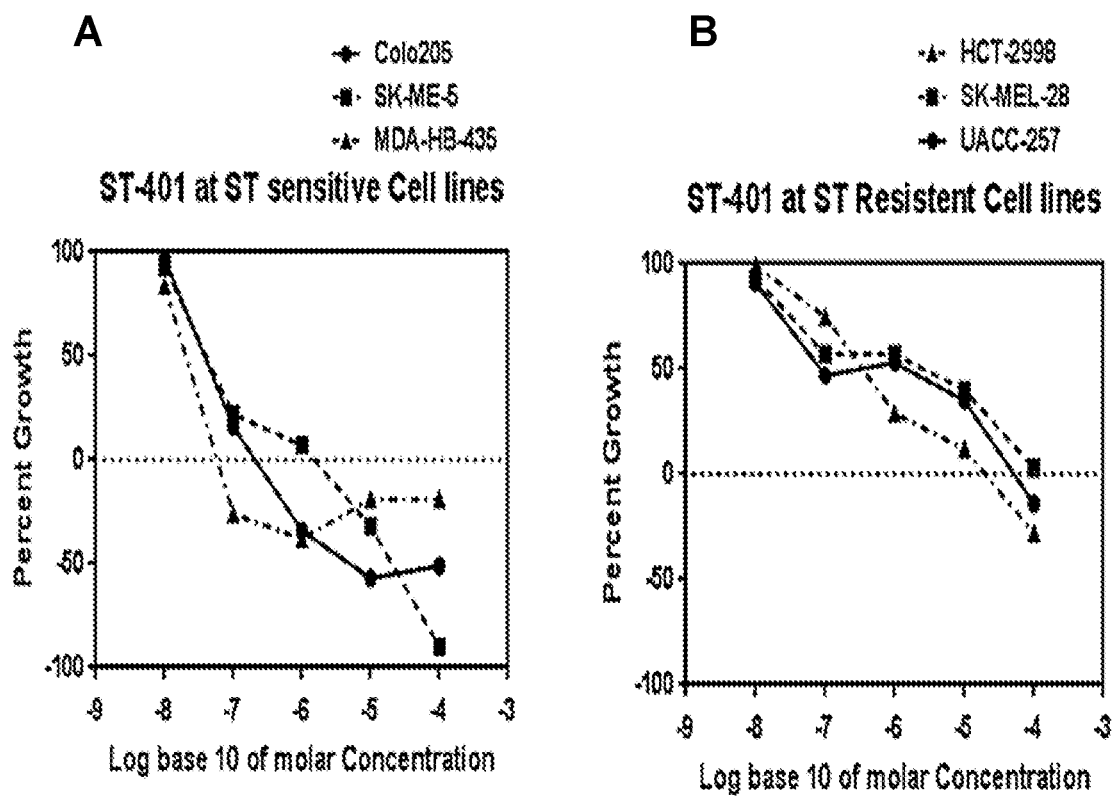
FIG. 15 illustrates anti-neoplastic activity of compound 19. Panel A: sensitive and panel B: resistant cancer cell lines from the NCI-60 cancer cell line panel. Inhibition of cell proliferative (Y values<0) and cell-killing activity (Y values<0) of increasing concentrations of 19. Differential sensitivity suggests genetic modifier(s), including mutant BRAF expressed by Colo205, SK-ME-5 and MDA-HB-435.
Figure 16:
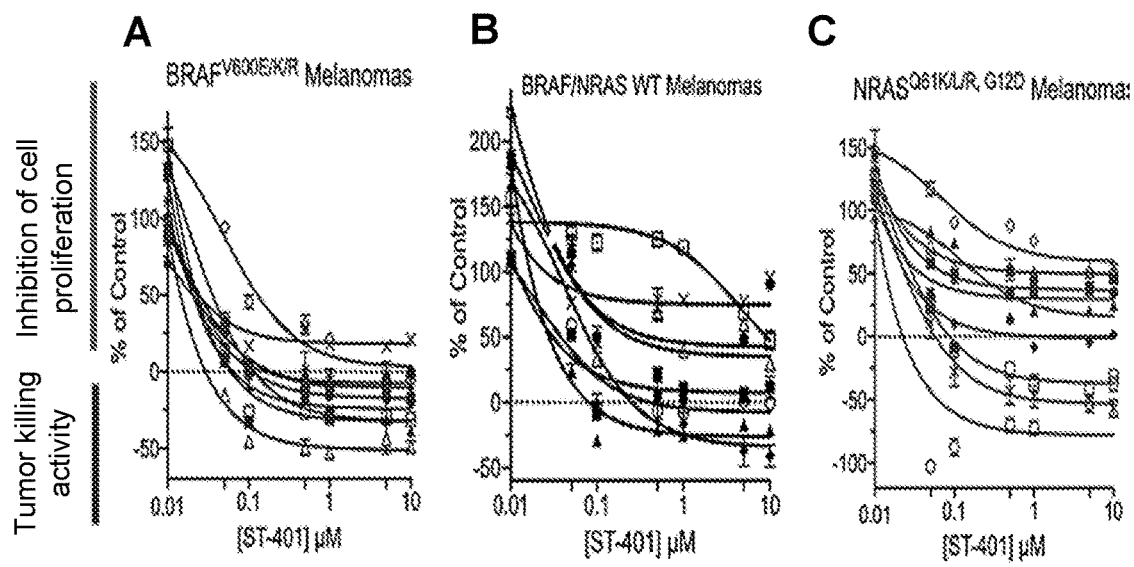
FIG. 16 illustrates preferential sensitivity of BRAF mutant melanomas cells to compound 19, where 1 μM triggers partial inhibition of patient-derived healthy melanocytes cell proliferation in culture and no killing activity. A-C: inhibition of cell proliferative (Y values<0) and cell-killing activity (Y values<0) of increasing concentrations of 19 in patient-derived melanocytes expressing (A) BRAF mutations (V600E/K/R), (B) no BRAF and NRAS mutations and (C) NRAS mutations (Q61K/L/R, G12D). Efficacy in at killing patient-derived melanoma cells in culture. This data shows preferentially-sensitivity BRAFV600K cell to compound 19.
Figure 17:
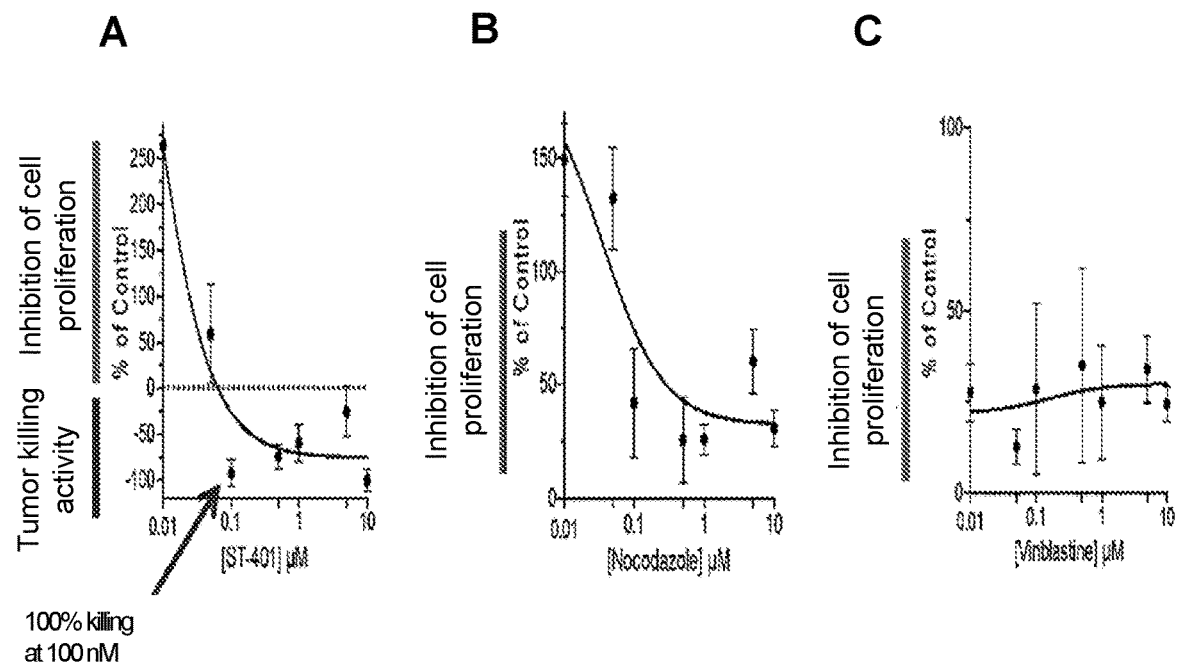
FIG. 17 illustrates that compound 19 exhibits distinct mechanism of action from other microtubule targeting agents. A-C: Inhibition of cell proliferative (Y values<0) and cell-killing activity (Y values<0) of increasing concentrations of (A) 19, (B) nocodazole and (C) vinblastine in sensitive patient-derived melanocytes expressing BRAF mutations (V600E) (YUTOGS cells). Compound 19 at 100 nM kills 100% of melanoma cells that are resistant to both nocodazole and vinblastine (two destabilizing MTAs). Results suggest different mechanistic modality.
Figure 18:
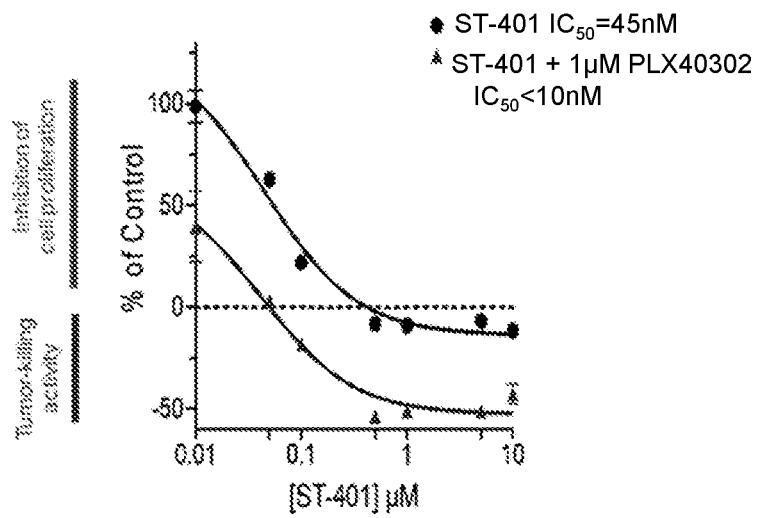
FIG. 18 illustrates that compound 19 exhibits distinct mechanism of action from BRAF inhibitors. Combination therapy with standard care mtBRAF inhibitor vemurafenib (PLX4032). Inhibition of cell proliferative (Y values<0) and cell-killing activity (Y values<0) of increasing concentrations of 19 itself (black circles) and in combination with PLX032 (1 μM) in resistant patient-derived melanocytes expressing BRAF mutations (V600E). Synergistic activity between PLX4032 and 19 occurring at low concentrations.
Figure 19:
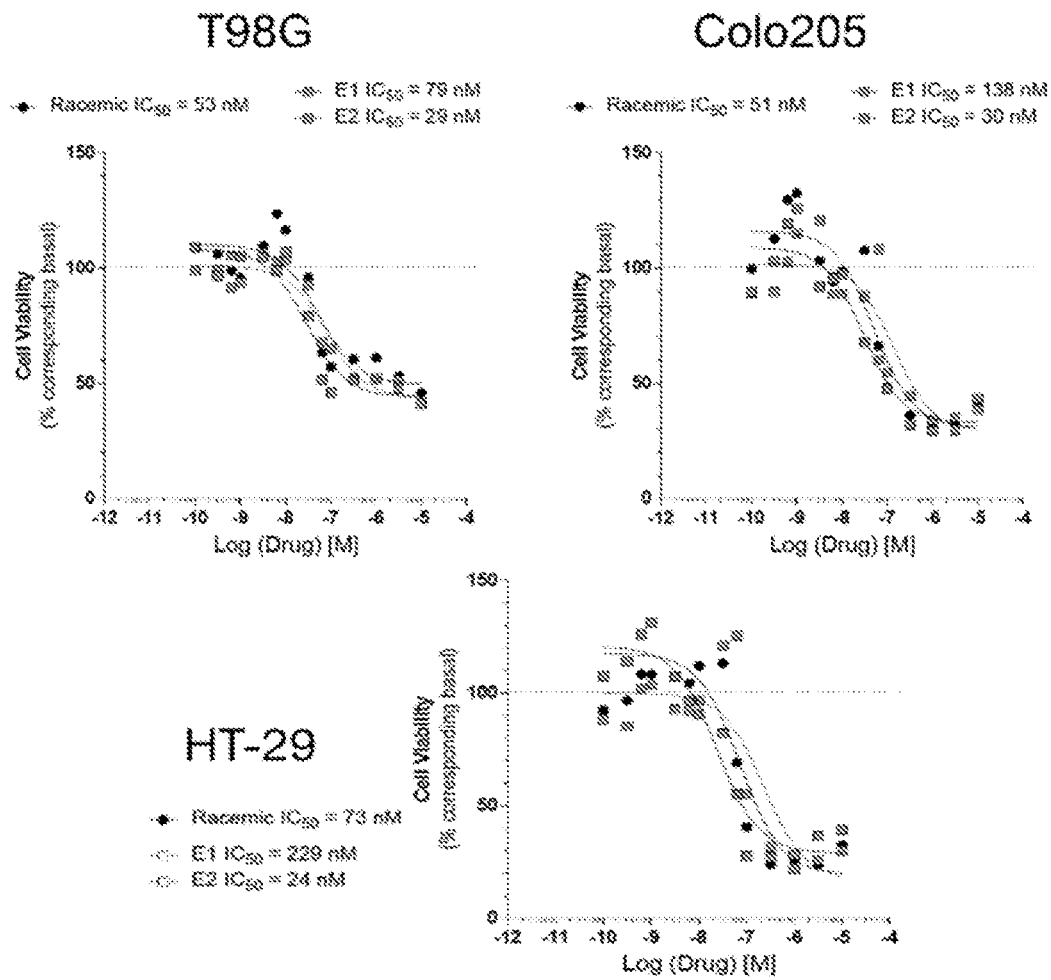
FIG. 19 illustrates that compound (–)-19 (identified as ST-403) exhibits higher cell killing potency than (+)-19 (identified as ST-402). Cell killing activity of increasing concentrations of 19 (racemic mixture, black circles) and its enantiomers, (+)-19 (E1, open light gray circles) and (–)-19 (E2, open dark grey circles) in 3 cancer cells lines (T98G, Colo205 and HT-29) was evaluated. (–)-19 exhibits 3-10 fold higher potency relative to (+)-19 and 2-3 fold higher potency relative to racemic mixture 19.
Figure 20:
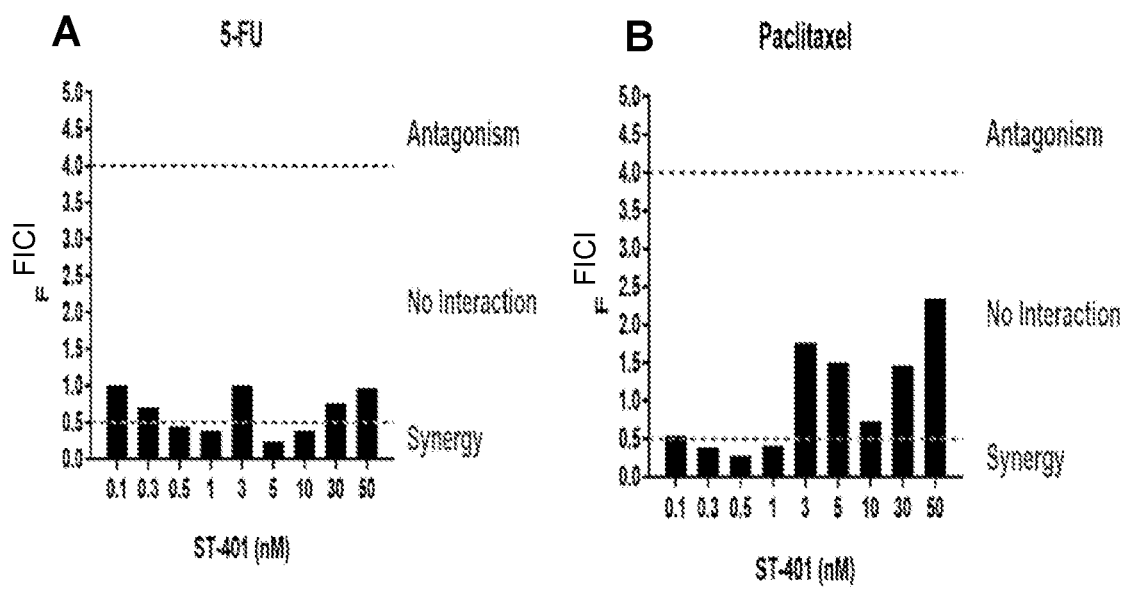
FIG. 20 illustrates activity of compound 19 in combination therapy. Increasing concentrations of compound 19 in Colo205 cells (panel A) in combination with the DNA-damaging agent 5-FU and in HT29 cells (panel B) in combination with the MT stabilizing agent paclitaxel. Compound 19 exhibits synergistic activity with 5-FU and paclitaxel when applied at low concentrations.
Figure 21:
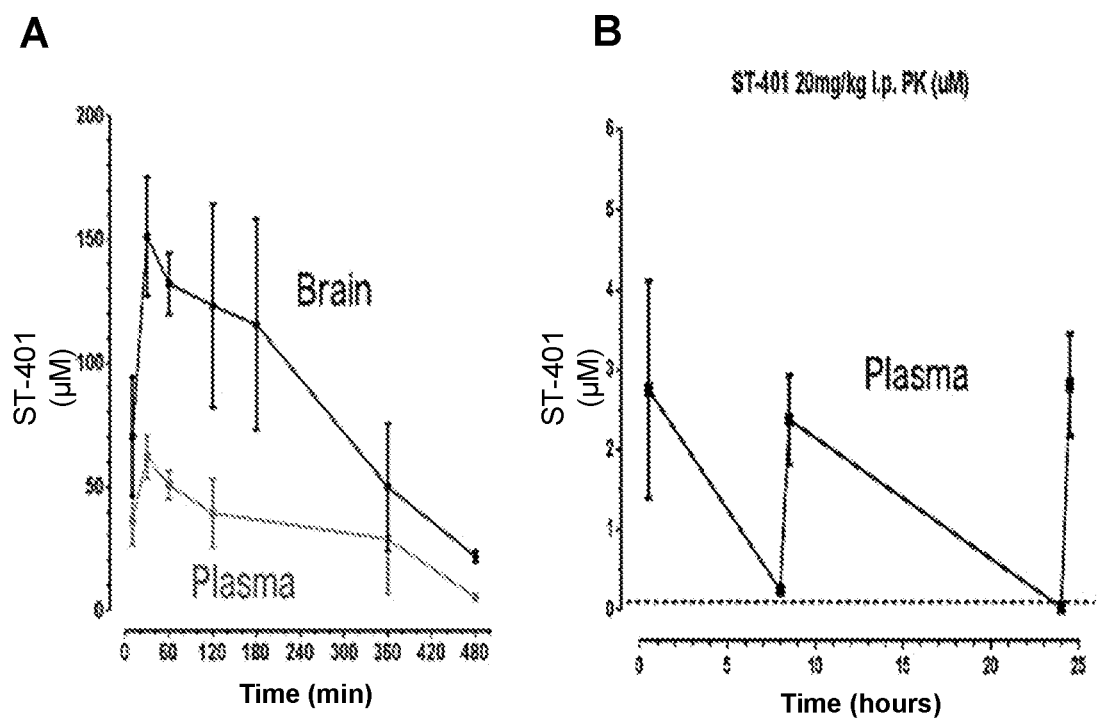
FIG. 21 illustrates pharmacokinetics of compound 19 and accumulation of 19 in brain parenchyma. A: single i.p. injection of 19 (100 mg/kg) in mice and its time-dependent accumulation in plasma and brain tissues. (n=5 mice per point). B: Repetitive i.p. injections of 19 (20 mg/kg) in mice and its time-dependent accumulation in plasma (n=5 mice per point). These results provide that 19 passes the blood brain barrier. Concentration above $EC_{90}$ (1 µM) for about 18 hours.
Figure 22:
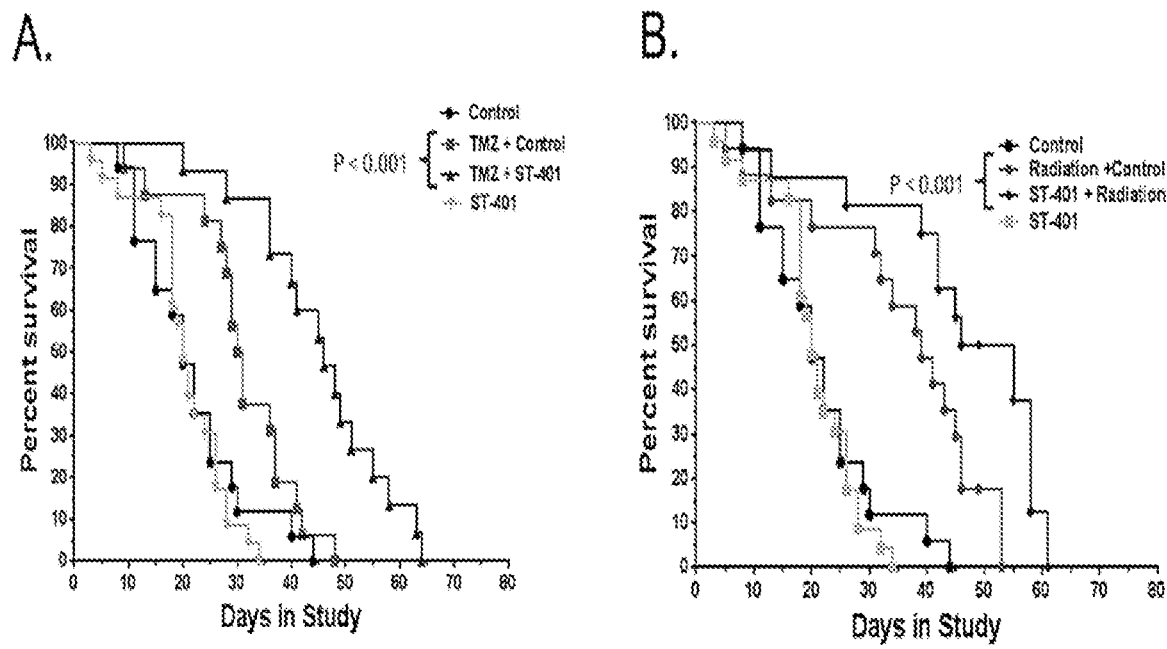
FIG. 22 illustrates tumor-killing activity and in vivo efficacy of compound 19 in GBM preclinical mouse model (generated by injecting RCAS replication competent ALV LTR with a splice acceptor-PDGFA viruses into Nestin (N)/tv-a; Ink4a-arf2/2; Ptenfl/fl mice). Tested in combination with temozolomide (Merck & Co., Inc., Whitehouse Station, N.J., identified as TMZ or Temodar®) (panel A) and radiation (panel B), compound 19 (20 mg/kg, bi-daily injections) significantly increases the therapeutic efficacy of standard care DNA-damaging agents temozolomide and radiation in PDGF-driven GBM mouse model. These results show that compound 19 crosses the blood brain barrier and significantly enhances the survival of GBM mice treated with temozolomide and radiation.
Figure 23:
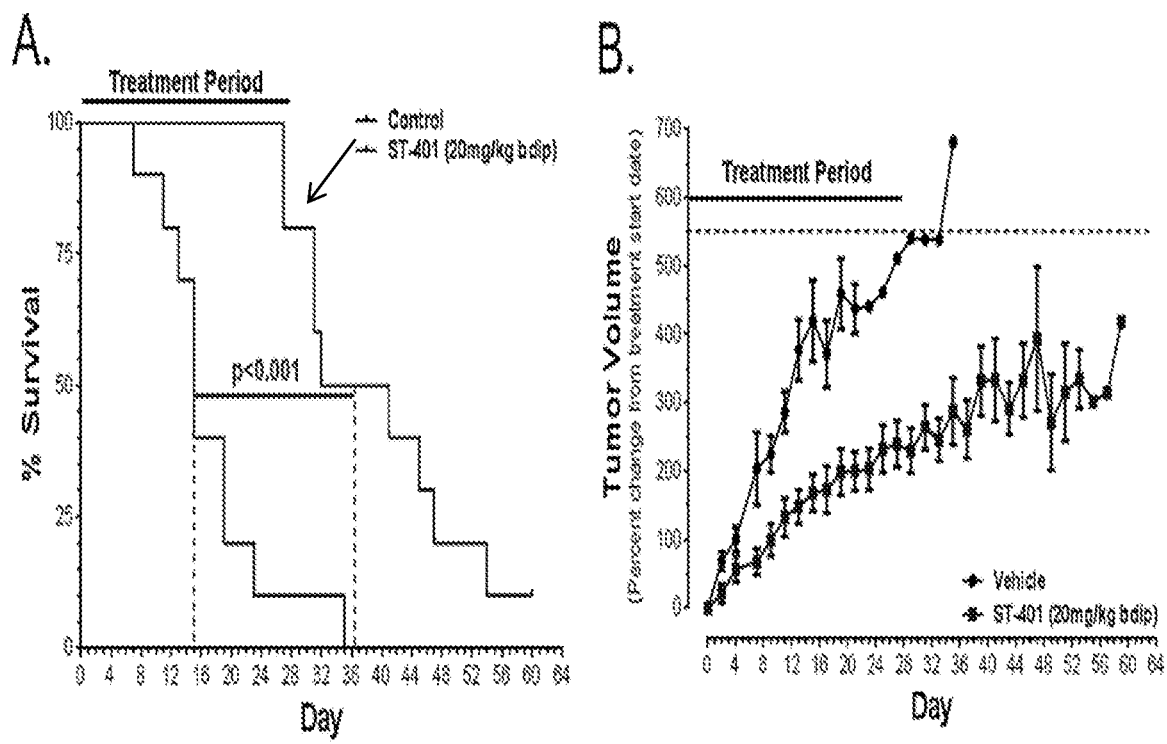
FIG. 23 illustrates tumor-killing activity and in vivo efficacy of compound 19 in BRAF-mutant preclinical mouse model. Compound 19 (20 mg/kg, bi-daily injections) significantly increases life span (panel A) and decreased tumor growth (panel B) in Colo205 xenograph mouse model. Compound 19 more than doubles mean survival and inhibits tumor growth.
Figure 24:
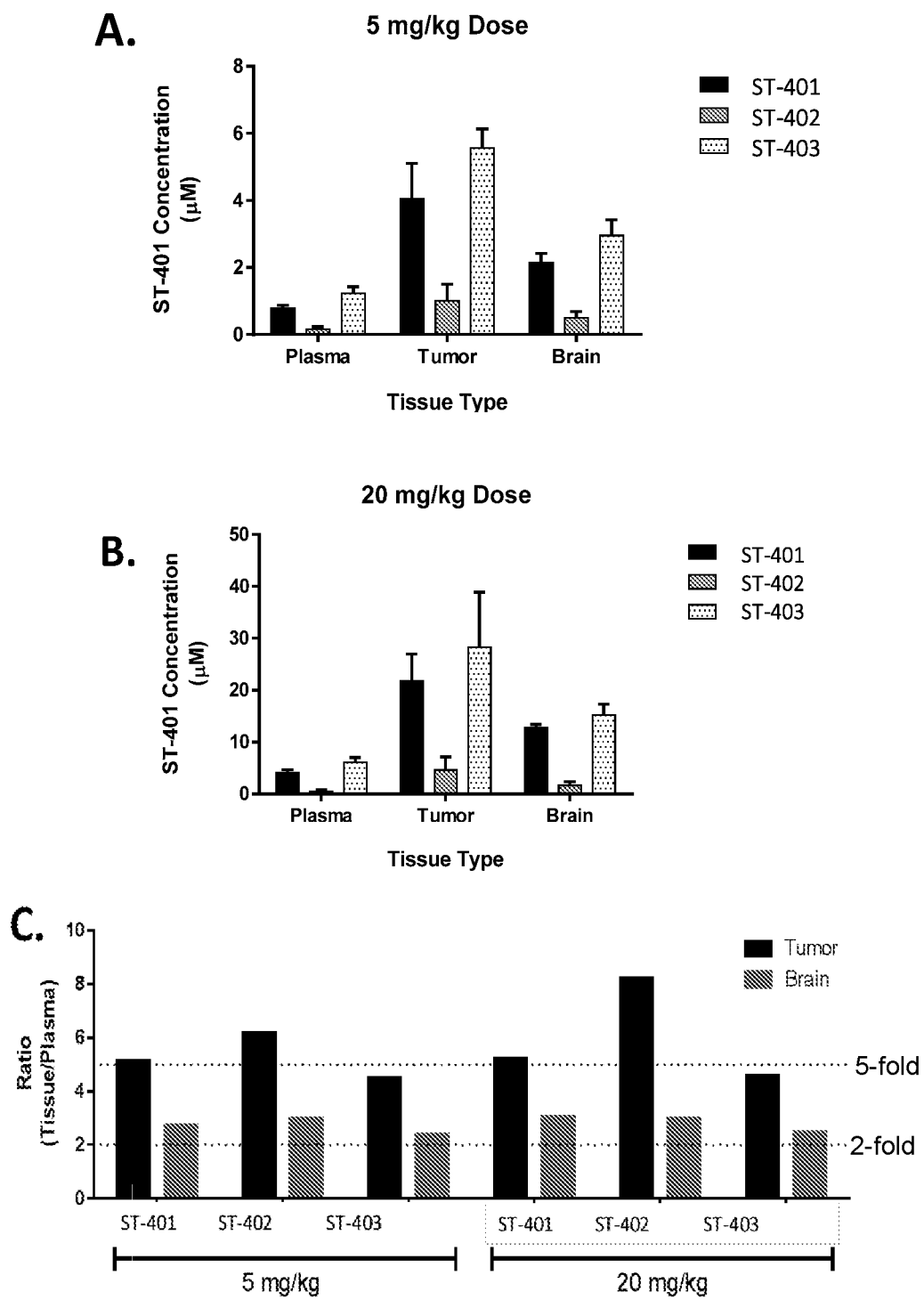
FIG. 24 illustrates biodistribution and enantiomer bias accumulation of compound 19 and its enantiomers. Amount of compound 19, (+)-19 and (−)-19 was evaluated in various tissues (plasma, flank tumor and brain) following acute injection. A: 5 mg/kg and B: 20 mg/kg. C: Ratio of amounts measured in tumor and brain shows increased accumulation of (−)-19 relative to (+)-19 (5-fold in tumor and 2-fold in brain over blood).

Finally, the molecular docking studies indicate that the structural configuration of 28 requires a unique binding mode to form a biochemically-feasible complementarity with the colchicine site that accounts for its reduced biological activity compared to 20 (FIG. 13, Panel A). Specifically, the 4-tolyl-naphthalene methanone of 28 is attached directly to the carbazole N, which causes the carbazole moiety of 28 to bind less congruently with the dioxolane component of podophyllotoxin's tetracycle. Instead, one of the carbazole's aromatic rings finds steric overlap with the hydrophobic portion of the 5-membered lactone ring of the podophyllotoxin analog. Compared to the other carbazoles, 28 forms unique, favorable hydrophobic contacts with the side chain of β-Leu-248. Interestingly, the methanone oxygen atom of 28 is still positioned close to both the other methanone oxygen atoms of the more potent compound and the lactone carbonyl oxygen atoms of podophyllotoxin (FIG. 13, Panel B). The significance of this novel binding mode is that 28 can be modified to include key features from the optimal carbazole 20, while retaining its novel interactions with the colchicine site.

Together, the structure-activity relationships of these carbazoles signify that there are key features for them to retain optimal activity in the colchicine site: 1) steric occupation of a moiety of similar size to a naphthyl, quinolinyl or trimethoxy-aryl system with preferably a hydrogen bond interacting with the β-Cys-241 sulfhydral, 2) lack of cationic ionizability for moieties that occupy the trimethoxy-aryl subsite, 3) reduction of conformational isomerism by either intramolecular steric hindrance or inherent rigidity, and 4) a strong hydrogen bond acceptor with an overlapping pose of the methanone O of 20 and the lactone carbonyl O of podophyllotoxins. Thus, the most potent 20 appears to share similar binding features with both podophyllotoxins and colchicine but provides better atom economy to achieve a comparable potency. In 20, the larger quinoline aromatic system fills the trimethoxy-aryl subsite in a sterically more compact manner than colchicine and podophyllotoxin. Moreover, the quinoline nitrogen atom serves as a strong hydrogen bond acceptor capable of forming diverse hydrogen bonding interactions either directly with the side chain of β-Cys-241 (FIG. 9) or via water bridges (models not shown). It has been shown that the short N-ethyl substituent on the carbazole part of 20 is involved in key hydrophobic interactions with the side chain of β-Lys-352 (FIG. 11, Panel A). The molecular docking studies provide a unified structure-based explanation for both positive and negative substitutions according to the SAR of the carbazole analogs.

Biological Example 7: Activity on Cannabinoid CB$_1$ and CB$_2$ Receptors

Several compound of the invention were evaluated for activity on CB$_1$ and CB$_2$ receptors, hCB$_1$- and hCB$_2$-transfected HEK293 cells were incubated with increasing concentrations of the full agonist CP55940 (positive control) and 23, 8, 27 and 20 and functional receptor activity was assessed by measuring β-arrestin recruitment as previously described. EC$_{50}$ and efficacy values were calculated using Prism® software, and the results are presented in Table 4.
Table 4. Activity on cannabinoid CB$_1$ and CB$_2$ receptors

TABLE 4

Activity on cannabinoid CB$_1$ and CB$_2$ receptors

| Compounds | Agonist efficacy (% activation) | | Antagonist efficacy (% activation) | |
|---|---|---|---|---|
| | CB$_1$ | CB$_2$ | CB$_1$ | CB$_2$ |
| positive control | 1940 | 4275 | 97 (126 nM) | 92 (1100 nM) |
| 23 | −2 | 2 | 16 (183 nM) | 20 (67 nM) |
| 8 | 5 | 8 | 51 (2260 nM) | 52 (1431 nM) |
| 27 | 7 | 8 | 47 (934 nM) | 44 (323 nM) |
| 20 | 1 | 12 | 93 (2100 nM) | 94 (2225 nM) |

Biological Example 8: Activity of Compound 19 and (+)-19 and (−)-19 Enantiomers As provided in FIGS. 14-24, compound 19 (identified as 19), including its enantiomers, was found as having the activities of destabilizing MT, anti-neoplastic activity, preferential sensitivity of BRAF mutant melanoma cells, cell killing activity of melanocytes expressing BRAF mutants, and synergy with PLX4032, 5-FU, and paclitaxel.

In addition, compound 19 has much higher activity in T98G cells in culture compared to the carbonyl linker derivative compound 20. For example, as provided in FIG. 19, compound 19 exhibits an EC$_{50}$ of 53 nM, whereas compound 20 has EC$_{50}$ of 184 nM (Table 1). In addition, compound 20 showed no activity in HT-29 (EC$_{50}$>100 μM) and low activity in Colo205 (EC$_{50}$>948 nM) (FIG. 5). In contrast, compound 19 exhibits an EC$_{50}$ of 73 and 51 nM in HT-29 and Colo205, respectively.

The inventors also identified increased cell killing by one enantiomer of compound 19 (i.e., (−)-19) when compared to the other enantiomer (i.e., (+)-19). For example, the activity of compound 19, (+)-19 and (−)-19 at tubulin polymerization was evaluated. IC$_{50}$ values in μM measure with increasing concentration of vinblastine (positive control: triggers MT disassembly), paclitaxel (positive control: stabilizes MT), racemic mixture compound 19, (+)-19 enantiomer (ST-402) and (−)-19 enantiomer (ST-403). Dose-response curves that generated results in Table 5. Tubulin assembly was measured using fluoresent-rescent tubulin in 100 μl according to manufacturer's protocol (Cytoskeleton Inc.).
Table 5. Activity at tubulin polymerization

TABLE 5

Activity at tubulin polymerization

| Compound | IC$_{50}$ (μM) |
|---|---|
| Vinblastine | 0.41 |
| Paclitaxel | N/A |

TABLE 5-continued

Activity at tubulin polymerization

| Compound | IC$_{50}$ (μM) |
|---|---|
| compound 19 | 0.59 |
| (+)-19 enantiomer | 0.64 |
| (−)-19 enantiomer | 0.61 |

Finally, the safety profile of compound 19 was evaluated. Specifically, the experimental toxicity study of i.p. injection of compound 19 compared to compound 20 was evaluated in rodents and off-targets. Maximal tolerated dose (MTD) following one injection (acute) or repeated (28 days) injections is provided in Table 6. No-observed-adverse-effect-level (NOAEL) at 20 mg/kg bdip of compound 19 was found when analyzing the histopathology of 22 organs after repeated (28 days) mouse administration. Off target profile of compound 19 tested at 1 μM exhibited a promising safety profile in preclinical rodent models. Specifically, compound 19 did not affect hERG, did not intercalate DNA, and interacted with less than 5% off-targets.
Table 6. Maximal tolerated dose

TABLE 6

Maximal tolerated dose

| Compound | Acute mouse (mg/kg) | 28 Days Mouse (mg/kg bdip) | Acute Rat (mg/kg) |
|---|---|---|---|
| 20 | 160 | 50 | 200 |
| 19 | 150 | 20 | 50 |

Biological Example 9: Additional Activity of Compound 19

Figure 25:
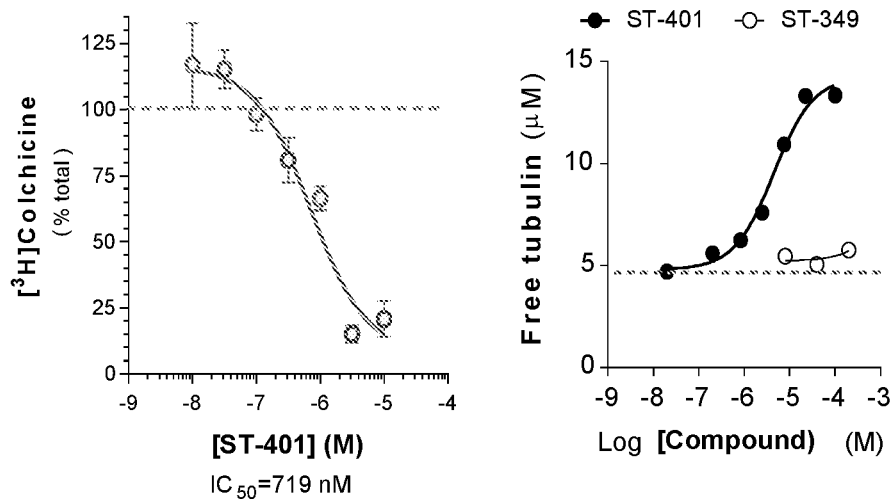
FIG. 25 illustrates compound 19 binding to the colchicine site of tubule and triggering of microtubule (MT) disassembly in vitro. A. Increasing concentrations of 19 compete for [$^3$H]Colchicine binding to purified tubulin in vitro using a glass fiber filtering assay and luminescence detection of radioactivity. Analysis of dose-response results in an $IC_{50}$=719 nM. Results are mean±SEM from n=4-5 independent experiments performed in triplicates. B. Increasing concentration of 19 triggers microtubule disassembly in vitro as measured using a free tubulin pelleting assay detected by gel separation and semi-quantitative image analysis. The inactive analogue, 23, does not affect MT assembly. Results are from 3 independent experiments performed in duplicate.
Figure 26:
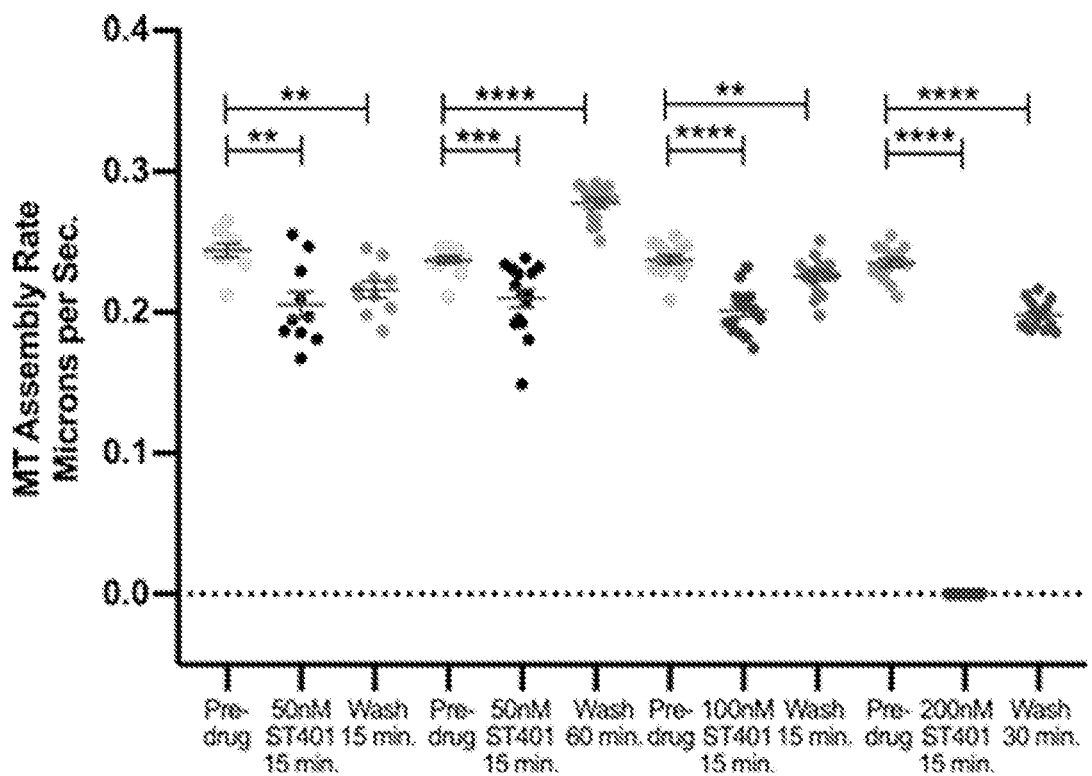
FIG. 26 illustrates MT assembly rate in Hct116 cells in culture were measured by following GFP-EB3 fluorescent signal by real-time fluorescence microscopy (basal pre-drug represented with gray dots). Low concentrations of 19 (50 and 100 nM, black and dark blue dots, respectively) significantly reduce MT assembly and this response is reversible when measured after 15 min wash. Higher concentrations of 19 (200 nM, purple dots) fully stops MT assembly and this response is reversible when measure after 30 min wash. Each dot represents MT assembly rate in one cell. Lower *, P<0.001 and , P<0.01 compared with pre-drug; one-way ANOVA with the Tukey post-hoc test. Data are the mean±SEM.
Figure 27:
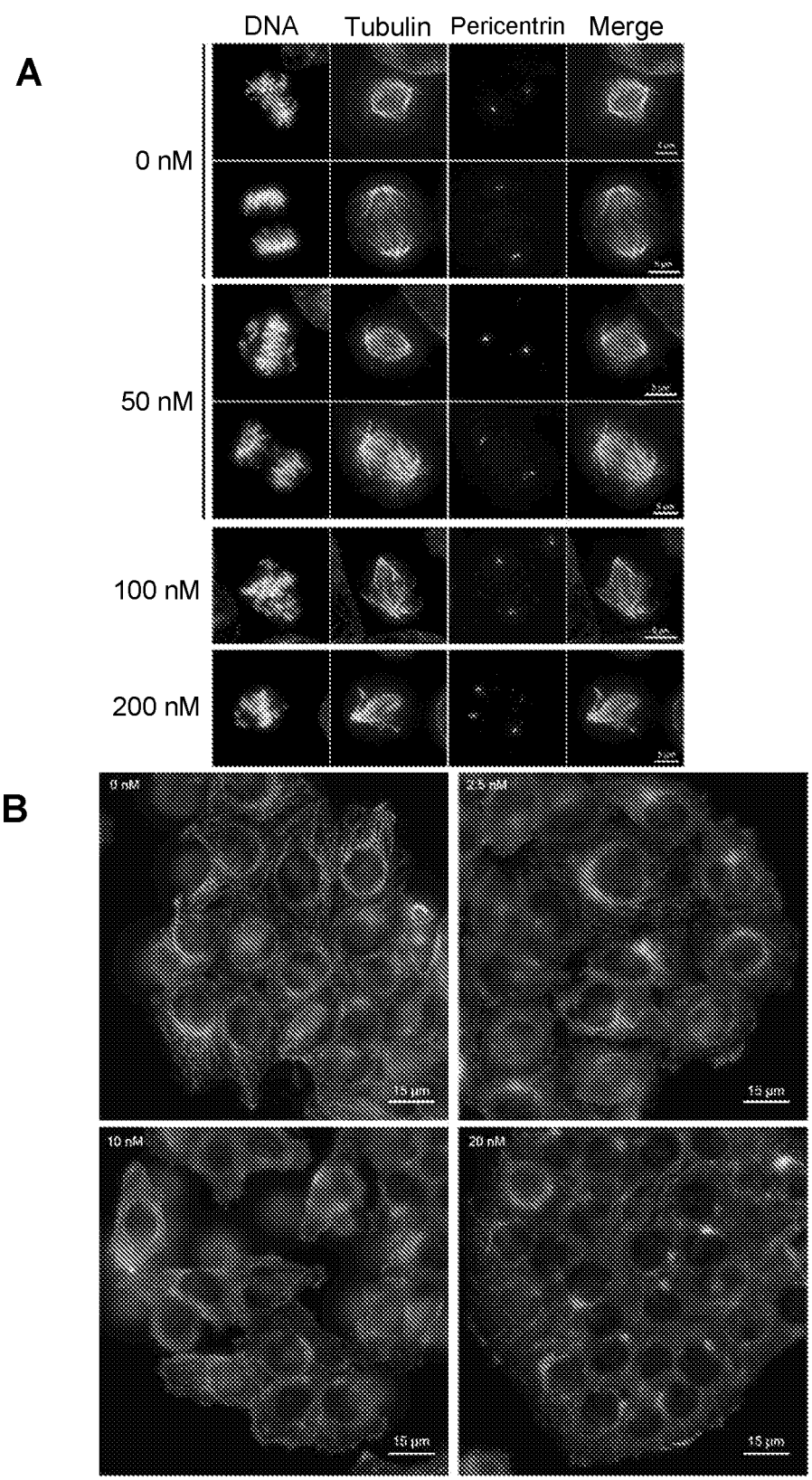
FIG. 27 illustrates the mitosis arrest and disruption of microtubule network in Hct166 cells in culture by the compound of disclosure. A: Hct116 cells were treated with either vehicle control (0 nM; DMSO 1:1000) or 19 (50, 100 or 200 nM) for 4 hours, fixed-stained and imaged for DNA (DAPI staining), tubulin (anti-tubulin α) and centrosomes (anti-pericentin). Compound 19 increases the presence of disrupted MT arising from the centrosome during prometaphase and of misaligned chromosomes in a concentration-dependent manner. Representative images (Scale bar=5 µm). B: Hct116 cells were treated with either vehicle control (0 nM; DMSO 1:1000) or 19 (2.5, 10 or 20 nM) for 24 hours, fixed-stained and imaged for tubulin (anti-tubulin a). Compound 19 disrupts MT network in a concentration-dependent manner. Representative images (Scale bar=15 µm) imaged with an InCell 2500 system.

As provided in FIG. 25, compound 19 binds to the colchicine site of tubule and triggers microtubule (MT) disassembly in vitro. Compound 19 also reduces MT assembly rate in Hct116 cells, this response is partial at low concentration and complete at higher concentration, and in both case reversible (FIG. 26). Further, as illustrated in FIG. 27, compound 19 promotes prometaphase mitosis arrest and disrupts microtubule network in Hct166 cells in culture.

Figure 28:
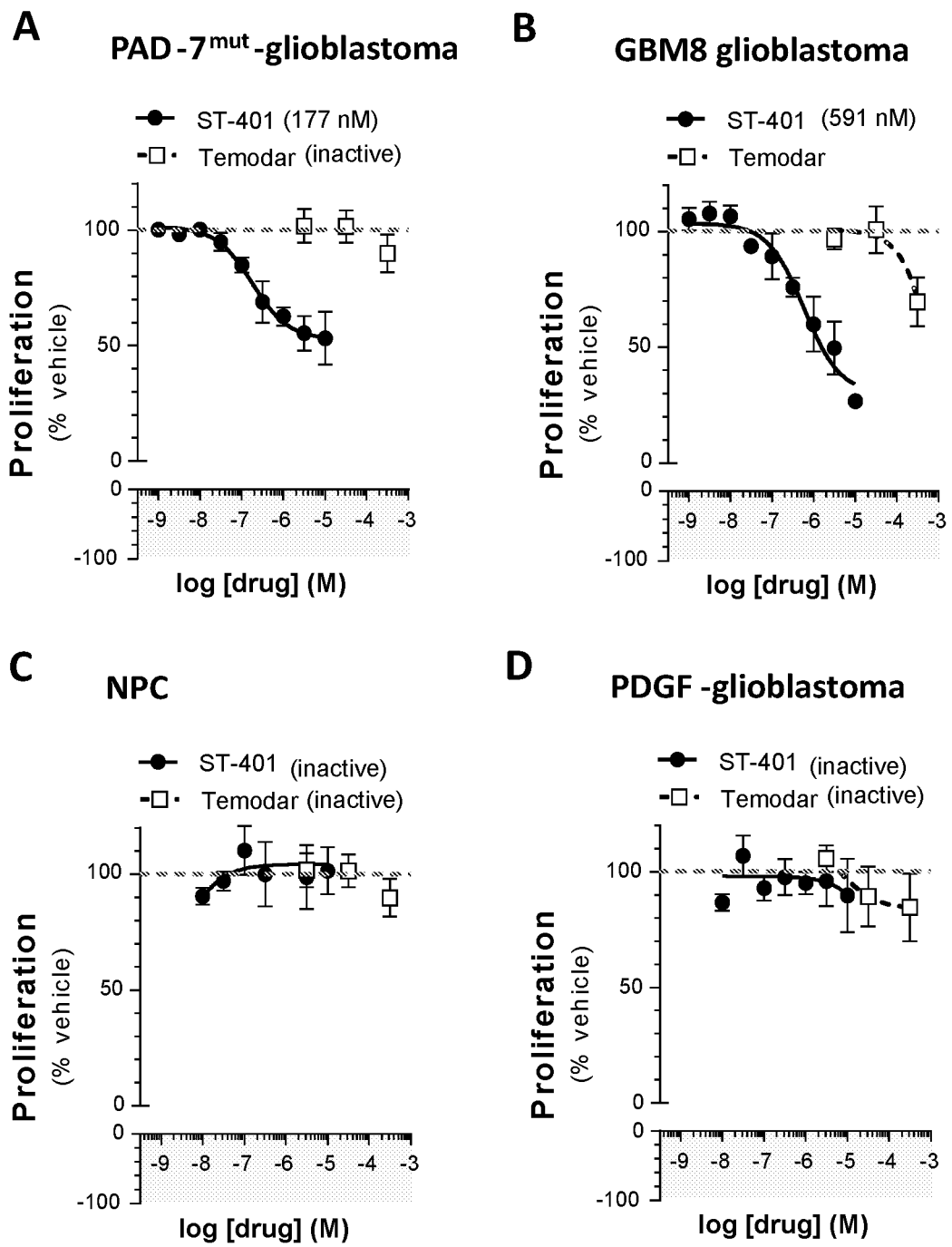
FIG. 28 illustrates the effect of the compound of the disclosure on the cell proliferation of glioblastomas, neural stem cells and PDGF-amplified signaling glioblastomas. Panels A-B: Cell proliferation of human PAD-7$^{mut}$ glioblastoma cells in culture (neural stem cells CB660 harboring 7 driver mutations involved in glioblastoma pathogenesis: $TP53^{DD}$, $TERT^{mut}$, $CCND1^{mut}$; $CDK4R^{24C}$; p16 binding deficient; $EGFR^{vIII}$ and myristolated-AKT), and has non-methylated MGMT promoter (temozolomide insensitive) and human GBM8 glioblastoma cells in culture (patient-derived human glioblastoma cells closest to proneural phenotype) and has methylated MGMT promoter (temozolomide sensitive). Panels C-D: Cell proliferation of mouse NPC (neural progenitor cells generated by the mechanical dissociation of the newborn pup forebrains of N/tv-a; Ink4a-arf2/2; Ptenfl/fl mice) and mouse PDGF-glioblastoma cells (generated by injecting RCAS replication competent ALV LTR with a splice acceptor-PDGFA viruses into Nestin (N)/tv-a; Ink4a-arf2/2; Ptenfl/fl mice and harvesting cells by mechanical dissociation of the tumors that had developed in the mouse brain).

Compound 19 inhibits cell proliferation of glioblastomas and does not affect cell proliferation of neural stem cells and PDGF-amplified signaling glioblastomas as illustrated in FIG. 28. FIGS. 28 A-B provide cell proliferation of human PAD-7$^{mut}$ glioblastoma cells in culture (neural stem cells CB660 harboring 7 driver mutations involved in glioblastoma pathogenesis: TP53$^{DD}$, TERT$^{mut}$, CCND1$^{mut}$; CDK4R$^{24C}$; p16 binding deficient; EGFR$^{vIII}$ and myristolated-AKT), and has non-methylated MGMT promoter (temozolomide insensitive) and human GBM8 glioblastoma cells in culture (patient-derived human glioblastoma cells closest to proneural phenotype) and has methylated MGMT promoter (temozolomide sensitive). Cell proliferation was measured by quantifying BrdU incorporation in cells at seeding (dark gray zone) and following 3 days (light gray zone) of treatment with compound 19 and temozolomide. Compound 19 inhibits the cell proliferation of both PAD-7$^{mut}$ and GBM8 cells in a concentration-dependent manner (EC$_{50}$=177 nM and 591 nM, respectively). As expected, cell proliferation of PAD-7$^{mut}$ cells is insensitive to temozolomide and of GBM8 cells only sensitive at high concentration of temozolomide (300 μM). Data are the mean±SEM of 3-5 independent experiments performed in triplicates. Panels C-D provide cell proliferation of mouse NPC (neural progenitor cells generated by the mechanical dissociation of the newborn pup forebrains of N/tv-a; Ink4a-arf2/2; Ptenfl/fl mice) and mouse PDGF-glioblastoma cells (generated by injecting RCAS replication competent ALV LTR with a splice acceptor-PDGFA viruses into Nestin (N)/tv-a; Ink4a-arf2/2; Ptenfl/fl mice and harvesting cells by mechanical dissociation of the tumors that had developed in the mouse brain). Cells were initially maintained as floating neurospheres cultures and starting at passages 5 and 3 (PDGF-glioblastomas cells and NPCs, respectively) were cultured as adherent monolayers on laminin-coated dishes. Neither compound 19 nor temozolomide affect the cell proliferation of both NPC and PDGF-glioblastoma cells. Cell proliferation was measured by quantifying BrdU incorporation in cells at seeding (dark gray zone) and following 3 days (light gray zone) of treatment with compound 19 and temozolomide. Data are the mean±SEM of 3-5 independent experiments performed in triplicates.

Next, the inventors found that compound 19 kills patient-derived human glioblastoma cells in culture belonging to all major subtypes: proneuronal, classical and mesenchymal) (Table 7). Compound 19 also kills patient-derived human melanomas in culture with higher efficacy than standard care BRAF inhibitor Veramufanib®. Patient-derived human glioblastoma cells in culture of all major subtypes were treated with increasing concentration of compound 19. Cell viability was measured by quantifying changes in cell-permeable WST-1 color 3 days after treatment. Compound 19 kills all tested PD-glioblastomas with an $EC_{50}$ of 17-102 nM. Data are the mean±SEM of 3-5 independent experiments performed in triplicates.

Table 7. Maximal tolerated dose

TABLE 7

| Maximal tolerated dose | | |
|---|---|---|
| Cell ID | Subtype | $EC_{50}$ (nM) |
| SN227 | proneuronal | 90 |
| SN276 | mesenchymal | 17 |
| SN260 | mesenchymal | 79 |
| SN243 | classical | 34 |
| SN262 | classical | 47 |
| SN264 | classical | 102 |

Figure 29:
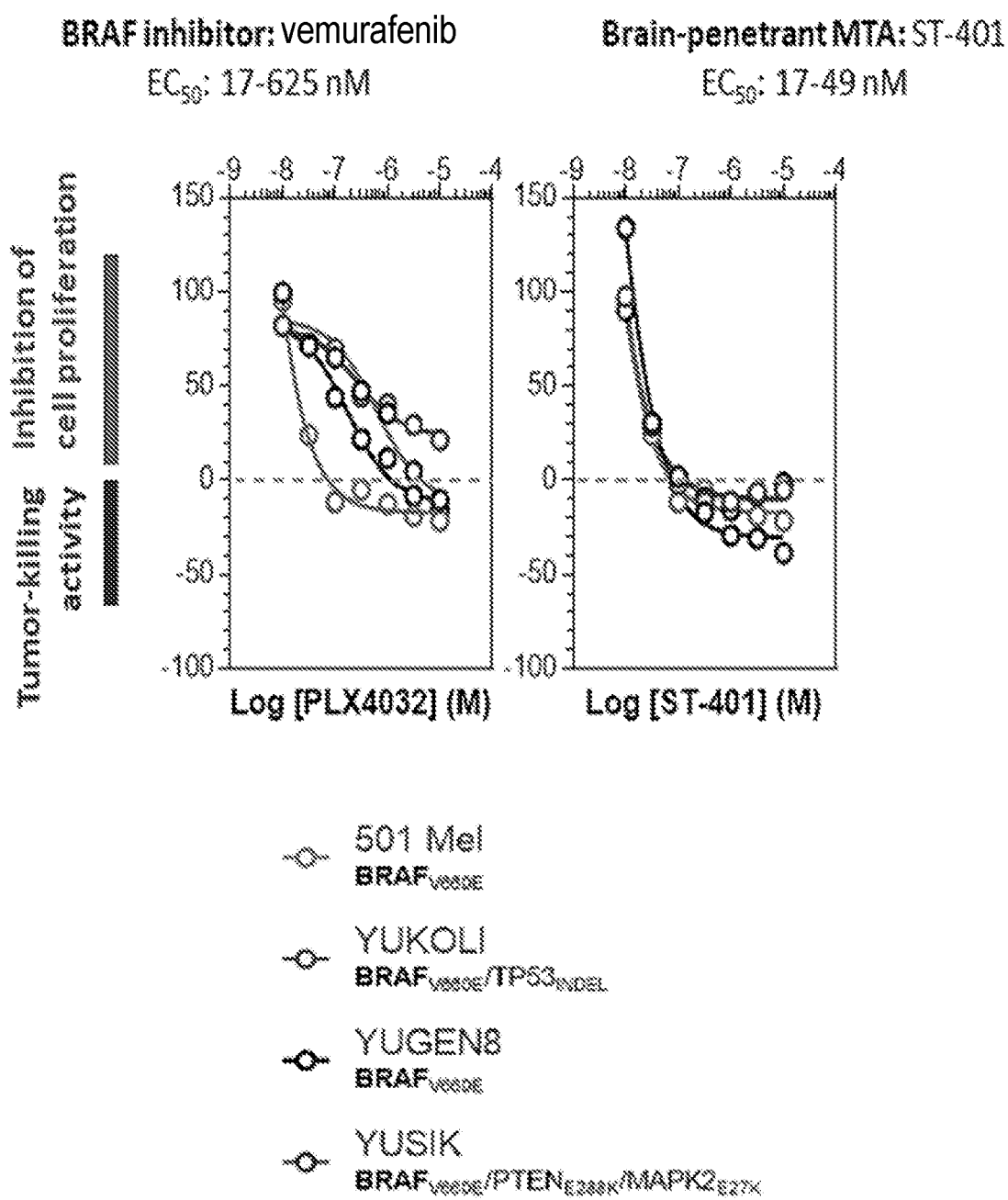
FIG. 29 illustrates the activity of the compound of the disclosure in patient-derived human melanomas compared to standard care BRAF inhibitor vemurafenib.

Finally, as provided in FIG. 29, compound 19 kills patient-derived human melanomas in culture with higher efficacy than standard care BRAF inhibitor vemurafenib. Patient-derived human melanoma cells in culture harboring BRAF mutations present in approximately 50% of this patents were treated with increasing concentration of compound 19 and standard care $BRAF^{V600E}$ inhibitor vemurafenib. Cell viability was measured by quantifying changes in cell-permeable Alamar blue color both at seeding (gray zone) and 3 days after treatment (white zone). All tested PD-melanomas were killed by compound 19 and vemurafenib. Data are the mean±SEM of 3-5 independent experiments performed in triplicates.

General Procedures

Chemical procedures and characterization. Moisture sensitive reactions were performed in an inert, dry atmosphere of argon in flame-dried glassware. Air sensitive liquids were transferred via syringe or cannula through rubber septa. Reagent grade solvents were used for extraction and flash chromatography. Tetrahydrofuran was distilled from Na/benzophenone under argon. All commercially obtained reagents and solvents were used directly without further purification. The progress of reactions was checked by analytical thin-layer chromatography (Silica G TLC plates with UV 254). Flash column chromatography was performed using prepacked Biotage SNAP/ZIP cartridges on a Biotage Isolera One instrument. The solvent compositions reported for all chromatographic separations are on a volume/volume (v/v) basis. $^1H$ NMR spectra were recorded at 400 MHz and are reported in parts per million (ppm) on the δ scale relative to tetramethylsilane as an internal standard. $^{13}C$ NMR spectra were recorded at 100 MHz and are reported in parts per million (ppm) on the δ scale relative to $CDCl_3$. Melting points were determined on a Stuart melting point apparatus from Bibby Scientific Limited and are uncorrected. LC/MS and HRMS analyses were obtained on a Waters ACQUITY UPLC-series liquid chromatography system equipped with a diode array detector and coupled to a LCT PREMIER XE™ time of flight (TOF) mass spectrometer with electrospray ionization (ESI). The liquid chromatography conditions were as follows: a Phenomenex column (NX, 3 μm, C18, 110A, 50.0×4.6 mm) was used, and bound compounds were eluted with the following gradient over 15 min at a rate of 0.4 mL/min (water (0.1% formic acid)/acetonitrile): (90/10 to 2/98, 0-6.6 min), (2/98 isocratic, 6.6-13 min), (2/98 to 90/10, 13-15 min). Compound purity was assigned based on 254 nM detection data assessed by comparing relative peak areas of the signals. All final compounds were more than 95% pure.

Cell culture. Cells were cultured in DMEM supplemented with 10% FBS, 100 U/mL penicillin, and 100 μg/mL streptomycin at 37° C. in a 5% $CO_2$ humidified atmosphere. T98G and HepG2 cells (ATCC, Manassas, Va.) were authenticated by ATCC when purchased using human short tandem repeat analysis and maintained in culture for less than 6 months. Tumors were obtained from surgeries performed at the Swedish Medical Center (Seattle, Wash.) according to Institutional Review Board guidelines. Patient samples used in this study were diagnosed as WHO grade IV glioblastoma multiforme. Patient-derived GBM cells were established from the freshly resected tumor tissues and maintained in NeuroCult® NSA medium (Stem Cell Technologies) with B-27 serum-free supplement, 20 ng/mL epidermal growth factor and 20 ng/mL fibroblast growth factor 2 as previously described.

Cell viability. WST-1 (Roche, Pleasanton, Calif.) was used to evaluate cell viability as previously described 72 hours following drug treatment according to the manufacturer's protocol. Maximal % killing was calculated as the % reduction in cell viability measured at all drug concentration. $EC_{50}$ values were calculated and reported only when a curve was reliably extrapolated by Prism software. The solvent for all modified carbazoles was DMSO (0.1% final). This solvent (negative reference, vehicle control) had no effect on cell viability.

[$^3H$]Colchicine binding to purified tubulin and tubulin assembly. [$^3H$]Colchicine binding to purified tubulin and tubulin assembly (as assessed by turbidity development in purified bovine tubulin solutions) were both measured as previously described.

MT-tubulin partitioning. Bovine brain tubulin was purified, polymerized into MTs and sheared as previously described. Sheared MTs and drugs were incubated at 37° C. for 15 min and centrifuged for 10 min at 42,000 rpm at 37° C. prior to separation into supernatants containing free tubulin and pellets containing polymerized MTs as previously described. Supernatants and pellets were run on a 4-12% polyacrylamide gel and stained with Coomassie G-250 for quantification. Peak intensities were quantified using ImageJ.

Numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound of formula (I):

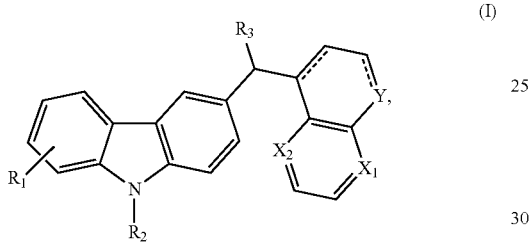

(I)

or a pharmaceutically acceptable salt or prodrug thereof, or a stereoisomer thereof, wherein
each ═══ independently represents a single or double bond, provided that the bond satisfies the valence requirement of the C and/or N atoms;
$X_1$ and $X_2$ are independently selected from CH and N;
Y is $C(R_4)_2$ or $NR_4$ when ═══ represents a single bond, or Y is $CR_4$ or N when ═══ represents a double bond;
wherein each $R_4$ is independently hydrogen or $C_1$-$C_6$ alkyl optionally substituted with one or more $R_5$;
$R_1$ is selected from the group consisting of hydrogen, halogen, $C_1$-$C_6$ alkyl optionally substituted with one or more $R_6$, $C_2$-$C_6$ alkenyl optionally substituted with one or more $R_6$, $C_2$-$C_6$ alkynyl optionally substituted with one or more $R_6$, —O($C_1$-$C_6$ alkyl), and —CO($C_1$-$C_6$ alkyl) optionally substituted with one or more $R_6$;
$R_2$ is selected from the group consisting of $C_1$-$C_6$ alkyl optionally substituted with one or more $R_7$, $C_2$-$C_6$ alkenyl optionally substituted with one or more $R_7$, $C_2$-$C_6$ alkynyl optionally substituted with one or more $R_7$, —CO($C_1$-$C_6$ alkyl) optionally substituted with one or more $R_7$, aryl($C_0$-$C_6$ alkyl) optionally substituted with one or more $R_8$, heteroaryl($C_0$-$C_6$ alkyl) optionally substituted with one or more $R_8$, heterocyclyl($C_0$-$C_6$ alkyl) optionally substituted with one or more $R_7$, and cycloalkyl($C_0$-$C_6$ alkyl) optionally substituted with one or more $R_7$; and
$R_3$ is —OH, —O($C_1$-$C_6$ alkyl), —NH$_2$, —NH($C_1$-$C_6$ alkyl), —N($C_1$-$C_6$ alkyl)$_2$, —SH, or —S($C_1$-$C_6$ alkyl), wherein:
each $R_5$ is independently selected from the group consisting of halogen, —NO$_2$, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —CONH$_2$, —CONH($C_1$-$C_6$ alkyl), —CON($C_1$-$C_6$ alkyl)$_2$, —CO$_2$H, and —CO$_2$($C_1$-$C_6$ alkyl);
each $R_6$ is independently selected from the group consisting of halogen, —NO$_2$, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —CONH$_2$, —CONH($C_1$-$C_6$ alkyl), —CON($C_1$-$C_6$ alkyl)$_2$, —CO$_2$H, and —CO$_2$($C_1$-$C_6$ alkyl);
each $R_7$ is independently selected from the group consisting of halogen, —NO$_2$, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —CONH$_2$, —CONH($C_1$-$C_6$ alkyl), —CON($C_1$-$C_6$ alkyl)$_2$, —CO$_2$H, and —CO$_2$($C_1$-$C_6$ alkyl), or two $R_7$ groups when attached to the same carbon atom form ═O; and
each $R_8$ is independently selected from the group consisting of halogen, —NO$_2$, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

2. The compound of claim 1, comprising compounds of formula (I-2):

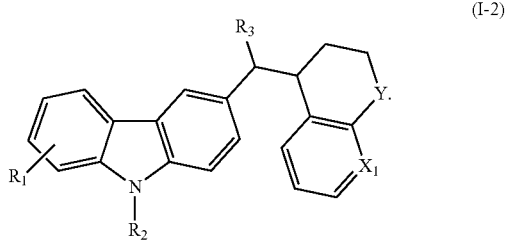

(I-2)

3. The compound of claim 1, wherein each $R_4$ is independently hydrogen or $C_1$-$C_6$ alkyl.

4. The compound of claim 1, comprising compounds of formula (I-4):

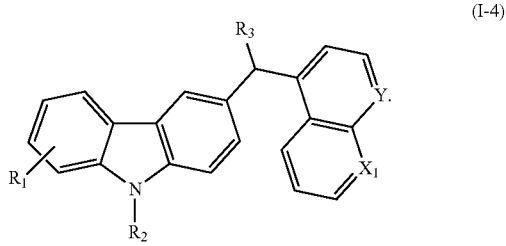

(I-4)

5. The compound of claim 1, wherein Y is N.

6. The compound of claim 1, wherein Y is $CR_4$.

7. The compound of claim 1, wherein $R_1$ is hydrogen, halogen, or $C_1$-$C_6$ alkyl.

8. The compound of claim 1, wherein $R_2$ is $C_1$-$C_6$ alkyl optionally substituted with one or more $R_7$, aryl($C_1$-$C_2$ alkyl) optionally substituted with one or more $R_8$, heteroaryl ($C_1$-$C_2$ alkyl) optionally substituted with one or more $R_8$, heterocyclyl($C_1$-$C_2$ alkyl) optionally substituted with one or more $R_7$, or cycloalkyl($C_1$-$C_2$ alkyl) optionally substituted with one or more $R_7$.

9. The compound of claim 1, wherein $R_2$ is $C_1$-$C_4$ alkyl.

10. The compound of claim 1, wherein $R_3$ is —OH, —O($C_1$-$C_6$ alkyl), —$NH_2$, —NH($C_1$-$C_6$ alkyl), or —N($C_1$-$C_6$ alkyl)$_2$.

11. The compound of claim 1, wherein the compound of formula (I) is substantially enantiomerically pure.

12. The compound of claim 1, wherein the compound of formula (I) is (−)-enantiomer.

13. The compound of claim 1, wherein the compound of formula (I) is (+)-enantiomer.

14. The compound of claim 1, which is:

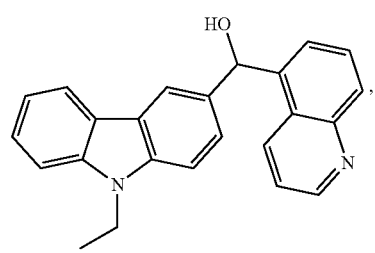

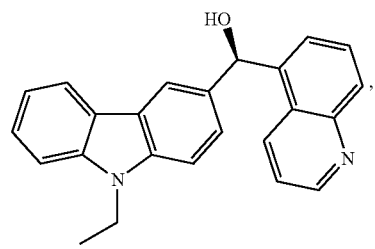

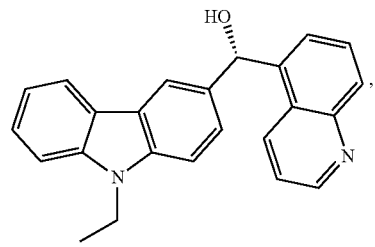

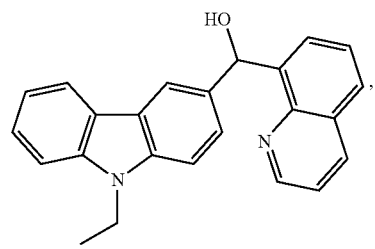

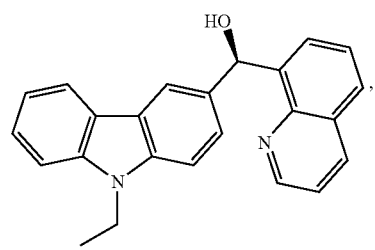

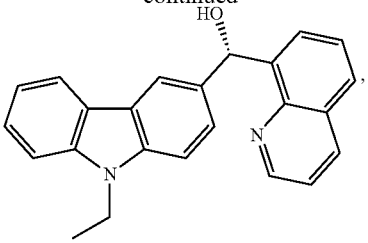

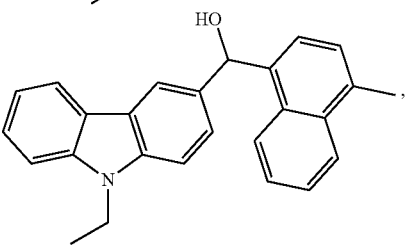

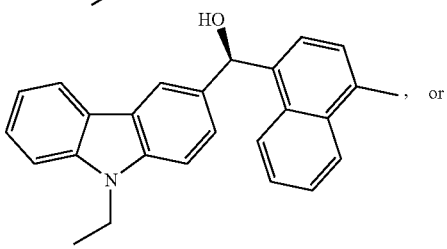, or

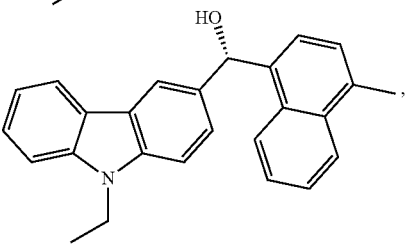

or a pharmaceutically acceptable salt thereof.

15. The compound of claim 1, which is: (9-ethyl-9H-carbazol-3-yl)(quinolin-5-yl)methanol, (9-ethyl-9H-carbazol-3-yl)(quinolin-8-yl)methanol, or (9-ethyl-9H-carbazol-3-yl)(4-methylnaphthalen-1-yl)methanol, or a pharmaceutically acceptable salt thereof, or a stereoisomer thereof.

16. A pharmaceutical composition including one or more compounds according to claim 1 and a pharmaceutically acceptable carrier, solvent, adjuvant or diluent.

17. A method of treating cancer, comprising administering one or more compounds according to claim 1 to a subject in need thereof.

18. The method of claim 17, further comprising administering one or more secondary therapeutic agents.

19. The method of claim 18, wherein the secondary therapeutic agents is selected from an antimetabolite, nucleoside analog, taxane, vinca alkaloid, microtubule inhibitor, alkylating agent, and a BRAF inhibitor.

20. The method of claim 17, wherein the cancer is selected from: BRAF-mutant cancers, melanoma, brain cancer, colorectal cancers, lung cancer, breast cancer, head and neck tumors, and lymphoma.

21. The method of claim 17, wherein the cancer is glioblastoma.

22. A method of disrupting MT function in a cell, comprising administering one or more compounds according to claim 1 to the cell.

23. The method of claim 17 wherein the cancer develops in peripheral tissues and metastasizes to the brain.

24. The compound of claim 1, which is (9-ethyl-9H-carbazol-3-yl)(quinolin-5-yl)methanol, or a pharmaceutically acceptable salt thereof, or a stereoisomer thereof.

* * * * *